United States Patent
Hu et al.

(10) Patent No.: US 9,487,570 B2
(45) Date of Patent: Nov. 8, 2016

(54) GLUCAGON LIKE PEPTIDE ANALOGS, COMPOSITION, AND METHOD OF USE

(75) Inventors: Shaojing Hu, Beijing (CN); Fenlai Tan, Beijing (CN); Yanping Wang, Beijing (CN); Cunbo Ma, Beijing (CN); Yunyan Hu, Beijing (CN); Hong Cao, Beijing (CN); Xiangdong Zhao, Beijing (CN); Wei Long, Beijing (CN); Yinxiang Wang, Beijing (CN); Lieming Ding, Beijing (CN)

(73) Assignee: BETTA PHARMACEUTICALS CO., LTD, Hangzhou (CN)

( * ) Notice: Subject to any disclaimer, the term of this patent is extended or adjusted under 35 U.S.C. 154(b) by 500 days.

(21) Appl. No.: 13/698,819

(22) PCT Filed: May 17, 2010

(86) PCT No.: PCT/CN2010/000692
§ 371 (c)(1),
(2), (4) Date: Feb. 1, 2013

(87) PCT Pub. No.: WO2011/143788
PCT Pub. Date: Nov. 24, 2011

(65) Prior Publication Data
US 2013/0203672 A1    Aug. 8, 2013

(51) Int. Cl.
| | |
|---|---|
| *A61K 38/26* | (2006.01) |
| *A61P 3/10* | (2006.01) |
| *A61P 7/12* | (2006.01) |
| *C07K 14/605* | (2006.01) |
| *A61K 38/00* | (2006.01) |
| *C07K 5/00* | (2006.01) |
| *C07K 7/00* | (2006.01) |
| *C07K 16/00* | (2006.01) |
| *C07K 17/00* | (2006.01) |
| *A61K 9/00* | (2006.01) |

(52) U.S. Cl.
CPC .......... *C07K 14/605* (2013.01); *A61K 9/0019* (2013.01); *A61K 38/00* (2013.01)

(58) Field of Classification Search
CPC .............................. C07K 14/605; A61K 38/26
See application file for complete search history.

(56) References Cited

U.S. PATENT DOCUMENTS

2003/0220255 A1 * 11/2003 Knudsen et al. ............... 514/12

FOREIGN PATENT DOCUMENTS

| CN | 1683408 A | * | 10/2005 | |
|---|---|---|---|---|
| WO | WO 2006068910 A1 | * | 6/2006 | ........... C07K 14/605 |
| WO | WO 2009030499 A1 | * | 3/2009 | ............. A61K 38/26 |

OTHER PUBLICATIONS

Wipf et al. "Peptide-Like Molecules (PLMs): A Journey from Peptide Bond Isosteres to Gramicidin S Mimetics and Mitochondrial Targeting Agents" Chimia (Aarau) 63:764-775. Published Nov. 1, 2009.*
Burcelin et al. "Long-Lasting Antidiabetic Effect of a Dipeptidyl Peptidase IV-Resistant Analog of Glucagon-Like Peptide-1" Metabolism 48:252-258. Published Feb. 1999.*
Peptides for Youth: The Proceedings of the 20th American Peptide Symposium. Ed. S. Del Valle et al. p. 475. Published 2009.*

* cited by examiner

*Primary Examiner* — James H Alstrum Acevedo
*Assistant Examiner* — Zachary J Miknis
(74) *Attorney, Agent, or Firm* — Weisun Rao; Greenberg Traurig, LLP

(57) ABSTRACT

The present invention relates to novel analogs of glucagon like peptide and compositions that are useful for up-regulating insulin expression in mammals and for treating diabetes. In particular, these peptide derivatives have a peptide mimic linker and provides long duration of action for the treatment of diabetes and other insulinotropic peptide related diseases, gastrointestinal function and activities associated with glucagon levels.

6 Claims, No Drawings

GLUCAGON LIKE PEPTIDE ANALOGS, COMPOSITION, AND METHOD OF USE

CROSS REFERENCE TO RELATED APPLICATION

This application is a national phase application and claims the benefit, under 35 U.S.C. §371, of PCT/CN2010/000692, filed on May 17, 2010, the contents of which are incorporated herein by reference.

FIELD OF THE INVENTION

The present invention relates to novel analogs of glucagon like peptide and compositions that are useful for up-regulating insulin expression in mammals and for treating diabetes. In particular, these peptide derivatives provides long duration of action for the treatment of diabetes and other insulinotropic peptide related diseases, gastrointestinal function and activities associated with glucangon levels.

BACKGROUND OF THE INVENTION

Endocrine secretion of pancreatic islets is regulated by a complex control mechanism driven not only by blob-borne metabolites such as glucose, amino acids, and catecholamines, but also by local paracrine influence. The major pancreatic islet hormones, glucagon, insulin and somatostatin, interact with specific pancreatic cell types (A, B, and D cells, respectively) to modulate the secretory response. Although insulin secretion is predominantly controlled by blood glucose levels, samotostatin inhibits glucose-mediated insulin secretion. In addition to interislet paracrine regulation of insulin secretion, there is evidence to support the existence of insulinotropic factors in the intestine. This incretin concept originates from the observation that food ingestion or enteral glucose administration provoked a greater stimulation of insulin release compared with similar amount of energy (glucose) infused intravenously (Elrick, H., et al., *J. Clin. Endocrinol. Metab.*, 24,1076-1082, 1964; McIntyre, N., et al., *J. Clin. Endocrinol. Metab.*, 25,1317-1324, 1965). Hence, it was postulated that gut-derived signals stimulated by oral nutrient ingestion represent potent insulin secretagogues responsible for the augmentation of insulin release when energy is administered via the gut versus parenteral route (Dupre, J., et al., *Diabetes*, 15, 555-559, 1966). Although several neurontrasmitters and gut hormones possess incretin-like activity, the considerable evidence from immunization, antagonist, and knockout studies suggest that glucose-dependent insulinotropic polypeptide (GIP) and glucagons-like peptide (GLP)-1 represent the dominant peptides responsible for the majority of nutrient-stimulated insulin secretion. The observation that patient with type 2 diabetes exhibit a significant reduction in the magnitude of meal-stimulated insulin secretion release underlies the interest in determining whether defective incretin release or resistance to incretin action contributes to the pathophysiology of β-cell dysfunction in diabetic subjects.

Glucagon-like peptide-1 (GLP-1) was first identified in 1987 as an incretin hormone, a peptide secreted by the gut upon ingestion of food. GLP1 is secreted by the L-cell of the intestine after being proteolytically processed from the 160amino acid precursor protein, preproglucagon. Cleavage of preproglucagon first yields GLP-1, a 37 amino acid peptide, GLP-1(1-37)OH, that is poorly active. A subsequent cleavage at the 7-position yields biologically active GLP-1 (7-37)OH. Approximately 80% of GLP-1(7-37)OH that is synthesized is amidated at the C-terminal after removal of the terminal glycine residue in the L-cell. The biological effects and metabolic turnover of the free acid GLP-1(7-37) OH and the amide, GLP-1(7-37)NH$_2$, are indistinguishable.

GLP-1 is known to stimulate insulin secretion causing glucose uptake by cells which decrease serum glucose levels (Mojsov, S., et al., *J. Clin.Invest.*, 79, 616-619, 1987; Kreymann, B., et al., *Lancet ii*,1300-1304, 1987; Orskov, C.,et al., *Endocrinology*, 123, 2009-2013, 1988). Acute intracerebroventricular injection of GLP-1 or GLP-1 receptor agonists produces transient reduction in food intake (Turton M.D., et al., *Nature*, 379, 60-72, 1996), whereas more prolonged intracerebroventricular or parenteral GLP-1 receptor agonists administration is associated with weight loss in some studies(Meeran, K., et al., *Endocrinology*, 140, 244-250, 1999; Davies, H. R. Jr., *Obes. Res.*, 6, 147-156, 1998; Szayna, M., et al., *Endocrinology*, 141, 1936-1941, 2000; Larsen, P. J., et al., *Diabetes*, 50, 2530-2539, 2001). Numerous GLP-1 analogs demonstrating insulinotropic action are know in the art. These analogs include, for example, GLP-1(7-36), Gln9-GLP-1(7-37), D-Gln9-GLP-1 (7-37), acetyl- Lys9-GLP-1(7-37), Thr16-Lys18-GLP-1(7-37) and Lys18-GLP-1(7-37). Derivatives of GLP-1 include, for example, acid addition salts, carboxylate salts, lower alkyl esters, and amides (WO91/11457; EP0733644; U.S. Pat. No. 5,512,549).

The majority of GLP-1 action delineated in preclinical experiments has also been demonstrated in human studies. Infusion of GLP-1(7-36)NH$_2$ into normal human subjects stimulated insulin secretion, significantly reduced blood glucose in the fasting state after glucose loading or food ingestion (Orskov, C., et al., *Diabetes*, 42, 658-661, 1993; Qualmann, C., et al., *Acta.Diabetol.*, 32, 13-16, 1995).

GLP-1 based peptides hold great promise as alternatives to insulin therapy for patients with diabetes who have failed on treatment with sulfonylureas (Nauck, M.A. et al., *Diabetes Care*, 21, 1925-1931, 1998). GLP-1 stimulates insulin secretion, but only during period of hyperglycemia. The safety of GLP-1 compared to insulin is enhanced by this property of GLP-1 and by the observation that the amount of insulin secreted is proportional to the magnitude of the hyperglycemia. In addition, GLP-1 therapy will result in pancreatic release of insulin and first-pass insulin action in the liver. These results in lower circulating levels of insulin in the periphery compared to subcutaneous insulin injections. GLP-1 slows gastric emptying which is desirable in that it spreads nutrient absorption over a longer period of time, decreasing the postprandial glucose peak. Several reports may suggest that GLP-1 can enhance insulin sensitivity in peripheral tissues such muscle, liver, and fat. Finally, GLP-1 has been shown to be a potential regulator of appetite.

The therapeutic potential for GLP-1 and its analogs is further increased if one considers its use in patients with type 1 diabetes. A number studies have demonstrated the effectiveness of native GLP-1 in the treatment of insulin dependent diabetes mellitus (IDDM).

Similar to non-insulin dependent diabetes mellitus (NIDDM) patients, GLP-1 is effective in reducing fasting hyperglycemia through its glucagonostatic properties. Additional studies have indicated that GLP-1 also reduces postprandial glycemic excursion in IDDM, most likely through a delaying in gastric emptying. These observations suggest that GLP-1 may be useful as a treatment for IDDM as well as for NIDDM.

However, the biologic half-life of native GLP-1 molecules which are effected by the activity of dipeptidylpeptidase IV (DPP IV) is quite short. For example, the biological half-life of GLP-1(7-37)OH is a mere 3 to 5 minutes (U.S. Pat. No. 5,118,666). Sustained lowering of blood glucose concentration is only observed with continuous infusion, as demonstrated in studies in which GLP-1 was administered by intravenous infusion over 24 hr time course (Larsen, J. et al. *Diabetes Care,* 24, 1416-1421, 2001). The enzyme DPP IV, a serine protease that preferentially hydrolyzed peptides after a penultimate $NH_2$-terminal proline (Xaa-Pro-) or alanine (Xaa-Ala-) (Mentlein, R., *Regul. Pept.,* 85, 9-25, 1999), has been shown to rapidly metabolize GLP-1 in vitro. Therefore extended- action GLP-1 based peptides that are resistant to DPP IV may have great therapeutic potential for treatment of diabetes mellitus.

DESCRIPTION OF THE INVENTION

The present invention provides novel GLP-1 analogs that have extended time action relative to native GLP-1 and are completely resistant to DPP IV hydrolysis.

The invention includes compounds of the general formula I (namely, formula of I is $Xaa_7$-Q-SEQ ID NO:1-B):

$Xaa_7$-Q-Gly-Thr-Phe-Thr-$Xaa_{14}$-Asp-$Xaa_{16}$-Ser-
$Xaa_{18}$-Tyr-Leu-Glu-$Xaa_{22}$-$Xaa_{23}$-Ala-Ala-
$Xaa_{26}$-$Xaa_{27}$-Phe-Ile-Ala-Trp-Leu-Val-$Xaa_{34}$-
$Xaa_{35}$-$Xaa_{36}$-B     I or a pharmaceutically acceptable salt thereof, wherein:

$Xaa_7$ is a natural or non natural amino acid selected from the group consisting of L-His, D-histidine, desamino-histidine, 2-amino-histidine, β-hydroxy-histidine, homohistidine, α-fluoromethyl-histidine, and α-methyl-histidine;

Q is selected from the following linkers (II), (III), (IV):

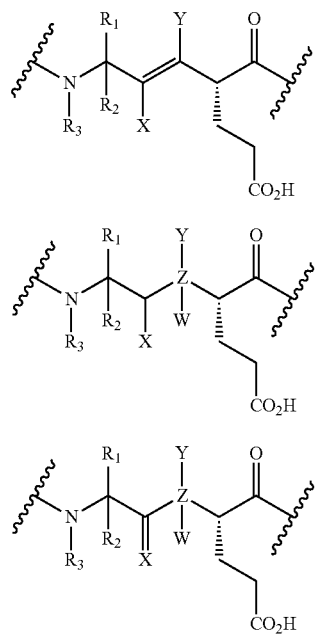

wherrerin $R_1$ is hydrogen, $(C_1\text{-}C_6)$ alkyl, or $(C_1\text{-}C_6)$alkoxy;
$R_2$ is hydrogen, $(C_1\text{-}C_6)$ alkyl, or $(C_1\text{-}C_6)$alkoxy;
$R_3$ is hydrogen, $(C_1\text{-}C_6)$ alkyl, or form a 5-8 member ring with $R_1$ or $R_2$;

X is hydrogen, fluorine, hydroxy, trifluoromethyl, or oxygen;
Y is hydrogen, hydroxyl, fluorine, or $(C_1\text{-}C_6)$ alkyl;
Z is nitrogen, carbon, oxygen, or sulphur;
W does not exist when Z is nitrogen, oxygen, or sulphur; or W is hydrogen or fluorine when Z is carbon;

$Xaa_{14}$ is a naturally or non-naturally occurring amino acid selected from the group consisting of serine and histidine, wherein one or more of the carbon atoms of said amino acid is optionally substituted with one or more alkyl groups;

$Xaa_{16}$ is a naturally or non-naturally occurring amino acid selected from the group consisting of valine, lysine and leucine, wherein one or more of the carbon atoms of said amino acid is optionally substituted with one or more alkyl groups; or $Xaa_{16}$ is lysine linked with T-U wherein T is γ-glutamic acid, β-alanine, γ-aminobutyric acid, or $HOOC(CH_2)_n COOH$, wherein n is 1, 2, 3, 4, 5, 6, 7, 8, 9, 10, 11, 12, 13, 14, 15, 16, 17, 18, 19, 20, 21, 22, 23, 24, 25, 26, or 27; or T is

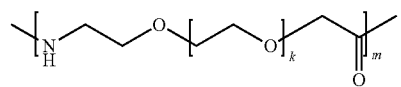

wherein k is 1, 2, 3, 4, 5, 6, 7, 8, 9 or 10, and m is 1, 2, 3, 4, 5, 6, 7, 8, 9, or 10;

U exists and is a fatty acid with a length of 8 to 20 carbons only when T is γ-glutamic acid, β-alanine, γ-aminobutyric acid, or

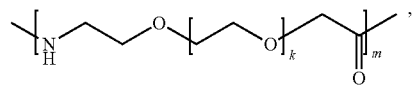

wherein k is 1, 2, 3, 4, 5, 6, 7, 8, 9, or 10 and m is 1, 2, 3, 4, 5, 6, 7, 8, 9, or 10;

$Xaa_{18}$ is a naturally or non-naturally occurring amino acid selected from the group consisting of serine, arginine and lysine, wherein one or more of the carbon atoms of said amino acid is optionally substituted with one or more alkyl groups;

$Xaa_{22}$ is a naturally or non-naturally occurring amino acid selected from the group consisting of glycine, Aib and glutamic acid, wherein one or more of the carbon atoms of said amino acid is optionally substituted with one or more alkyl groups;

$Xaa_{23}$ is naturally or non-naturally occurring amino acids selected from the group consisting of glutamine, glycine, Aib, and glutamic acid, wherein one or more of the carbon atoms of said amino acid is optionally substituted with one or more alkyl groups;

$Xaa_{27}$ is a naturally or non-naturally occurring amino acid selected from the group consisting of glutamic acid, lysine, arginine, leucine and asparagine, Aib (α-aminoisobutyric acid), wherein one or more of the carbon atoms of said amino acid is optionally substituted with one or more alkyl groups;

$Xaa_{26}$, $Xaa_{34}$, $Xaa_{35}$ and $Xaa_{36}$ are each independently glycine, lysine, arginine, leucine and asparagine, or Aib (α-aminoisobutyric acid), wherein one or more of the carbon atoms of said amino acid is optionally substituted with one or more alkyl groups; or $Xaa_{26}$ is lysine linked with T-U wherein T is γ-glutamic acid, β-alanine, γ-aminobutyric acid, or HOOC(CH$_2$)$_n$COOH, wherein n is 1, 2, 3, 4, 5, 6, 7, 8, 9, 10, 11, 12, 13, 14, 15, 16, 17, 18, 19, 20, 21, 22, 23, 24, 25, 26, or 27; or T is

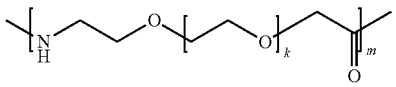

wherein k is 1, 2, 3, 4, 5, 6, 7, 8, 9 or 10, and m is 1, 2, 3, 4, 5, 6, 7, 8, 9, or 10;

U exists and is a fatty acid with a length of 8 to 20 carbons only when T is γ-glutamic acid, β-alanine, γ-aminobutyric acid, or

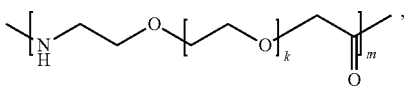

wherein k is 1, 2, 3, 4, 5, 6, 7, 8, 9, or 10 and m is 1, 2, 3, 4, 5, 6, 7, 8, 9, or 10;

B is selected from the group consisting of glycine, NH$_2$ and OH which represent the amide form or free acid of the terminal amino acid; or B is a peptide segment consisting of cysteine and one to four more amino acids each independently being cysteine, serine, glycine, alanine, or monomethoxypolyethylene glycol maleimide, examples including but not limited to cysteine-serine-glycine or cysteine-alanine, and monomethoxypolyethylene glycol maleimide linked to cysteine, when Xaa$_{26}$ is glycine, lysine, arginine, leucine and asparagine, or Aib (α-aminoisobutyric acid) and is not linked with T-U wherein T is γ-glutamic acid, β-alanine, γ-aminobutyric acid, or HOOC(CH$_2$)$_n$COOH, wherein n is 1, 2, 3, 4, 5, 6, 7, 8, 9, 10, 11, 12, 13, 14, 15, 16, 17, 18, 19, 20, 21, 22, 23, 24, 25, 26, or 27; or T is

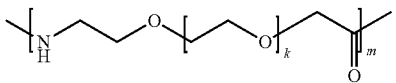

wherein k is 1, 2, 3, 4, 5, 6, 7, 8, 9 or 10, and m is 1, 2, 3, 4, 5, 6, 7, 8, 9, or 10;

U exists and is a fatty acid with a length of 8 to 20 carbons only when T is γ-glutamic acid, β-alanine, γ-aminobutyric acid, or

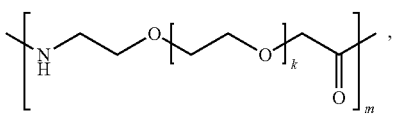

wherein k is 1, 2, 3, 4, 5, 6, 7, 8, 9, or 10 and m is 1, 2, 3, 4, 5, 6, 7, 8, 9, or 10.

Some preferred compounds are of Formula V:

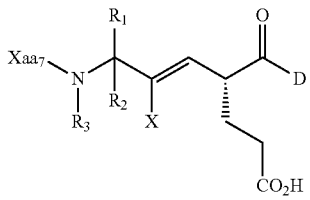

wherein

R$_1$ is hydrogen, (C$_1$-C$_6$) alkyl, or (C$_1$-C$_6$)alkoxy;

R$_2$ is hydrogen, (C$_1$-C$_6$) alkyl, or (C$_1$-C$_6$)alkoxy;

R$_3$ is hydrogen, (C$_1$-C$_6$) alkyl, or form a 5-8 member ring with R$_1$ or R$_2$;

X is hydrogen, fluorine, hydroxy, trifluoromethyl, or oxygen;

D is Gly-Thr-Phe-Thr-Xaa$_{14}$-Asp-Xaa$_{16}$-Ser-Xaa$_{18}$-Tyr-Leu-Glu-Xaa$_{22}$-Xaa$_{23}$-Ala-Ala-Xaa$_{26}$-Xaa$_{27}$-Phe-Ile-Ala-Trp-Leu-Val-Xaa$_{34}$-Xaa$_{35}$-Xaa$_{36}$-B (namely, formula of D is SEQ ID NO:1-B);

Xaa$_7$ is a natural or non natural amino acid selected from the group consisting of L-His, D-histidine, desamino-histidine, 2-amino-histidine, β-hydroxy-histidine, homohistidine, α-fluoromethyl-histidine, and α-methyl-histidine;

Xaa$_{14}$ is a naturally or non-naturally occurring amino acid selected from the group consisting of serine and histidine, wherein one or more of the carbon atoms of said amino acid is optionally substituted with one or more alkyl groups;

Xaa$_{16}$ is a naturally or non-naturally occurring amino acid selected from the group consisting of valine, lysine and leucine, wherein one or more of the carbon atoms of said amino acid is optionally substituted with one or more alkyl groups; or Xaa$_{16}$ is lysine linked with T-U wherein T is γ-glutamic acid, β-alanine, γ-aminobutyric acid, or HOOC(CH$_2$)$_n$COOH, wherein n is 1, 2, 3, 4, 5, 6, 7, 8, 9, 10, 11, 12, 13, 14, 15, 16, 17, 18, 19, 20, 21, 22, 23, 24, 25, 26, or 27; or T is

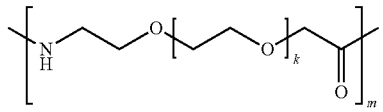

wherein k is 1, 2, 3, 4, 5, 6, 7, 8, 9 or 10, and m is 1, 2, 3, 4, 5, 6, 7, 8, 9, or 10;

U exists and is a fatty acid with a length of 8 to 20 carbons only when T is γ-glutamic acid, β-alanine, γ-aminobutyric acid, or

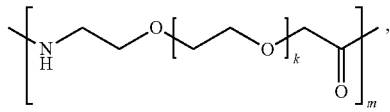

wherein k is 1, 2, 3, 4, 5, 6, 7, 8, 9, or 10 and m is 1, 2, 3, 4, 5, 6, 7, 8, 9, or 10;

Xaa$_{18}$ is a naturally or non-naturally occurring amino acid selected from the group consisting of serine, arginine and lysine, wherein one or more of the carbon atoms of said amino acid is optionally substituted with one or more alkyl groups;

Xaa$_{22}$ is a naturally or non-naturally occurring amino acid selected from the group consisting of glycine, Aib and glutamic acid, wherein one or more of the carbon atoms of said amino acid is optionally substituted with one or more alkyl groups;

Xaa$_{23}$ is a naturally or non-naturally occurring amino acid selected from the group consisting of glutamine, glycine, Aib and glutamic acid, wherein one or more of the carbon atoms of said amino acid is optionally substituted with one or more alkyl groups;

Xaa$_{27}$ is a naturally or non-naturally occurring amino acid selected from the group consisting of glutamic acid, glycine, lysine, arginine, leucine and asparagine, Aib (α-aminoisobutyric acid), wherein one or more of the carbon atoms of said amino acid is optionally substituted with one or more alkyl groups;

Xaa$_{26}$, Xaa$_{34}$, Xaa$_{35}$ and Xaa$_{36}$ are each independently glycine, lysine, arginine, leucine and asparagine, or Aib (α-aminoisobutyric acid), wherein one or more of the carbon atoms of said amino acid is optionally substituted with one or more alkyl groups; or Xaa$_{26}$ is lysine linked with T-U wherein T is γ-glutamic acid, β-alanine, γ-aminobutyric acid, or HOOC(CH$_2$)$_n$COOH, wherein n is 1, 2, 3, 4, 5, 6, 7, 8, 9, 10, 11, 12, 13, 14, 15, 16, 17, 18, 19, 20, 21, 22, 23, 24, 25, 26, or 27; or T is

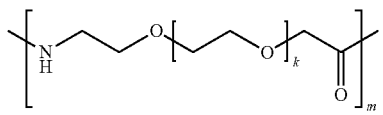

wherein k is 1, 2, 3, 4, 5, 6, 7, 8, 9 or 10, and m is 1, 2, 3, 4, 5, 6, 7, 8, 9, or 10;

U exists and is a fatty acid with a length of 8 to 20 carbons only when T is γ-glutamic acid, β-alanine, γ-aminobutyric acid, or

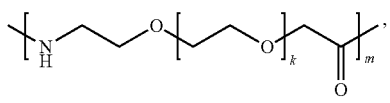

wherein k is 1, 2, 3, 4, 5, 6, 7, 8, 9, or 10 and m is 1, 2, 3, 4, 5, 6, 7, 8, 9, or 10;

B is selected from the group consisting of glycine, NH$_2$ and OH which represent the amide form or free acid of the terminal amino acid; or when Xaa$_{26}$ is glycine, lysine, arginine, leucine and asparagine, or Aib (α-aminoisobutyric acid) and is not linked with T-U, B is a peptide segment consisting of cysteine and one to four more amino acids each independently being cysteine, serine, glycine, alanine, or monomethoxypolyethylene glycol maleimide, examples including but not limited to cysteine-serine-glycine or cysteine-alanine, and monomethoxypolyethylene glycol maleimide linked to cysteine, wherein T is γ-glutamic acid, β-alanine, γ-aminobutyric acid, HOOC(CH$_2$)$_n$COOH, or

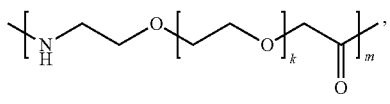

wherein n is 1, 2, 3, 4, 5, 6, 7, 8, 9, 10, 11, 12, 13, 14, 15, 16, 17, 18, 19, 20, 21, 22, 23, 24, 25, 26, or 27; k is 1, 2, 3, 4, 5, 6, 7, 8, 9, or 10, and m is 1, 2, 3, 4, 5, 6, 7, 8, 9, or 10;

U exists and is a fatty acid with length of 8 to 20 carbons only when T is γ-glutamic acid, β-alanine, γ-aminobutyric acid, or

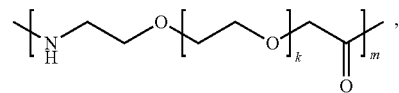

wherein k is 1, 2, 3, 4, 5, 6, 7, 8, 9, or 10, and m is 1, 2, 3, 4, 5, 6, 7, 8, 9, or 10.

In some embodiments, R$_3$ is hydrogen, or R$_3$, together with R$_1$ or R$_2$, form a 5-8 member.

In some embodiments, X is hydrogen, fluorine, or trifluoromethyl.

In some embodiments, each of R$_1$, R$_2$ and R$_3$ is hydrogen or methyl.

In some embodiments, R$_1$ is methyl, R$_2$ and R$_3$ are hydrogen.

In some embodiments, R$_1$ and R$_3$ are hydrogen and R$_2$ is methyl.

In some embodiments, R$_3$ and R$_1$ together form a 5-8 member ring and R$_2$ is hydrogen; or R$_3$ and R$_2$ together form a 5-8 member ring and R$_1$ is hydrogen.

Some preferred compounds are of Formula VI:

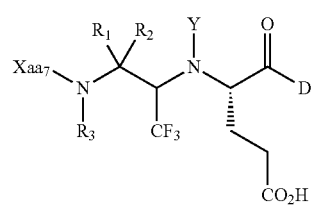

VI wherein
R$_1$ is hydrogen, (C$_1$-C$_6$) alkyl, or (C$_1$-C$_6$)alkoxy;
R$_2$ is hydrogen, (C$_1$-C$_6$) alkyl, or (C$_1$-C$_6$)alkoxy;
R$_3$ is hydrogen, (C$_1$-C$_6$) alkyl, or form a 5-8 member ring with R$_1$ or R$_2$;
Y is hydrogen, hydroxyl, fluorine, or (C$_1$-C$_6$) alkyl;
D is Gly-Thr-Phe-Thr-Xaa$_{14}$-Asp-Xaa$_{16}$-Ser-Xaa$_{18}$-Tyr-Leu-Glu-Xaa$_{22}$-Xaa$_{23}$-Ala-Ala-Xaa$_{26}$-Xaa$_{27}$-Phe-Ile-Ala-Trp-Leu-Val-Xaa$_{34}$-Xaa$_{35}$-Xaa$_{36}$-B (namely, formula D is SEQ ID NO: 1-B);

Xaa$_7$ is a natural or non natural amino acid selected from the group consisting of L-His, D-histidine, desamino-histidine, 2-amino-histidine, β-hydroxy-histidine, homohistidine, α-fluoromethyl-histidine, and α-methyl-histidine;

Xaa$_{14}$ is a naturally or non-naturally occurring amino acid selected from the group consisting of serine and histidine, wherein one or more of the carbon atoms of said amino acid is optionally substituted with one or more alkyl groups;

Xaa$_{16}$ is a naturally or non-naturally occurring amino acid selected from the group consisting of valine, lysine and leucine, wherein one or more of the carbon atoms of said amino acid is optionally substituted with one or more alkyl groups; or Xaa$_{16}$ is lysine linked with T-U wherein T is γ-glutamic acid, β-alanine, γ-aminobutyric acid, HOOC(CH$_2$)$_n$COOH, or

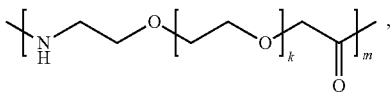

wherein n is 1, 2, 3, 4, 5, 6, 7, 8, 9, 10, 11, 12, 13, 14, 15, 16, 17, 18, 19, 20, 21, 22, 23, 24, 25, 26, or 27; k is 1, 2, 3, 4, 5, 6, 7, 8, 9, or 10, and m is 1, 2, 3, 4, 5, 6, 7, 8, 9, or 10;

U exists and is a fatty acid with length of 8 to 20 carbons only when T is γ-glutamic acid, β-alanine, γ-aminobutyric acid, or

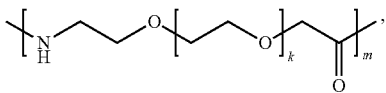

wherein k is 1, 2, 3, 4, 5, 6, 7, 8, 9, or 10, and m is 1, 2, 3, 4, 5, 6, 7, 8, 9, or 10;

$Xaa_{18}$ is a naturally or non-naturally occurring amino acid selected from the group consisting of serine, arginine and lysine, wherein one or more of the carbon atoms of said amino acid is optionally substituted with one or more alkyl groups;

$Xaa_{22}$ is a naturally or non-naturally occurring amino acid selected from the group consisting of glycine, Aib and glutamic acid, wherein one or more of the carbon atoms of said amino acid is optionally substituted with one or more alkyl groups;

$Xaa_{23}$ is a naturally or non-naturally occurring amino acid selected from the group consisting of glutamine, glycine, Aib and glutamic acid, wherein one or more of the carbon atoms of said amino acid is optionally substituted with one or more alkyl groups;

$Xaa_{27}$ is a naturally or non-naturally occurring amino acid selected from the group consisting of glutamic acid, lysine, arginine, leucine and asparagine, Aib (α-aminoisobutyric acid), wherein one or more of the carbon atoms of said amino acid is optionally substituted with one or more alkyl groups;

$Xaa_{26}$, $Xaa_{34}$, $Xaa_{35}$ and $Xaa_{36}$ are each independently glycine, lysine, arginine, leucine and asparagine, or Aib (α-aminoisobutyric acid), wherein one or more of the carbon atoms of said amino acid is optionally substituted with one or more alkyl groups; or $Xaa_{26}$ is lysine linked with T-U wherein T is γ-glutamic acid, β-alanine, γ-aminobutyric acid, $HOOC(CH_2)_nCOOH$, or

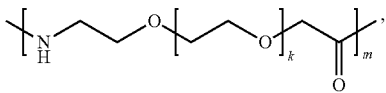

wherein n is 1, 2, 3, 4, 5, 6, 7, 8, 9, 10, 11, 12, 13, 14, 15, 16, 17, 18, 19, 20, 21, 22, 23, 24, 25, 26, or 27; k is 1, 2, 3, 4, 5, 6, 7, 8, 9, or 10, and m is 1, 2, 3, 4, 5, 6, 7, 8, 9, or 10;

U exists and is a fatty acid with length of 8 to 20 carbons only when T is γ-glutamic acid, β-alanine, γ-aminobutyric acid, or

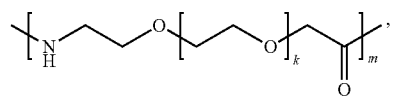

wherein k is 1, 2, 3, 4, 5, 6, 7, 8, 9, or 10, and m is 1, 2, 3, 4, 5, 6, 7, 8, 9, or 10;

B is selected from the group consisting of glycine, $NH_2$ and OH which represent the amide form or free acid of the terminal amino acid; or when $Xaa_{26}$ is glycine, lysine, arginine, leucine and asparagine, or Aib (α-aminoisobutyric acid) and is not linked with T-U, B is a peptide segment consisting of cysteine and one to four more amino acids each independently being cysteine, serine, glycine, alanine, or monomethoxypolyethylene glycol maleimide, examples including but not limited to cysteine-serine-glycine or cysteine-alanine, and monomethoxypolyethylene glycol maleimide linked to cysteine, wherein T is γ-glutamic acid, β-alanine, γ-aminobutyric acid, $HOOC(CH_2)_nCOOH$, or

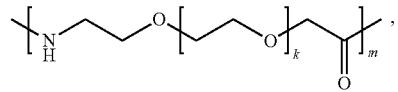

wherein n is 1, 2, 3, 4, 5, 6, 7, 8, 9, 10, 11, 12, 13, 14, 15, 16, 17, 18, 19, 20, 21, 22, 23, 24, 25, 26, or 27; k is 1, 2, 3, 4, 5, 6, 7, 8, 9, or 10, and m is 1, 2, 3, 4, 5, 6, 7, 8, 9, or 10;

U exists and is a fatty acid with length of 8 to 20 carbons only when T is γ-glutamic acid, β-alanine, γ-aminobutyric acid, or

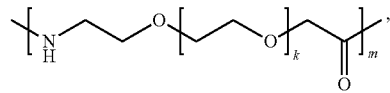

wherein k is 1, 2, 3, 4, 5, 6, 7, 8, 9, or 10, and m is 1, 2, 3, 4, 5, 6, 7, 8, 9, or 10.

In some embodiments, $R_3$ is hydrogen.
In some embodiments, Y is hydrogen or $(C_1-C_6)$ alkyl.
Some other preferred compounds are of Formula VII:

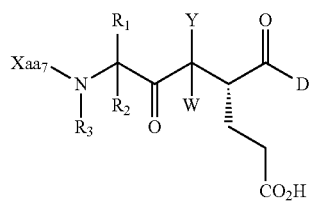

wherein
$R_1$ is hydrogen, $(C_1-C_6)$ alkyl, or $(C_1-C_6)$alkoxy;
$R_2$ is hydrogen, $(C_1-C_6)$ alkyl, or $(C_1-C_6)$alkoxy;.
$R_3$ is hydrogen, $(C_1-C_6)$ alkyl, or form a 5-8 member ring with $R_1$ or $R_2$;
Y is hydrogen, hydroxyl, fluorine, or $(C_1-C_6)$ alkyl;
W is hydrogen or fluorine;
D is Gly-Thr-Phe-Thr-$Xaa_{14}$-Asp-$Xaa_{16}$-Ser-$Xaa_{18}$-Tyr-Leu-Glu-$Xaa_{22}$-$Xaa_{23}$-Ala-Ala-$Xaa_{26}$-$Xaa_{27}$-Phe-Ile-Ala-Trp-Leu-Val-$Xaa_{34}$-$Xaa_{35}$-$Xaa_{36}$-B (namely, formula D is SEQ ID NO:1-B);

Xaa₇ is a natural or non natural amino acid selected from the group consisting of L-His, D-histidine, desamino-histidine, 2-amino-histidine, β-hydroxy-histidine, homohistidine, α-fluoromethyl-histidine, and α-methyl-histidine;

Xaa₁₄ is a naturally or non-naturally occurring amino acid selected from the group consisting of serine and histidine, wherein one or more of the carbon atoms of said amino acid is optionally substituted with one or more alkyl groups;

Xaa₁₆ is a naturally or non-naturally occurring amino acid selected from the group consisting of valine, lysine and leucine, wherein one or more of the carbon atoms of said amino acid is optionally substituted with one or more alkyl groups; or Xaa₁₆ is lysine linked with T-U wherein T is γ-glutamic acid, β-alanine, γ-aminobutyric acid, HOOC(CH₂)$_n$COOH, or

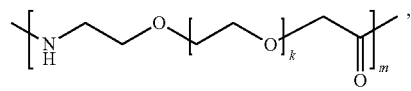

wherein n is 1, 2, 3, 4, 5, 6, 7, 8, 9, 10, 11, 12, 13, 14, 15, 16, 17, 18, 19, 20, 21, 22, 23, 24, 25, 26, or 27; k is 1, 2, 3, 4, 5, 6, 7, 8, 9, or 10, and m is 1, 2, 3, 4, 5, 6, 7, 8, 9, or 10;

U exists and is a fatty acid with length of 8 to 20 carbons only when T is γ-glutamic acid, β-alanine, γ-aminobutyric acid, or

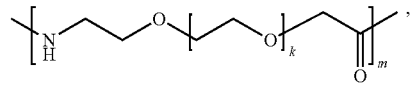

wherein k is 1, 2, 3, 4, 5, 6, 7, 8, 9, or 10, and m is 1, 2, 3, 4, 5, 6, 7, 8, 9, or 10;

Xaa₁₈ is a naturally or non-naturally occurring amino acid selected from the group consisting of serine, arginine and lysine, wherein one or more of the carbon atoms of said amino acid is optionally substituted with one or more alkyl groups;

Xaa₂₂ is a naturally or non-naturally occurring amino acid selected from the group consisting of glycine, Aib and glutamic acid, wherein one or more of the carbon atoms of said amino acid is optionally substituted with one or more alkyl groups;

Xaa₂₃ is a naturally or non-naturally occurring amino acid selected from the group consisting of glutamine, glycine, Aib and glutamic acid, wherein one or more of the carbon atoms of said amino acid is optionally substituted with one or more alkyl groups;

Xaa₂₇ is a naturally or non-naturally occurring amino acid selected from the group consisting of glutamic acid, glycine, lysine, arginine, leucine and asparagine, and Aib (α-aminoisobutyric acid), wherein one or more of the carbon atoms of said amino acid is optionally substituted with one or more alkyl groups;

Xaa₂₆, Xaa₃₄, Xaa₃₅ and Xaa₃₆ are each independently glycine, lysine, arginine, leucine and asparagine, or Aib (α-aminoisobutyric acid), wherein one or more of the carbon atoms of said amino acid is optionally substituted with one or more alkyl groups; or Xaa₂₆ is lysine linked with T-U wherein T is γ-glutamic acid, β-alanine, γ-aminobutyric acid, HOOC(CH₂)$_n$COOH, or

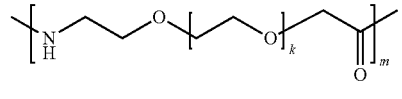

wherein n is 1, 2, 3, 4, 5, 6, 7, 8, 9, 10, 11, 12, 13, 14, 15, 16, 17, 18, 19, 20, 21, 22, 23, 24, 25, 26, or 27; k is 1, 2, 3, 4, 5, 6, 7, 8, 9, or 10, and m is 1, 2, 3, 4, 5, 6, 7, 8, 9, or 10;

U exists and is a fatty acid with length of 8 to 20 carbons only when T is γ-glutamic acid, β-alanine, γ-aminobutyric acid, or

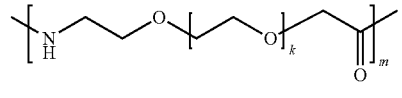

wherein k is 1, 2, 3, 4, 5, 6, 7, 8, 9, or 10, and m is 1, 2, 3, 4, 5, 6, 7, 8, 9, or 10;

B is selected from the group consisting of glycine, NH₂ and OH which represent the amide form or free acid of the terminal amino acid; or when Xaa₂₆ is glycine, lysine, arginine, leucine and asparagine, or Aib (α-aminoisobutyric acid) and is not linked with T-U, B is a peptide segment consisting of cysteine and one to four more amino acids each independently being cysteine, serine, glycine, alanine, or monomethoxypolyethylene glycol maleimide, examples including but not limited to cysteine-serine-glycine or cysteine-alanine, and monomethoxypolyethylene glycol maleimide linked to cysteine, wherein T is γ-glutamic acid, β-alanine, γ-aminobutyric acid, HOOC(CH₂)$_n$COOH, or

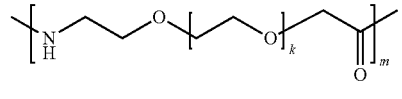

wherein n is 1, 2, 3, 4, 5, 6, 7, 8, 9, 10, 11, 12, 13, 14, 15, 16, 17, 18, 19, 20, 21, 22, 23, 24, 25, 26, or 27; k is 1, 2, 3, 4, 5, 6, 7, 8, 9, or 10, and m is 1, 2, 3, 4, 5, 6, 7, 8, 9, or 10;

U exists and is a fatty acid with length of 8 to 20 carbons only when T is γ-glutamic acid, β-alanine, γ-aminobutyric acid, or

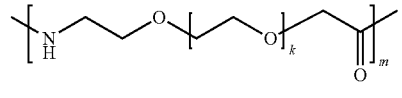

wherein k is 1, 2, 3, 4, 5, 6, 7, 8, 9, or 10, and m is 1, 2, 3, 4, 5, 6, 7, 8, 9, or 10.

In some embodiments, R₃ is hydrogen or form a 5-8 member ring with R₁ or R₂.

In some embodiments, Y is hydrogen or fluorine.

In some embodiments, W is hydrogen or fluorine.

Some preferred compounds are of Formula VIII:

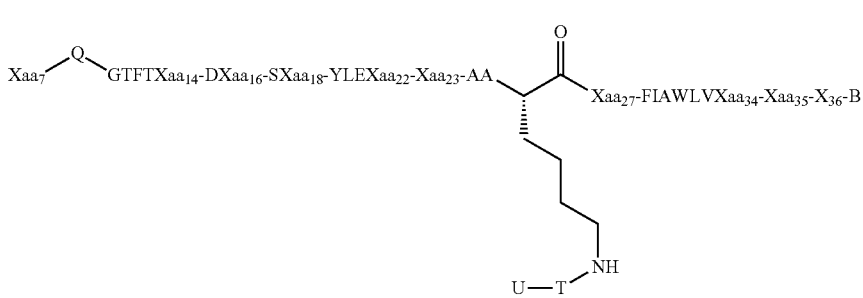

VIII or a pharmaceutically acceptable salt thereof, wherein:

$Xaa_7$ is a natural or non natural amino acid selected from the group consisting of L-His, D-histidine, desamino-histidine, 2-amino-histidine, β-hydroxy-histidine, homohistidine, α-fluoromethyl-histidine, and α-methyl-histidine;

Q is selected from the following linkers (II), (III), or (IV):

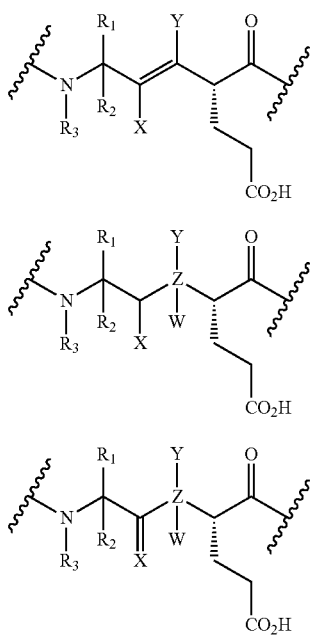

wherein
$R_1$ is hydrogen, $(C_1-C_6)$ alkyl, or $(C_1-C_6)$alkoxy;
$R_2$ is hydrogen, $(C_1-C_6)$ alkyl, or $(C_1-C_6)$alkoxy;
$R_3$ is hydrogen, $(C_1-C_6)$ alkyl, or form a 5-8 member ring with $R_1$ or $R_2$;
X is hydrogen, fluorine, hydroxy, trifluoromethyl, or oxygen;
Y is hydrogen, hydroxyl, fluorine, or $(C_1-C_6)$ alkyl;
Z is nitrogen, carbon, oxygen, or sulphur;
W does not exist when Z is nitrogen, oxygen, or sulphur, or W is hydrogen or fluorine when Z is carbon;

$Xaa_{14}$ is a naturally or non-naturally occurring amino acid selected from the group consisting of serine, and histidine, wherein one or more of the carbon atoms of said amino acid is optionally substituted with one or more alkyl groups;

$Xaa_{16}$ is a naturally or non-naturally occurring amino acid selected from the group consisting of valine, lysine and leucine, wherein one or more of the carbon atoms of said amino acid is optionally substituted with one or more alkyl groups;

$Xaa_{18}$ is a naturally or non-naturally occurring amino acid selected from the group consisting of serine, arginine and lysine, wherein one or more of the carbon atoms of said amino acid is optionally substituted with one or more alkyl groups;

$Xaa_{22}$ is a naturally or non-naturally occurring amino acid selected from the group consisting of glycine, Aib and glutamic acid, wherein one or more of the carbon atoms of said amino acid is optionally substituted with one or more alkyl groups;

$Xaa_{23}$ is a naturally or non-naturally occurring amino acid selected from the group consisting of glutamine, glycine, Aib and glutamic acid, wherein one or more of the carbon atoms of said amino acid is optionally substituted with one or more alkyl groups;

$Xaa_{27}$ is a naturally or non-naturally occurring amino acid selected from the group consisting of glutamic acid, glycine, lysine, arginine, leucine and asparagine, and Aib (α-aminoisobutyric acid), wherein one or more of the carbon atoms of said amino acid is optionally substituted with one or more alkyl groups;

$Xaa_{34}$, $Xaa_{35}$ and $Xaa_{36}$ are each independently glycine, lysine, arginine, leucine and asparagine, or Aib (α-aminoisobutyric acid), wherein one or more of the carbon atoms of said amino acid is optionally substituted with one or more alkyl groups;

B is selected from the group consisting of glycine, $NH_2$ and OH which represent the amide form or free acid of the terminal amino acid;

T is γ-glutamic acid, β-alanine, γ-aminobutyric acid, $HOOC(CH_2)_nCOOH$, or

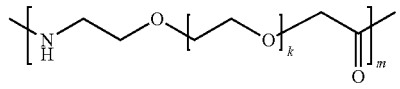

wherein n is 1, 2, 3, 4, 5, 6, 7, 8, 9, 10, 11, 12, 13, 14, 15, 16, 17, 18, 19, 20, 21, 22, 23, 24, 25, 26, or 27; k is 1, 2, 3, 4, 5, 6, 7, 8, 9, or 10, and m is 1, 2, 3, 4, 5, 6, 7, 8, 9, or 10;

U exists and is a fatty acid with length of 8 to 20 carbons only when T is γ-glutamic acid, β-alanine, γ-aminobutyric acid, or

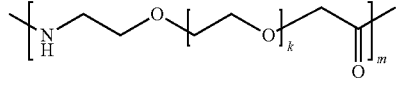

wherein k is 1, 2, 3, 4, 5, 6, 7, 8, 9, or 10, and m is 1, 2, 3, 4, 5, 6, 7, 8, 9, or 10.

Some other preferred compounds are of Formula IX (namely, formula IX is $Xaa_7$-Q-SEQ ID NO:2-$Xaa^n$-$Xaa^{n+1}$-$Xaa^{n+2}$-$Xaa^{n+3}$-$Xaa^{n+4}$-$Cys^{(PEG)}$-$Xaa^m$-$Xaa^{m+1}$-$Xaa^{m+2}$-$Xaa^{m+3}$-$Xaa^{m+4}$):

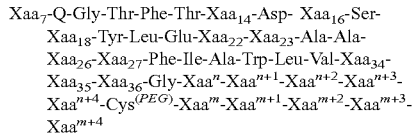

IX or a pharmaceutically acceptable salt thereof, wherein:

$Xaa_7$ is a natural or non natural amino acid selected from the group consisting of L-His, D-histidine, desamino-histidine, 2-amino-histidine, β-hydroxy-histidine, homohistidine, α-fluoromethyl-histidine, and α-methyl-histidine;

Q is selected from the following linkers (II), (III), or (IV):

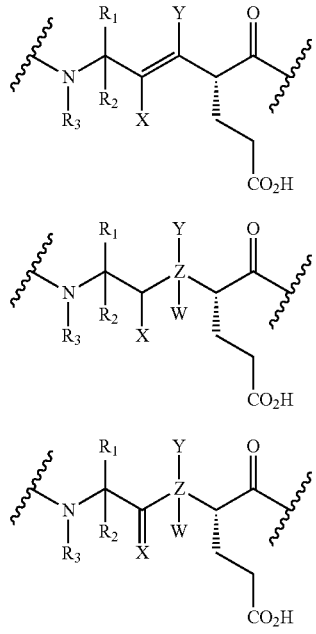

wherein
R$_1$ is hydrogen, (C$_1$-C$_6$) alkyl, or (C$_1$-C$_6$)alkoxy;
R$_2$ is hydrogen, (C$_1$-C$_6$) alkyl, or (C$_1$-C$_6$)alkoxy;
R$_3$ is hydrogen, (C$_1$-C$_6$) alkyl, or form a 5-8 member ring with R$_1$ or R$_2$;
X is hydrogen, fluorine, hydroxy, trifluoromethyl, or oxygen;
Y is hydrogen, hydroxyl, fluorine, or (C$_1$-C$_6$) alkyl;
Z is nitrogen, carbon, oxygen, or sulphur;
W does not exist when Z is nitrogen, oxygen, or sulphur, or W is hydrogen or fluorine when Z is carbon;
$Xaa_{14}$ is a naturally or non-naturally occurring amino acid selected from the group consisting of serine, and histidine, wherein one or more of the carbon atoms of said amino acid is optionally substituted with one or more alkyl groups;
$Xaa_{16}$ is a naturally or non-naturally occurring amino acid selected from the group consisting of valine, lysine and leucine, wherein one or more of the carbon atoms of said amino acid is optionally substituted with one or more alkyl groups;

$Xaa_{18}$ is a naturally or non-naturally occurring amino acid selected from the group consisting of serine, arginine and lysine, wherein one or more of the carbon atoms of said amino acid is optionally substituted with one or more alkyl groups;

$Xaa_{22}$ is a naturally or non-naturally occurring amino acid selected from the group consisting of glycine, Aib and glutamic acid, wherein one or more of the carbon atoms of said amino acid is optionally substituted with one or more alkyl groups;

$Xaa_{23}$ is a naturally or non-naturally occurring amino acid selected from the group consisting of glutamine, glycine, Aib and glutamic acid, wherein one or more of the carbon atoms of said amino acid is optionally substituted with one or more alkyl groups;

$Xaa_{27}$ is a naturally or non-naturally occurring amino acid selected from the group consisting of glutamic acid, glycine, lysine, arginine, leucine and asparagine, Aib (α-aminoisobutyric acid), wherein one or more of the carbon atoms of said amino acid is optionally substituted with one or more alkyl groups;

$Xaa_{26}$, $Xaa_{34}$, $Xaa_{35}$ and $Xaa_{36}$ are each independently glycine, lysine, arginine, leucine and asparagine, or Aib (α-aminoisobutyric acid), wherein one or more of the carbon atoms of said amino acid is optionally substituted with one or more alkyl groups;

$Xaa^n$, $Xaa^{n+1}$, $Xaa^{n+2}$, $Xaa^{n+3}$, $Xaa^{n+4}$, all together, do not exist or are a peptide segment of one, or two, or three or four amino acids and $Xaa^m$, $Xaa^{m+1}$, $Xaa^{m+2}$, $Xaa^{m+3}$, and $Xaa^{m+4}$, all together, do not exist or are a peptide segment of one, two, three, or four amino acids; provided that the total number of amino acids provided by all of $Xaa^n$, $Xaa^{n+1}$, $Xaa^{n+2}$, $Xaa^{n+3}$, $Xaa^{n+4}$, $Xaa^m$, $Xaa^{m+1}$, $Xaa^{m+2}$, $Xaa^{m+3}$, and $Xaa^{m+4}$ is 1, 2, 3, or 4, and cysteine is linked to monomethoxypolyethylene glycol maleimide.

The flowing compounds of the invention are provided to give the reader an understanding of the compounds encompassed by the invention:

[Q-linker-d8, Glu22]GLP-1-(7-37)-peptide;
[Q-linker-a8-9, Glu22]GLP-1-(7-37)-peptide;
[Q-linker-b8-9, Glu22]GLP-1-(7-37)-peptide;
[Q-linker-c8, Glu22]GLP-1-(7-37)-peptide;
[Q-linker-e8-9, Glu22]GLP-1-(7-37)-peptide;
[Q-linker-f-9,Arg34]GLP-1-(7-37)-peptide;
N-$\epsilon^{26}$-[γ-L-glutamyl(N-α-hexadecanoyl)]-[Q-linker-c8, Arg34]GLP-1-(7-37)-peptide;
N-$\epsilon^{26}$-[γ-L-glutamyl(N-α-hexadecanoyl)]-[Q-linker-d8, Arg34]GLP-1-(7-37)-peptide;
N-$\epsilon^{26}$-[γ-L-glutamyl(N-α-hexadecanoyl)]-[Q-linker-e8-9,Arg34]GLP-1-(7-37)-peptide;
N-$\epsilon^{26}$-[γ-L-glutamyl(N-α-hexadecanoyl)]-[Q-linker-f8-9, Arg34]GLP-1-(7-37)-peptide;
N-$\epsilon^{26}$-[γ-L-glutamyl(N-α-hexadecanoyl)]-[Q-linker-a8-9,Arg34]GLP-1-(7-37)-peptide;
N-$\epsilon^{26}$-[γ-L-glutamyl(N-α-hexadecanoyl)]-[Q-linker-b8-9,Arg34]GLP-1-(7-37)-peptide;
N-$\epsilon^{26}$-[(N$^\epsilon$-ω-carboxyheptadecanoyl)]-[Q-linker-c8, Arg34]GLP-1 -(7-37)-peptide;
N-$\epsilon^{26}$-[(N$^\epsilon$-ω-carboxynonadecanoyl)]-[Q-linker-c8, Arg34]GLP- 1 -(7-37)-peptide;
Q-linker-d8]GLP-1-(7-37)-$Cys^{(PEG)}$-Ala-NH$_2$;
Q-linker-c8]GLP-1-(7-37)-$Cys^{(PEG)}$-Ala-NH$_2$;
Q-linker-a8-9]GLP-1-(7-37)-$Cys^{(PEG)}$-Ala-NH$_2$;
Q-linker-b8-9]GLP-1-(7-37)-$Cys^{(PEG)}$-Ala-NH$_2$;
Q-linker-e8-9]GLP-1-(7-37)-$Cys^{(PEG)}$-Ala-NH$_2$;
Q-linker-f8-9]GLP-1-(7-37)-$Cys^{(PEG)}$-Ala-NH$_2$.

Key to the present invention is to replace the amide bond of Ala$^8$ of the amino terminal of GLP-1, which is the recognition site for DPP-IV, with the peptide bond mimic linkers. The peptide bond mimic linkers are a classical approach in drug discovery by mimic natural peptide bond and which retain the ability to interact with the biological targets and produce the same biological effects (*Curr Chem Bio,* 12, 292-296, 2008). Based on the same principle, the peptide bond mimic linkers modified GLP-1 analogs should retain the same biological activity and have long duration of action as insulinotropic agents.

The compounds of the invention may have one or more asymmetric centers, such as A-linker in Formula I. Such compounds may be present in one or more stereoisomeric forms. These compounds can be, for example, racemates, optically active forms, or enantiomerically enriched mixtures of stereoisomers. Where desired, the single enantiomers, i. e., optically active forms, can be obtained by known procedures, e. g., by asymmetric synthesis, by synthesis from optically active starting materials, or by resolution of the racemates. Resolution of the racemates can be accomplished by conventional methods such as, for example, crystallization in the presence of a resolving agent; derivatization with an enantiomerically pure or enriched resolving reagent followed by isolation of the desired isomer; or chromatography, using, for example a chiral HPLC column.

The term "polypeptide" and "peptide" as used herein means a compound composed of at least five constituent amino acids connected by peptide bonds. The constituent amino acids may be from the group of the amino acids encoded by the genetic code and they may be natural amino acids which are not encoded by the genetic code, as well as synthetic amino acids. Natural amino acids which are not encoded by the genetic code are e.g., v-carboxyglutamate, ornithine, phosphoserine, D-alanine and D-glutamine. Synthetic amino acids comprise amino acids manufactured by chemical synthesis, i.e. D-isomers of the amino acids encoded by the genetic code such as D-alanine and D-leucine, Aib (α-aminoisobutyric acid), Abu (α-aminobutyric acid), Tie (tert-butylglycine), β-alanine, 3-aminomethyl benzoic acid, anthranilic acid.

The 22 proteogenic amino acids are: Alanine, Arginine, Asparagine, Aspartic acid, Cysteine, Cystine, Glutamine, Glutamic acid, Glycine, Histidine, Hydroxyproline, Isoleucine, Leucine, Lysine, Methionine, Phenylalanine, Proline, Serine, Threonine, Tryptophan, Tyrosine, Valine.

Thus a non-proteogenic amino acid is a moiety which can be incorporated into a peptide via peptide bonds but is not a proteogenic amino acid. Examples are γ-carboxyglutamate, ornithine, phosphoserine, the D-amino acids such as D-alanine and D-glutamine, Synthetic non-proteogenic amino acids comprise amino acids manufactured by chemical synthesis, i.e. D-isomers of the amino acids encoded by the genetic code such as D-alanine and D-leucine, Aib (α-aminoisobutyric acid), Abu (a-aminobutyric acid), Tie (tert-butylglycine), 3-aminomethyl benzoic acid, anthranilic acid, des-amino-Histidine, the beta analogs of amino acids such as β-alanine etc. D-histidine, desamino-histidine, 2-amino-histidine, β-hydroxy-histidine, homohistidine, N$^α$-acetyl-histidine, α-fluoromethyl-histidine, α-methyl-histidine, 3-pyridylalanine, 2-pyridylalanine or 4-pyridylalanine, (1-amino-cyclopropyl) carboxylic acid, (1-amino-cyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid.

The amino acid sequence for GLP has been reported by several researchers (Lopez, L. C. et al., *Proc. Nat'l, Acad. Sci.,* USA 80, 5485-5489, 1983; Bell, G. I., et al., *Nature* 302:716-718(1983); Heinrich, G., et al, *Endocrinol,* 115: 2176-2181(1984). The structure of the proproglucagon mRNA and its corresponding amino acid sequence is well know. The proteolysis processing of the precursor gene product, proglucagon, into glucagons and the two insulinotropic peptides has been characterized. As used herein, the notation of GLP-1 (1-37) refers to a GLP-1 polypeptide having all amino acids from 1 (N-terminus) through 37 (C-terminus). Similarly, GLP-1 (7-37) refers to a GLP-1 polypeptide having all amino acids from 7 (N-terminus) through 37 (C-terminus). Similarly, GLP-1(7-36) refers to a GLP-1 polypeptide having all amino acids from number7 (N-terminus) Through number 36 (C-terminus).

Also provided by the present invention are pharmaceutical compositions comprising a compound of the present invention in combination with one or more pharmaceutically acceptable carriers, diluents, or excipeints.

The principle of the solid phase synthesis of polypeptides are well known in the art and may be found in general texts in the area such as Dugas, H. and Penney, C., *Bioorganic Chemistry* (1981) Springer-Verlag, New York, page 54-92; Merrifield, J. M., *Chem. Soc.,* 85, 2149, 1962, and Stewart and Young, Solid Phase Peptide Synthesis, page 24-66, Freeman (San Francisco, 1969).

For example, a peptide fragment of the invention may be synthesized by solid phase methodology utilizing a Applied Biosystems 430 peptide synthesizer (Applied Biosystems, Inc., 850 Lincoln Centre Drive, Foster City, Calif. 94404) and synthesis cycles supplied by Applied Biosystems. Boc protected amino acids and other reagents are commercially available from Applied Biosystems and other chemical venders. Sequential Boc chemistry using double couple protocols are applied to the starting p-methyl benzhydryl amine resins for the production of C-terminal carboxamides. For the production of C-terminal acids, the corresponding PAM resin can be used. Asp, Gln and Arg are coupled using preformed hydroxyl benzotriazole esters.

Another object of the present invention is to provide a pharmaceutical formulation comprising a compound according to the present invention which is present in a concentration from 0.1 mg/ml to 25 mg/ml, and wherein said formulation has a pH from 3.0 to 9.0. The formulation may further comprise a buffer system, preservative(s), tonicity agent(s), chelating agent(s), stabilizers and surfactants. In one embodiment of the invention the pharmaceutical formulation is an aqueous formulation, i.e. formulation comprising water. Such formulation is typically a solution or a suspension. In a further embodiment of the invention the pharmaceutical formulation is an aqueous solution. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In another embodiment the pharmaceutical formulation is a freeze-dried formulation, whereto the physician or the patient adds solvents and/or diluents prior to use.

In another embodiment the pharmaceutical formulation is a dried formulation (e.g. freeze-dried or spray-dried) ready for use without any prior dissolution.

In a further aspect the invention relates to a pharmaceutical formulation comprising an aqueous solution of a compound according to the present invention, and a buffer, wherein said compound is present in a concentration from 0.1 mg/ml or above, and wherein said formulation has a pH from about 3.0 to about 9.0. In another embodiment of the invention the pH of the formulation is from about 7.0 to about 9.5. In another embodiment of the invention the pH of the formulation is from about 3.0 to about 7.0. In another embodiment of the invention the pH of the formulation is from about 5.0 to about 7.5. In another embodiment of the invention the pH of the formulation is from about 7.5 to about 9.0. In another embodiment of the invention the pH of the formulation is from about 7.5 to about 8.5. In another embodiment of the invention the pH of the formulation is from about 6.0 to about 7.5.

In another embodiment of the invention the pH of the formulation is from about 6.0 to about 7.0. In another embodiment the pharmaceutical formulation is from 8.0 to 8.5.

In a further embodiment of the invention the buffer is selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof. Each one of these specific buffers constitutes an alternative embodiment of the invention.

In a further embodiment of the invention the formulation further comprises a pharmaceutically acceptable preservative. In a further embodiment of the invention the preservative is selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3p-chlorphenoxypropane-1, 2-diol) or mixtures thereof. In an embodiment the preservative is phenol or m-cresol. In a further embodiment of the invention the preservative is present in a concentration from 0.1 mg/ml to 20 mg/ml. In a further embodiment of the invention the preservative is present in a concentration from 0.1 mg/ml to 5 mg/ml. In a further embodiment of the invention the preservative is present in a concentration from 5 mg/ml to 10 mg/ml. In a further embodiment of the invention the preservative is present in a concentration from 10 mg/ml to 20 mg/ml. Each one of these specific preservatives constitutes an alternative embodiment of the invention. The use of a preservative in pharmaceutical compositions is well-known to the skilled person. For convenience reference is made to Remington: The Science and Practice of Pharmacy, 19$^{th}$ edition, 1995.

In a further embodiment of the invention the formulation further comprises an isotonic agent. In a further embodiment of the invention the isotonic agent is selected from the group consisting of a salt (e.g. sodium chloride), a sugar or sugar alcohol, an amino acid (e.g. L-glycine, L-histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), or mixtures thereof. In an embodiment the isotoncity agent is propyleneglycol. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, soluble starch, hydroxyethyl starch and carboxymethyl-cellulose-Na may be used. In one embodiment the sugar additive is sucrose. Sugar alcohol is defined as a C4-C8 hydrocarbon having at least one —OH group and includes, for example, mannitol, sorbitol, inositol, galactitol, dulcitol, xylitol, and arabitol. In one embodiment the sugar alcohol additive is mannitol. The sugars or sugar alcohols mentioned above may be used individually or in combination. There is no fixed limit to the amount used, as long as the sugar or sugar alcohol is soluble in the liquid preparation and does not adversely effect the stabilizing effects achieved using the methods of the invention. In one embodiment, the sugar or sugar alcohol concentration is between about 1 mg/ml and about 150 mg/ml. In a further embodiment of the invention the isotonic agent is present in a concentration from 1 mg/ml to 50 mg/ml. In a further embodiment of the invention the isotonic agent is present in a concentration from 1 mg/ml to 7 mg/ml. In an embodiment of the invention the isotonic agent is present in a concentration from 5 mg/ml to 7 mg/ml. In a further embodiment of the invention the isotonic agent is present in a concentration from 8 mg/ml to 24 mg/ml. In a further embodiment of the invention the isotonic agent is present in a concentration from 25 mg/ml to 50 mg/ml. Each one of these specific isotonic agents constitutes an alternative embodiment of the invention. The use of an isotonic agent in pharmaceutical compositions is well-known to the skilled person. For convenience reference is made to Remington: The Science and Practice of Pharmacy, 19$^{th}$ edition, 1995.

In a further embodiment of the invention the formulation further comprises a chelating agent. In a further embodiment of the invention the chelating agent is selected from salts of ethylenediaminetetraacetic acid (EDTA), citric acid, and aspartic acid, and mixtures thereof. In a further embodiment of the invention the chelating agent is present in a concentration from 0.1 mg/ml to 5 mg/ml. In a further embodiment of the invention the chelating agent is present in a concentration from 0.1 mg/ml to 2 mg/ml. In a further embodiment of the invention the chelating agent is present in a concentration from 2 mg/ml to 5 mg/ml. Each one of these specific chelating agents constitutes an alternative embodiment of the invention. The use of a chelating agent in pharmaceutical compositions is well-known to the skilled person. For convenience reference is made to Remington: The Science and Practice of Pharmacy, 19$^{th}$ edition, 1995.

In a further embodiment of the invention the formulation further comprises a stabilizer. The use of a stabilizer in pharmaceutical compositions is well-known to the skilled person. For convenience reference is made to Remington: The Science and Practice of Pharmacy, 19$^{th}$ edition, 1995.

More particularly, compositions of the invention are stabilized liquid pharmaceutical compositions whose therapeutically active components include a polypeptide that possibly exhibits aggregate formation during storage in liquid pharmaceutical formulations. By "aggregate formation" is intended a physical interaction between the polypeptide molecules that results in formation of oligomers, which may remain soluble, or large visible aggregates that precipitate from the solution. By "during storage" is intended a liquid pharmaceutical composition or formulation once prepared, is not immediately administered to a subject. Rather, following preparation, it is packaged for storage, either in a liquid form, in a frozen state, or in a dried form for later reconstitution into a liquid form or other form suitable for administration to a subject. By "dried form" is intended the liquid pharmaceutical composition or formulation is dried either by freeze drying (i.e., lyophilization; see, for example, Williams and Polli (1984) J. Parenteral Sci. Technol. 38:48-59), spray drying (see Masters (1991) in Spray-Drying Handbook (5th ed; Longman Scientific and Technical, Essex, U.K.), pp. 491-676; Broadhead et al. (1992) Drug Devel. Ind. Pharm. 18:1 169-1206; and Mumenthaler et al. (1994) Pharm. Res. 1 1 :12-20), or air drying (Carpenter and Crowe (1988) Cryobiology 25:459-470; and Roser (1991) Biopharm. 4:47-53). Aggregate formation by a polypeptide during storage of a liquid pharmaceutical composition can adversely affect biological activity of that polypeptide, resulting in loss of therapeutic efficacy of the pharmaceutical composition. Furthermore, aggregate formation may cause other problems such as blockage of tubing, membranes, or pumps when the polypeptide-containing pharmaceutical composition is administered using an infusion system.

The pharmaceutical compositions of the invention may further comprise an amount of an amino acid base sufficient to decrease aggregate formation by the polypeptide during storage of the composition. By "amino acid base" is intended an amino acid or a combination of amino acids, where any given amino acid is present either in its free base form or in its salt form. Where a combination of amino acids is used, all of the amino acids may be present in their free base forms, all may be present in their salt forms, or some may be present in their free base forms while others are present in their salt forms. In one embodiment, amino acids to use in preparing the compositions of the invention are those carrying a charged side chain, such as arginine, lysine, aspartic acid, and glutamic acid. Any stereoisomer (i.e., L, D, or a mixture thereof) of a particular amino acid (e.g. methionine, histidine, imidazole, arginine, lysine, isoleucine, aspartic acid, tryptophan, threonine and mixtures thereof) or combinations of these stereoisomers, may be present in the pharmaceutical compositions of the invention so long as the particular amino acid is present either in its free base form or its salt form. In one embodiment the L-stereoisomer is used. Compositions of the invention may also be formulated with analogues of these amino acids. By "amino acid analogue" is intended a derivative of the naturally occurring amino acid that brings about the desired effect of decreasing aggregate formation by the polypeptide during storage of the liquid pharmaceutical compositions of the invention. Suitable arginine analogues include, for example, aminoguanidine, ornithine and N-monoethyl L-arginine, suitable methionine analogues include ethionine and buthionine and suitable cysteine analogues include S-methyl-L cysteine. As with the other amino acids, the amino acid analogues are incorporated into the compositions in either their free base form or their salt form. In a further embodiment of the invention the amino acids or amino acid analogues are used in a concentration, which is sufficient to prevent or delay aggregation of the protein. In a further embodiment of the invention methionine (or other sulphuric amino acids or amino acid analogous) may be added to inhibit oxidation of methionine residues to methionine sulfoxide when the polypeptide acting as the therapeutic agent is a polypeptide comprising at least one methionine residue susceptible to such oxidation. By "inhibit" is intended minimal accumulation of methionine oxidized species over time. Inhibiting methionine oxidation results in greater retention of the polypeptide in its proper molecular form. Any stereoisomer of methionine (L or D) or combinations thereof can be used. The amount to be added should be an amount sufficient to inhibit oxidation of the methionine residues such that the amount of methionine sulfoxide is acceptable to regulatory agencies. Typically, this means that the composition contains no more than about 10% to about 30% methionine sulfoxide. Generally, this can be achieved by adding methionine such that the ratio of methionine added to methionine residues ranges from about 1 :1 to about 1000:1, such as 10:1 to about 100:1.

In a further embodiment of the invention the formulation further comprises a stabilizer selected from the group of high molecular weight polymers or low molecular compounds. In a further embodiment of the invention the stabilizer is selected from polyethylene glycol (e.g. PEG 3350), polyvinyl alcohol (PVA), polyvinylpyrrolidone, carboxy-/hydroxycellulose or derivates thereof (e.g. HPC, HPC-SL, HPC-L and HPMC), cyclodextrins, sulphur-containing substances as monothioglycerol, thioglycolic acid and 2-methylthioethanol, and different salts (e.g. sodium chloride). Each one of these specific stabilizers constitutes an alternative embodiment of the invention.

The pharmaceutical compositions may also comprise additional stabilizing agents, which further enhance stability of a therapeutically active polypeptide therein. Stabilizing agents of particular interest to the present invention include, but are not limited to, methionine and EDTA, which protect the polypeptide against methionine oxidation, and a non-ionic surfactant, which protects the polypeptide against aggregation associated with freeze-thawing or mechanical shearing.

In a further embodiment of the invention the formulation further comprises a surfactant. In another embodiment of the invention the pharmaceutical composition comprises two different surfactants. The term "Surfactant" as used herein refers to any molecules or ions that are comprised of a water-soluble (hydrophilic) part, the head, and a fat-soluble (lipophilic) segment. Surfactants accumulate preferably at interfaces, which the hydrophilic part is orientated towards the water (hydrophilic phase) and the lipophilic part towards the oil- or hydrophobic phase (i.e. glass, air, oil etc.). The concentration at which surfactants begin to form micelles is known as the critical micelle concentration or CMC. Furthermore, surfactants lower the surface tension of a liquid. Surfactants are also known as amphipathic compounds. The term "Detergent" is a synonym used for surfactants in general.

Anionic surfactants may be selected from the group of: Chenodeoxycholic acid, Chenodeoxycholic acid sodium salt, Cholic acid, Dehydrocholic acid, Deoxycholic acid, Deoxycholic acid methyl ester, Digitonin, Digitoxigenin, N,N-Dimethyldodecylamine N-oxide, Docusate sodium, Glycochenodeoxycholic acid sodium, Glycocholic acid hydrate, Glycodeoxycholic acid monohydrate, Glycodeoxycholic acid sodium salt, Glycodeoxycholic acid sodium salt, Glycolithocholic acid 3-sulfate disodium salt, Glycolithocholic acid ethyl ester, N-Lauroylsarcosine sodium salt, N-Lauroylsarcosine sodium salt, N-Lauroylsarcosine, N-Lauroylsarcosine, Lithium dodecyl sulfate, Lugol, 1-Octanesulfonic acid sodium salt, 1-Octanesulfonic acid sodium salt, Sodium 1-butanesulfonate, Sodium 1-decanesulfonate, Sodium 1-dodecanesulfonate, Sodium 1-heptanesulfonate, Sodium 1-heptanesulfonate, Sodium 1-nonanesulfonate, Sodium 1-propanesulfonate monohydrate, Sodium 2- bromoethanesulfonate, Sodium cholate hydrate, ox or sheep bile, Sodium cholate hydrate, Sodium choleate, Sodium deoxycholate, Sodium dodecyl sulfate, Sodium dodecyl sulfate, Sodium hexanesulfonate, Sodium octyl sulfate, Sodium pentanesulfonate, Sodium taurocholate, Taurochenodeoxycholic acid sodium salt, Taurodeoxycholic acid sodium salt monohydrate, Taurolithocholic acid 3-sulfate disodium salt, Tauroursodeoxycholic acid sodium salt, Trizma® dodecyl sulfate, DSS (docusate sodium, CAS registry no. [577-11-7]), docusate calcium, CAS registry no. [128-49-4]), docusate potassium, CAS registry no. [7491-09-0]), SDS (sodium dodecyl sulfate or sodium lauryl sulfate), Dodecylphosphocholine (FOS- Choline-12), Decylphosphocholine (FOS-Choline-10), Nonylphosphocholine (FOS-Choline-9), dipalmitoyl phosphatidic acid, sodium caprylate, and/or Ursodeoxycholic acid.

Cationic surfactants may be selected from the group of: Alkyltrimethylammonium bromide Benzalkonium chloride, Benzalkonium chloride, Benzyldimethylhexadecylammonium chloride, Benzyldimethyltetradecylammonium chloride, Benzyltrimethylammonium tetrachloroiodate, Dimethyldioctadecylammonium bromide, Dodecylethyldimethylammonium bromide, Dodecyltrimethylammonium bromide, Dodecyltrimethylammonium bromide, Ethylhexadecyldimethylammonium bromide, Hexadecyltrimethylammonium bromide, Hexadecyltrimethylammonium bromide, Polyoxyethylene(10)-N-tallow-1, 3-diaminopropane, Thonzonium bromide, and/or Trimethyl (tetradecyl)ammonium bromide.

Nonionic surfactants may be selected from the group of: BigCHAP, Bis(polyethylene glycol bispmidazoyl carbonyl]), block copolymers as polyethyl- eneoxide/polypropyleneoxide block copolymers such as poloxamers, poloxamer 188 and poloxamer 407, Brij® 35, Brij® 56, Brij® 72, Brij® 76, Brij® 92V, Brij® 97, Brij® 58P, Cremophor® EL, Decaethylene glycol monododecyl ether, N-Decanoyl-N-methyl-glucamine, n-Dodecanoyl-N-methylglucamide, alkyl-polyglucosides, ethoxylated castor oil, Heptaethylene glycol monodecyl ether, Heptaethylene glycol monododecyl ether, Heptaethylene glycol monotetradecyl ether, Hexaethylene glycol monododecyl ether, Hexaethylene glycol monohexadecyl ether, Hexaethylene glycol monooctadecyl ether, Hexaethylene glycol monotetradecyl ether, lgepal CA-630, lgepal CA-630, Methyl-6-0-(N- heptylcarbamoyl)-beta-D-glucopyranoside, Nonaethylene glycol monododecyl ether, N- Nonanoyl-N-methylglucamine, N-Nonanoyl-N-methylglucamine, Octaethylene glycol monodecyl ether, Octaethylene glycol monododecyl ether, Octaethylene glycol monohexadecyl ether, Octaethylene glycol monooctadecyl ether, Octaethylene glycol monotetradecyl ether, Octyl-β-D-glucopyranoside, Pentaethylene glycol monodecyl ether, Pentaethylene glycol monododecyl ether, Pentaethylene glycol monohexadecyl ether, Pentaethylene glycol monohexyl ether, Pentaethylene glycol monooctadecyl ether, Pentaethylene glycol monooctyl ether, Polyethylene glycol diglycidyl ether, Polyethylene glycol ether W-1, Polyoxyethylene 10 tridecyl ether, Polyoxyethylene 100 stearate, Polyoxyethylene 20 isohexadecyl ether, Polyoxyethylene 20 oleyl ether, Polyoxyethylene 40 stearate, Polyoxyethylene 50 stearate, Polyoxyethylene 8 stearate, Polyoxyethylene bis(imidazolyl carbonyl), Polyoxyethylene 25 propylene glycol stearate, Saponin from Quillaja bark, Span® 20, Span® 40, Span® 60, Span® 65, Span® 80, Span® 85, Tergitol, Type 15-S-12, Tergitol, Type 15-S-30, Tergitol, Type 15-S-5, Tergitol, Type 15-S-7, Tergitol, Type 15-S-9, Tergitol, Type NP-10, Tergitol, Type NP-4, Tergitol, Type NP-40, Tergitol, Type NP-7, Tergitol, Type NP-9, Tetradecyl-β-D-maltoside, Tetraethylene glycol monodecyl ether, Tetraethylene glycol monododecyl ether, Tetraethylene glycol monotetradecyl ether, Triethylene glycol monodecyl ether, Triethylene glycol monododecyl ether, Triethylene glycol monohexadecyl ether, Triethylene glycol monooctyl ether, Triethylene glycol monotetradecyl ether, Triton CF-21, Triton CF-32, Triton DF-12, Triton DF-16, Triton GR-5M, Triton QS-15, Triton QS-44, Triton X-100, Triton X-102, Triton X-15, Triton X-151, Triton X-200, Triton X- 207, Triton® X-100, Triton® X-114, Triton® X-165 solution, Triton® X-305 solution, Triton® X- 405, Triton® X-45, Triton® X-705-70, TWEEN® 20, TWEEN® 40, TWEEN® 60, TWEEN® 6, TWEEN® 65, TWEEN® 80, TWEEN® 81, TWEEN® 85, Tyloxapol, sphingophospholipids (sphingomyelin), and sphingoglycolipids (ceramides, gangliosides), phospholipids, and/or n- Undecyl β-D-glucopyranoside.

Zwitterionic surfactants may be selected from the group of: CHAPS, CHAPSO, 3-(Decyldimethylammonio)propanesulfonate inner salt, 3-(Dodecyldimethylammonio)-propanesulfonate inner salt, 3-(Dodecyldimethylammonio) propanesulfonate inner salt, 3 -(N,N-Dimethylmyristylammonio)propanesulfonate, 3-(N,N-Dimethyloctadecyl-ammonio)-propanesulfonate, 3-(N,N-Dimethyloctylammonio)propanesulfonate inner salt, 3-(N, N-Dimethylpalmitylammonio)propanesulfonate, N-alkyl-N, N-dimethylammonio-1-propanesulfonates, 3-cholamido-l-propyldimethylammonio-1-propanesulfonate, Dodecylphosphocholine, myristoyl lysophosphatidylcholine, Zwittergent 3-12 (N-dodecyl- N, N-dimethyl-3-ammonio-l-propanesulfonate), Zwittergent 3-10 (3-(Decyldimethylammonio)-propanesulfonate inner salt), Zwittergent 3-08 (3-(Octyldimethylammonio)pro-panesulfonate), glycerophospholipids (lecithins, kephalins, phosphatidyl serine), glyceroglycolipids (galactopyranoside), alkyl, alkoxyl (alkyl ester), alkoxy (alkyl ether)-derivatives of lysophosphatidyl and phosphatidylcholines, e.g. lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, lysophosphatidylserine and lysophosphatidylthreonine, acylcarnitines and derivatives, $N^{beta}$-acylated derivatives of lysine, arginine or histidine, or side-chain acylated derivatives of lysine or arginine, $N^{beta}$-acylated derivatives of dipeptides comprising any combination of lysine, arginine or histidine and a neutral or acidic amino acid, $N^{beta}$-acylated derivative of a tripeptide comprising any combination of a neutral amino acid and two charged amino acids, or the surfactant may be selected from the group of imidazoline derivatives, long-chain fatty acids and salts thereof $C_6$-$C_{12}$ (eg. oleic acid and caprylic acid), N-Hexadecyl-N,N-dimethyl-3-ammonio-1-propanesulfonate, anionic (alkyl-aryl-sulphonates) monovalent surfactants, palmitoyl lysophosphatidyl-L-serine, lysophospholipids (e.g. 1-acyl-sn-glycero-3-phosphate esters of ethanolamine, choline, serine or threonine), or mixtures thereof The term "alkyl-polyglucosides" as used herein in relates to an straight or branched $C_{5-20}$-alkyl, -alkenyl or -alkynyl chain which is substituted by one or more glucoside moieties such as maltoside, saccharide etc. Embodiments of these alkyl-polyglucosides include $C_{6-18}$ alkyl-polyglucosides. Specific embodiments of these alkyl-polyglucosides includes the even numbered carbon-chains such as $C_6$, $C_8$, $C_{10}$, $C_{12}$, $C_{14}$, $C_{16}$, $C_{18}$ and $C_{20}$ alkyl chain. Specific embodiments of the glucoside moieties include pyranoside, glucopyranoside, maltoside, maltotrioside and sucrose. In embodiments of the invention less than 6 glucosid moieties are attached to the alkyl group. In embodiments of the invention less than 5 glucosid moieties are attached to the alkyl group. In embodiments of the invention less than 4 glucosid moieties are attached to the alkyl group. In embodiments of the invention less than 3 glucosid moieties are attached to the alkyl group. In embodiments of the invention less than 2 glucosid moieties are attached to the alkyl group. Specific embodiments of alkyl- polyglucosides are alkyl glucosides such n-decyl β-D-glucopyranoside, decyl β-D-maltopyranoside, dodecyl β-D-glucopyranoside, n-dodecyl β-D-maltoside, n-dodecyl β-D- maltoside, n-dodecyl β-D-maltoside, tetradecyl β-D-glucopyranoside, decyl β-D- maltoside, hexadecyl β-D-maltoside, decyl β-D-maltotrioside, dodecyl β-D-maltotrioside, tetradecyl β-D-maltotrioside, hexadecyl β-D-maltotrioside, n-dodecyl-sucrose, n-decyl-sucrose, sucrose monocaprate, sucrose monolaurate, sucrose monomyristate, and sucrose monopalmitate. The use of a surfactant in pharmaceutical compositions is well-known to the skilled person. For convenience reference is made to Remington: The Science and Practice of Pharmacy, 19$^{th}$ edition, 1995.

In a further embodiment of the invention the formulation further comprises protease inhibitors such as EDTA (ethylenediamine tetraacetic acid) and benzamidineHCI, but other commercially available protease inhibitors may also be used. The use of a protease inhibitor is particular useful in pharmaceutical compositions comprising zymogens of proteases in order to inhibit autocatalysis.

It is possible that other ingredients may be present in the peptide pharmaceutical formulation of the present invention. Such additional ingredients may include wetting agents, emulsifiers, antioxidants, bulking agents, tonicity modifiers, chelating agents, metal ions, oleaginous vehicles, proteins (e.g., human serum albumin, gelatine or proteins) and a zwitterion (e.g., an amino acid such as betaine, taurine, arginine, glycine, lysine and histidine). Such additional ingredients, of course, should not adversely affect the overall stability of the pharmaceutical formulation of the present invention.

Pharmaceutical compositions containing a compound according to the present invention may be administered to a patient in need of such treatment at several sites, for example, at topical sites, for example, skin and mucosal sites, at sites which bypass absorption, for example, administration in an artery, in a vein, in the heart, and at sites which involve absorption, for example, administration in the skin, under the skin, in a muscle or in the abdomen.

Administration of pharmaceutical compositions according to the invention may be through several routes of administration, for example, lingual, sublingual, buccal, in the mouth, oral, in the stomach and intestine, nasal, pulmonary, for example, through the bronchioles and alveoli or a combination thereof, epidermal, dermal, transdermal, vaginal, rectal, ocular, for examples through the conjunctiva, uretal, and parenteral to patients in need of such a treatment.

Compositions of the current invention may be administered in several dosage forms, for example, as solutions, suspensions, emulsions, microemulsions, multiple emulsion, foams, salves, pastes, plasters, ointments, tablets, coated tablets, rinses, capsules, for example, hard gelatine capsules and soft gelatine capsules, suppositories, rectal capsules, drops, gels, sprays, powder, aerosols, inhalants, eye drops, ophthalmic ointments, ophthalmic rinses, vaginal pessaries, vaginal rings, vaginal ointments, injection solution, in situ transforming solutions, for example in situ gelling, in situ setting, in situ precipitating, in situ crystallization, infusion solution, and implants. Compositions of the invention may further be compounded in, or attached to, for example through covalent, hydrophobic and electrostatic interactions, a drug carrier, drug delivery system and advanced drug delivery system in order to further enhance stability of the compound of the present invention, increase bioavailability, increase solubility, decrease adverse effects, achieve chronotherapy well known to those skilled in the art, and increase patient compliance or any combination thereof. Examples of carriers, drug delivery systems and advanced drug delivery systems include, but are not limited to, polymers, for example cellulose and derivatives, polysaccharides, for example dextran and derivatives, starch and derivatives, polyvinyl alcohol), acrylate and methacrylate polymers, polylactic and polyglycolic acid and block co-polymers thereof, polyethylene glycols, carrier proteins, for example albumin, gels, for example, thermogelling systems, for example block co-polymeric systems well known to those skilled in the art, micelles, liposomes, microspheres, nanoparticulates, liquid crystals and dispersions thereof, L2 phase and dispersions there of, well known to those skilled in the art of phase behaviour in lipid-water systems, polymeric micelles, multiple emulsions, self-emulsifying, self-microemulsifying, cyclodextrins and derivatives thereof, and dendrimers.

Compositions of the current invention are useful in the formulation of solids, semisolids, powder and solutions for pulmonary administration of compounds of the present invention, using, for example a metered dose inhaler, dry powder inhaler and a nebulizer, all being devices well known to those skilled in the art. Compositions of the current invention are specifically useful in the formulation of controlled, sustained, protracting, retarded, and slow release drug delivery systems. More specifically, but not limited to, compositions are useful in formulation of parenteral controlled release and sustained release systems (both systems leading to a many-fold reduction in number of administrations), well known to those skilled in the art. Even more preferably, are controlled release and sustained release systems administered subcutaneous. Without limiting the scope of the invention, examples of useful controlled release system and compositions are hydrogels, oleaginous gels, liquid crystals, polymeric micelles, microspheres, nanoparticles, Methods to produce controlled release systems useful for compositions of the current invention include, but are not limited to, crystallization, condensation, co-crystallization, precipitation, co-precipitation, emulsification, dispersion, high pressure homogenisation, encapsulation, spray drying, microencapsulating, coacervation, phase separation, solvent evaporation to produce microspheres, extrusion and supercritical fluid processes. General reference is made to Handbook of Pharmaceutical Controlled Release (Wise, D. L., ed. Marcel Dekker, New York, 2000) and Drug and the Pharmaceutical Sciences vol. 99: Protein Formulation and Delivery (MacNally, E. J., ed. Marcel Dekker, New York, 2000). Parenteral administration may be performed by subcutaneous, intramuscular, intraperitoneal or intravenous injection by means of a syringe, optionally a pen-like syringe. Alternatively, parenteral administration can be performed by means of an infusion pump. A further option is a composition which may be a solution or suspension or a powder for the administration of the compound of the present invention in the form of a nasal or pulmonal liquid or powder spray. As a still further option, the pharmaceutical compositions containing the compound of the invention can also be adapted to transdermal administration, e.g. by needle-free injection or from a patch, optionally an iontophoretic patch, or transmucosal, e.g. buccal, administration. The compounds of the present invention can be administered via the pulmonary route in a vehicle, as a solution, suspension or dry powder using any of known types of devices suitable for pulmonary drug delivery. Examples of these comprise, but are not limited to, the three general types of aerosol-generating for pulmonary drug delivery, and may include jet or ultrasonic nebulizers, metered- dose inhalers, or dry powder inhalers (Cf. Yu J, Chien Y W. Pulmonary drug delivery: Physiologic and mechanistic aspects. Crit Rev Ther Drug Carr Sys 14(4) (1997) 395-453).

Based on standardised testing methodology, the aerodynamic diameter ($d_a$) of a particle is defined as the geometric equivalent diameter of a reference standard spherical particle of unit density (1 g/cm$^3$). In the simplest case, for spherical particles, $d_a$ is related to a reference diameter (d) as a function of the square root of the density ratio as described by: Modifications to this relationship occur for non-spherical particles (cf. Edwards D A, Ben-Jebria A, Langer R. Recent advances in pulmonary drug delivery using large, porous inhaled particles. J Appl Physiol 84(2) (1998) 379-385). The terms "MMAD" and "MMEAD" are well- described and known to the art (cf . Edwards D A, Ben-Jebria A, Langer R and represents a measure of the median value of an aerodynamic particle size distribution. Recent advances in pulmonary drug delivery using large, porous inhaled particles. J Appl Physiol 84(2) (1998) 379-385). Mass median aerodynamic diameter (MMAD) and mass median effective aerodynamic diameter (MMEAD) are used inter-changeably, are statistical parameters, and empirically describe the size of aerosol particles in relation to their potential to deposit in the lungs, independent of actual shape, size, or density (cf. Edwards D A, Ben-Jebria A, Langer R. Recent advances in pulmonary drug delivery using large, porous inhaled particles. J Appl Physiol 84(2) (1998) 379-385). MMAD is normally calculated from the measurement made with impactors, an instrument that measures the particle inertial behaviour in air. In a further embodiment, the formulation could be aerosolized by any known aerosolisation technology, such as nebulisation, to achieve a MMAD of aerosol particles less than 10 more preferably between 1 -5 µm, and most preferably between 1 -3 µm. The preferred particle size is based on the most effective size for delivery of drug to the deep lung, where protein is optimally absorbed (cf . Edwards D A, Ben-Jebria A, Langer A, Recent advances in pulmonary drug delivery using large, porous inhaled particles. J Appl Physiol 84(2) (1998) 379-385).

Deep lung deposition of the pulmonal formulations comprising the compound of the present invention may optional be further optimized by using modifications of the inhalation techniques, for example, but not limited to: slow inhalation flow (eg. 30 L/min), breath holding and timing of actuation.

The term "stabilized formulation" refers to a formulation with increased physical stability, increased chemical stability or increased physical and chemical stability.

The term "physical stability" of the protein formulation as used herein refers to the tendency of the protein to form biologically inactive and/or insoluble aggregates of the protein as a result of exposure of the protein to thermo-mechanical stresses and/or interaction with interfaces and surfaces that are destabilizing, such as hydrophobic surfaces and interfaces. Physical stability of the aqueous protein formulations is evaluated by means of visual inspection and/or turbidity measurements after exposing the formulation filled in suitable containers (e.g. cartridges or vials) to mechanical/physical stress (e.g. agitation) at different temperatures for various time periods. Visual inspection of the formulations is performed in a sharp focused light with a dark background. The turbidity of the formulation is characterized by a visual score ranking the degree of turbidity for instance on a scale from 0 to 3 (a formulation showing no turbidity corresponds to a visual score 0, and a formulation showing visual turbidity in daylight corresponds to visual score 3). A formulation is classified physical unstable with respect to protein aggregation, when it shows visual turbidity in daylight. Alternatively, the turbidity of the formulation can be evaluated by simple turbidity measurements well-known to the skilled person. Physical stability of the aqueous protein formulations can also be evaluated by using a spectroscopic agent or probe of the conformational status of the protein. The probe is preferably a small molecule that preferentially binds to a non-native conformer of the protein. One example of a small molecular spectroscopic probe of protein structure is Thioflavin T. Thioflavin T is a fluorescent dye that has been widely used for the detection of amyloid fibrils. In the presence of fibrils, and perhaps other protein configurations as well, Thioflavin T gives rise to a new excitation maximum at about 450 nm and enhanced emission at about 482 nm when bound to a fibril protein form. Unbound Thioflavin T is essentially non-fluorescent at the wavelengths.

Other small molecules can be used as probes of the changes in protein structure from native to non-native states. For instance the "hydrophobic patch" probes that bind preferentially to exposed hydrophobic patches of a protein. The hydrophobic patches are generally buried within the tertiary structure of a protein in its native state, but become exposed as a protein begins to unfold or denature. Examples of these small molecular, spectroscopic probes are aromatic, hydrophobic dyes, such as antrhacene, acridine, phenanthroline or the like. Other spectroscopic probes are metal-amino acid complexes, such as cobalt metal complexes of hydrophobic amino acids, such as phenylalanine, leucine, isoleucine, methionine, and valine, or the like.

The term "chemical stability" of the protein formulation as used herein refers to chemical covalent changes in the protein structure leading to formation of chemical degradation products with potential less biological potency and/or potential increased immunogenic properties compared to the native protein structure. Various chemical degradation products can be formed depending on the type and nature of the native protein and the environment to which the protein is exposed. Elimination of chemical degradation can most probably not be completely avoided and increasing amounts of chemical degradation products is often seen during storage and use of the protein formulation as well-known by the person skilled in the art. Most proteins are prone to deamidation, a process in which the side chain amide group in glutaminyl or asparaginyl residues is hydrolysed to form a free carboxylic acid. Other degradations pathways involves formation of high molecular weight transformation products where two or more protein molecules are covalently bound to each other through transamidation and/or disulfide interactions leading to formation of covalently bound dimer, oligomer and polymer degradation products (Stability of Protein Pharmaceuticals, Ahem. T.J. & Manning M. C, Plenum Press, New York 1992). Oxidation (of for instance methionine residues) can be mentioned as another variant of chemical degradation. The chemical stability of the protein formulation can be evaluated by measuring the amount of the chemical degradation products at various time-points after exposure to different environmental conditions (the formation of degradation products can often be accelerated by for instance increasing temperature). The amount of each individual degradation product is often determined by separation of the degradation products depending on molecule size and/or charge using various chromatography techniques (e.g. SEC-HPLC and/or RP-HPLC).

Hence, as outlined above, a "stabilized formulation" refers to a formulation with increased physical stability, increased chemical stability or increased physical and chemical stability. In general, a formulation must be stable during use and storage (in compliance with recommended use and storage conditions) until the expiration date is reached.

In one embodiment of the invention the pharmaceutical formulation comprising the compound of the present invention is stable for more than 6 weeks of usage and for more than 3 years of storage.

In another embodiment of the invention the pharmaceutical formulation comprising the compound of the present invention is stable for more than 4 weeks of usage and for more than 3 years of storage. In a further embodiment of the invention the pharmaceutical formulation comprising the compound of the present invention is stable for more than 4 weeks of usage and for more than two years of storage.

In an even further embodiment of the invention the pharmaceutical formulation comprising the compound of the present invention is stable for more than 2 weeks of usage and for more than two years of storage.

In another aspect the present invention relates to the use of a compound according to the invention for the preparation of a medicament.

The present invention also includes salt form of GLP-1 analogs. A GLP-1 analog of the invention may be sufficiently acidic or sufficiently basic to react with any of a number of inorganic bases, and inorganic acids, to form a salt. Acids commonly employed to form acid addition salts are inorganic acid such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, benzoic acid, acetic acid, and the like. Examples of such salts include the sulfate, hydrosulfate, bisulfate, sulfite, bisulfate, phosphate, monohydrogenphosphate, dihydrogenphoephate, metaphosphate, pyrophosphate, chloride, bromide, iodide, propionate, decanoate, caprylate, acrylate, formate, isobutyrate, heptanoate, propiolate, oxalate, malonate, succinate, suberate, sebacate, fumarate, maleate, butyne-1, 4-dioate, hexyne-1, 6-dioate, benzoate, chlorobenzoate, methybenzoate, dinitrobenzoate, hydroxybenzoate, methoxybezoate, phthalate, sulfonate, xylenesulfonate, phenylacetate, phenylpropionate, phenylbutyrate, citrate, lactate, gamma-hydroxybutyrate, glycolate, tartrate, methaneeulfonate, propanesulfonate, naphthalene-1-sulfonate, naphthalene-2-sulfonate, mandelate, and the like. Preferred acid addition salts are those formed with mineral acids such as hydrochloric acid and hydrobromic acid, and, especially, hydrochloric acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, and the like. Salt forms of GLP-1 analogs are particularly preferred. Of course, when the compounds of this invention are used for therapeutic purposes, those compounds may also be in the form of a salt, but the salt must be pharmaceutically acceptable.

The modified GLP-1 analogs of the invention find multiple uses including use as a treatment for diabetes, a sedative, a treatment of nervous system disorders, use to induce an anxiolytic effect on the CNS, use to activate the CNS, use for post surgery treatment and as a treatment for insulin resistance.

A. Diabetes Treatments

The modified GLP-1 analogs of the invention generally will normalize hyperglycemia though glucose-dependent mechanisms. As such, the modified GLP-1 analogs are useful as primary agents for the treatment of type II diabetes mellitus and as adjunctive agents for the treatment of type I diabetes mellitus.

The use of an effective amount of the modified GLP-1 analogs as a treatment for diabetes mellitus has the advantage of being more potent than non modified GLP-1. Since the modified GLP-1 analogs are more stable in vivo, smaller amount of the molecule can be administered for effective treatment. Te present invention is especially suited for the treatment of patients with diabetes, both type I and type II, in that the action of the peptide is dependent on the glucose concentration of the blood, and thus the risk of hypoglycemic side effects are greatly reduced over the risks in using current methods of treatment.

The Present invention also provides for a method for treating diabetes mellitus in an individual, wherein said method comprises providing an amount of the modified GLP-1 analogs sufficient to treat diabetes; where the composition contains a modified GLP-1 analog.

B. Treatment of Nervous System Disorders

The modified GLP-1 analogs of the invention also find use as a sedative. In one aspect of the invention, there is provided a method of sedating a mammalian subject with an abnormality resulting in increased activation of the central or peripheral nervous system using the modified GLP-1 analogs to the subject in the an amount sufficient to produce a seductive or anxiolytic effect on the subject. The modified GLP-1 analogs may be administrated intracerebroventricularly, orally, subcutaneously, intramuscularly, or intravenously. Such methods are useful to treat or ameliorate nervous system conditions such as anxiety, movement disorder, aggression, psychosis, seizures, panic attacks, hysteria and sleep disorders.

In a related aspect, the invention encompasses a method of increasing the activity of a mammalian subject, comprising administering a modified GLP-1 analogs to the subject in an amount sufficient to produce and activating effect on the subject. Preferably, the subject has a condition resulting in decreased activation of the central or peripheral nervous system. The modified GLP-1 analogs find particular use in the treatment or amelioration of depression, schizoaffective disorders, sleep apnea, attention deficit syndrome with poor concentration, memory loss, forgetfulness, and narcolcpsy, to name a few conditions in which arousal of the central nervous system may be advantageous.

The modified GLP-1 analogs of the invention may be used to induce arousal for the treatment or amelioration of depression, schizoaffective disorders, sleep apnea, and attention deficit syndromes with poor concentration, memory loss, forgetfulness, and narcolepsy. The therapeutic efficacy of the modified GLP-1 analogs treatment may be monitored by patient interview to assess their condition, by psychological/neurological testing, or by amelioration of the symptoms associated with these conditions. For example, monitoring the occurrence of narcoleptic attacks may assess treatment of narcolepsy. As another example, effects of modified GLP-1 analogs on the ability of a subject to concentrate, or on memory capacity, may be tested using any of a number of diagnostic test well know to those of skill in art.

C. Posy Surgery Treatment

The modified GLP-1 analogs of the invention may be utilized for post surgery treatments. A patient is in need of the modified GLP-1 analogs of the present invention for about 1-16 hours before surgery is performed on the patient, during surgery on the patient, and after the patient's surgery for a period of not more than about 5 days.

The modified GLP-1 analogs of the present invention are administered from about sixteen hours to about one hour before surgery begins. The length of time before surgery when the compounds used in the present invention should be administered in order to reduce catabolic effects and insulin resistance is dependent on a number of factors. These factors are generally knows to the physician of ordinary skill, and include, most importantly, whether the patient is fasted or supplied with a glucose infusion or beverage, or some other form of sustenance during the preparatory period before surgery. Other important factors include the patient's sex weight and age, the severity of any inability to regulate blood glucose, the underlying causes of any inability to regulate blood glucose, the expected severity of the trauma caused by the surgery, the route of administration and bioavailability, the persistence in the body, the formulation, and the potency of the compounds. A preferred time interval within which to begin administration of the modified GLP-1 analogs used in the present invention is from about one hour to about ten hours before surgery beings. The most preferred interval to begin administration is between two hours and eight hours before surgery begins.

Insulin resistance following a particular type of surgery, elective abdominal surgery, is most profound on the first post-operative day, lasts at least five days and may take up to three weeks to normalize Thus, the post-operative patient may be in need of administration of the modified GLP-1 analogs used in the present invention for a period of time following the trauma of surgery that will depend on factors whether the patient is fasted or supplied with a glucose infusion or beverage, or some other form of sustenance following surgery, and also, without limitation, the patient's sex, weight and age, the severity of any inability to regulate blood glucose, the underlying causes of any inability to regulate blood glucose, the underlying causes of any inability to regulate blood glucose, the actual severity of the trauma caused by the surgery, the route of administration and bioavailability, the persistence in the body, the formulation, and the potency of the compound administered. The preferred duration of administration of the compounds used in the present invention is not more that five days following surgery.

D. Insulin Resistance Treatment

The modified GLP-1 analogs of the invention may be utilized to treat insulin resistance independently from there used in post surgery treatment. Insulin resistance may be due to decrease in binding of insulin to cell-surface receptors, or alterations in intracellular metabolism. The first type, characterized as a decrease in insulin sensitivity, can typically be overcome by increased insulin concentration. The second type, characterized by as a decrease in insulin responsiveness, cannot be overcome by large quantities of insulin. Insulin resistance following trauma can be overcome by doses of insulin that are proportional to the degree of insulin resistance, and thus is apparently caused by a decrease in insulin sensitivity.

The dose of modified GLP-1 analogs effective to normalize a patient's blood glucose level will depended on a number of factors, amount which are included, without limitation, the patient's sex, weight and age, the severity of inability to regulate blood glucose, the underlying causes of inability to regulate glucose, whether glucose, or another carbohydrate source, is simultaneously administered, the route of administration and bioavailability, the persistence in the body, the formulation, and the potency.

The ability of a GLP-1 analog to stimulate insulin secretion may be determined by providing a GLP-1 analog to cultured animal cells, such as the RIN-38 rat insulinoma cell line, and monitoring the release of immunoreactive insulin (IRI) into the media. Alternatively one can inject a GLP-1 analog into an animal and monitor plasma levels of immunoreactive insulin (IRI).

The presence of IRI is detected through the use of a radioimmunoassay, which can specifically detect insulin. Any radioimmunology assay capable of detecting the presence of IRI may be employed; one such assay is a modification of the method of Albano, J. D. M. et al., *Acta Endocrinol.*70: 487-509 (1972). In this modification, a phosphate/albumin buffer with a pH of 7.4 is employed. The incubation is prepared with consecutive addition of 500 µL of phosphate buffer, 50 µL of perfusate sample or rat Insulin standard in perfusate, 100 µL of anti-insulin antiserum (Wellcome Laboratories; 1:40,000 dilution), and 100 µL of [$^{125}$I] insulin, giving a total volume of 750 µL in a 10×75 mm disposable glass tube. After incubation for 2-3 days at 4° C., free insulin is separated from antibody-bound insulin by charcoal separation. The assay sensitivity is 1-2 uU/ml. In order to measure the release of IRI into the cell culture medium of cells grown in tissue culture, one preferably incorporates radioactive label into proinsulin. Although any radioactive label capable of labeling polypeptide can be used, it is preferable to use $^3$H leucine in order to obtain labeled proinsulin.

To determine whether a GLP-1 analog has insulinotropic properties may also be determined by pancreatic infusion. The in situ isolated perfused rat pancreas assay is a modification of the method of Penhos, J, C., et al., *Diabetes,* 18: 733-738 (1969). Fasted male Charles River strain albino rats, weighing 350-600 g, are anesthetized with an intraperitoneal injection of Amytal Sodium (Eli Lilly and Co, 160 ng/kg). Renal, adrenal, gastric, and lower colonic blood vessels are ligated. The entire intestine is resacted except for about four cm of duodenum and the descending colon and rectum. Therefore, only a small part of the intestine is perfused, minimizing possible interference by enteric substances with glucagons-like immunoreactivity. The perfusate is a modified Kreba-Ringer bicarbonate buffer with 4% dextran T70 and 0.2% bovine serum albumin (fraction V), and is bubbled with 95% $O_2$ and 5% $CO_2$. A nonpulsatile flow, 4-channel roller bearing pump (Buehler polystatic, Buehler Instruments Division, Nuclear-Chicago Corp) is used, and a switch from one perfusate source to another is accomplished by switching a 3-way stopcock. The manner in which perfusion is performed, monitored, and analyzed follow the method of Weir, G. C., et at. *J. Clin. Investigat.* 54: 1403-1412 (1974), which is hereby incorporated by reference.

The treatment with a compound according to the present invention may also be combined with a second or more pharmacologically active substances, e.g. selected from antidiabetic agents, antiobesity agents, appetite regulating agents, antihypertensive agents, agents for the treatment and/or prevention of complications resulting from or associated with diabetes and agents for the treatment and/or prevention of complications and disorders resulting from or associated with obesity. Examples of these pharmacologically active substances are : Insulin, sulphonylureas, biguanides, meglitinides, glucosidase inhibitors, glucagon antagonists, DPP-IV (dipeptidyl peptidase-IV) inhibitors, inhibitors of hepatic enzymes involved in stimulation of gluconeogenesis and/or glycogenosis, glucose uptake modulators, compounds modifying the lipid metabolism such as antihyperlipidemic agents as HMG CoA inhibitors (statins), Gastric Inhibitory Polypeptides (GIP analogs), compounds lowering food intake, RXR agonists and agents acting on the ATP-dependent potassium channel of the (3-cells; Cholestyramine, colestipol, clofibrate, gemfibrozil, lovastatin, pravastatin, simvastatin, probucol, dextrothyroxine, neteglinide, repaglinide; β-blockers such as alprenolol, atenolol, timolol, pindolol, propranolol and metoprolol, ACE (angiotensin converting enzyme) inhibitors such as benazepril, captopril, enalapril, fosinopril, lisinopril, alatriopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin; CART (cocaine amphetamine regulated transcript) agonists, NPY (neuropeptide Y) antagonists, PYY agonist, PYY2 agonists, PYY4 agonits, mixed PPY2/PYY4 agonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, (β3 agonists, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, RXR (retinoid X receptor) modulators, TR βagonists; histamine H3 antagonists, Gastric Inhibitory Polypeptide agonists or antagonists (GIP analogs), gastrin and gastrin analogs. The treatment with a compound according to this invention may also be combined with surgery—a surgery that influence the glucose levels and/or lipid homeostasis such as gastric banding or gastric bypass.

It should be understood that any suitable combination of the compounds according to the invention with one or more of the above-mentioned compounds and optionally one or more further pharmacologically active substances are considered to be within the scope of the present invention.

The present invention is further illustrated by the following examples which, however, are not to be construed as limiting the scope of protection. The features disclosed in the foregoing description and in the following examples may, both separately and in any combination thereof, be material for realising the invention in diverse forms thereof.

By way of illustration, the following examples are provided to help describe how to make and practice the various embodiments of the invention. These examples are in no way meant to limit the scope of the invention.

EXAMPLES

Abbreviations Used:
r.t: Room temperature;
DIPEA: diisopropylethylamine;
$H_2O$: water;
$CH_3CN$: acetonitrile;
DMF: N,N-dimethylformamide;
HBTU: 2-(1 H-Benzotriazol-1-yl-)-1, 1, 3, 3 tetramethyluronium hexafluorophosphate;
Fmoc: 9 H-fluoren-9-ylmethoxycarbonyl;
Boc: tert butyloxycarbonyl;
OtBu: tert butyl ester;
tBu: tert butyl Trt: triphenylmethyl;
Pmc: 2,2,5,7,8-Pentamethyl-chroman-6-sulfonyl;
Dde: 1-(4,4-Dimethyl-2,6-dioxocyclohexylidene)ethyl;
ivDde: 1-(4,4-Dimethyl-2,6-dioxocyclohexylidene)-3-methylbutyl;
Mtt: 4-methyltrityl;
Mmt: 4-methoxytrityl;
DCM: dichloromethane;
TIS: triisopropylsilane);
TFA: trifluoroacetic acid;
$Et_2O$: diethylether;
NMP: 1-Methyl-pyrrolidin-2-one;
HOAt: 1-Hydroxy-7-azabenzotriazole;
HOBt: 1-Hydroxybenzotriazole;
DIC: Diisopropylcarbodiimide.

Synthesis of Q

Q such as those of formula II are commercial available, known in the literature or may be conveniently prepared by a variety methods familiar to those skilled in the art. One common route for the synthesis of formula II wherein X, Y and $R_3$ are hydrogen that has been reported (S. Oishi etc., *J. Chem. Soc., Perkin Trans.* 1, 2001, 2445) is illustrated in Scheme 1.

Scheme 1

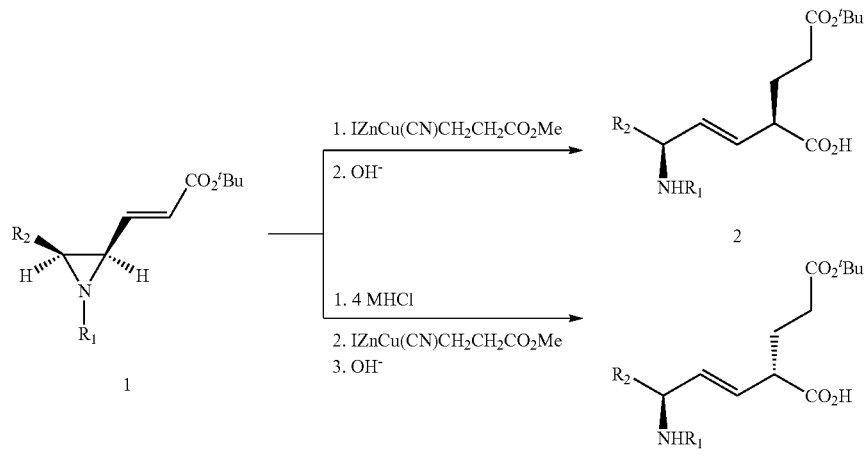

Q such as those of formula II are commercial available, known in the literature or may be conveniently prepared by a variety methods familiar to those skilled in the art. One common route for the synthesis of formula II wherein X is fluorine, Y and $R_3$ are hydrogen is illustrated in Scheme 2. The key starting material 4 is commercial available, known in literature (T. Narumi et al., *Tetrahedron*, 2008, 64, 4332).

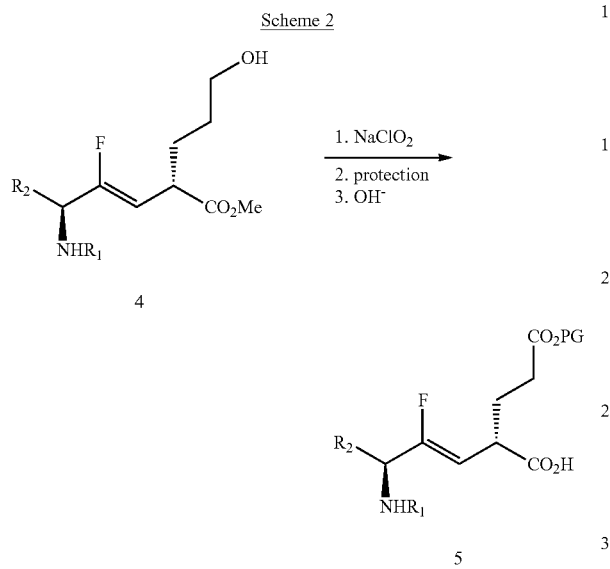

Q such as those of formula IIIa are commercial available, known in the literature or may be conveniently prepared by a variety methods familiar to those skilled in the art. One common route for the synthesis of formula III wherein X is trifuloromethyl, Z is nitrogen, Y, $R_1$, $R_2$ and $R_3$ are hydrogen is illustrated in Scheme 3. The key starting material 3, 3, 3-trifluorol-nitropropene 6 is commercial available, known in literature. Aza-Michael addition of glutamic acid diester to 3, 3, 3-trifluorol-nitropropene 6 in stereocontrolled fashion (M. Molteni et al., *Org. Lett.*, 2003, 5, 3887).

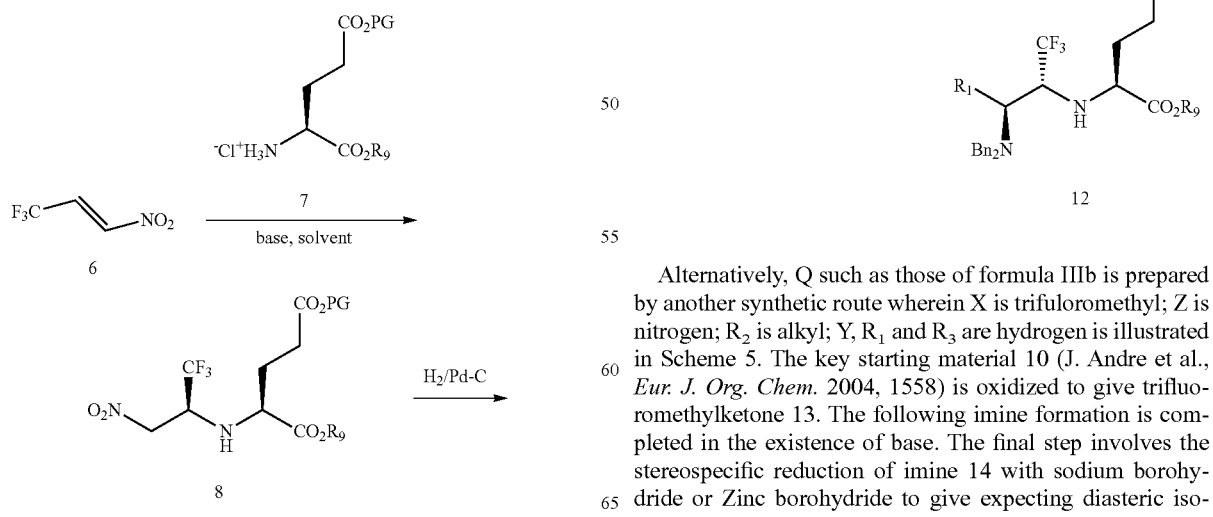

Q such as those of formula III$_b$ are commercial available, known in the literature or may be conveniently prepared by a variety methods familiar to those skilled in the art. One common route for the synthesis of formula III wherein X is trifuloromethyl; Z is nitrogen; $R_2$ is alkyl; Y, $R_1$ and $R_3$ are hydrogen is illustrated in Scheme 4. The starting material 10 is commercial available, known in literature (J. Andre et al., *Eur. J. Org. Chem.* 2004, 1558). The key step involves the stereospecific $S_N2$ triflate 11 displacement with glutamic acid diester 7 (P. O'Shea et al., *J. Org. Chem.* 2009, 5, 1605).

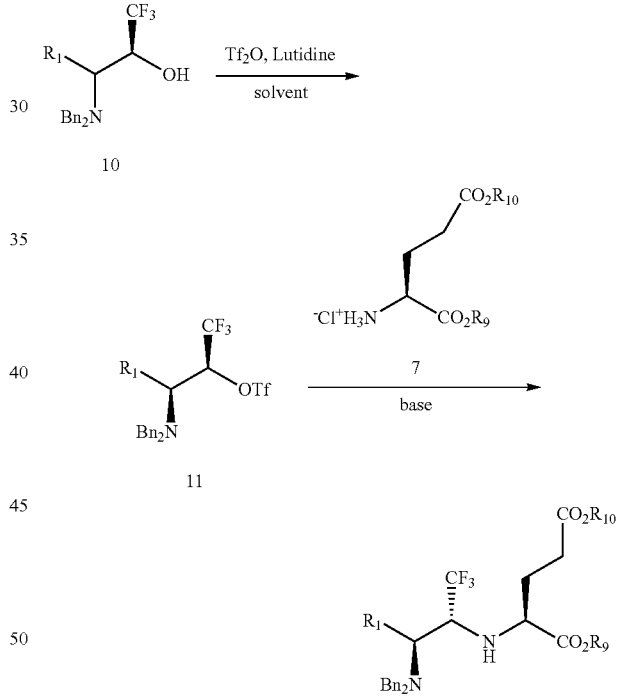

Alternatively, Q such as those of formula IIIb is prepared by another synthetic route wherein X is trifuloromethyl; Z is nitrogen; $R_2$ is alkyl; Y, $R_1$ and $R_3$ are hydrogen is illustrated in Scheme 5. The key starting material 10 (J. Andre et al., *Eur. J. Org. Chem.* 2004, 1558) is oxidized to give trifluoromethylketone 13. The following imine formation is completed in the existence of base. The final step involves the stereospecific reduction of imine 14 with sodium borohydride or Zinc borohydride to give expecting diasteric isomers 12 and 15 of A (G. Huges et al., *Angew Chem. Int. Ed.* 2007, 46, 1839).

Scheme 5

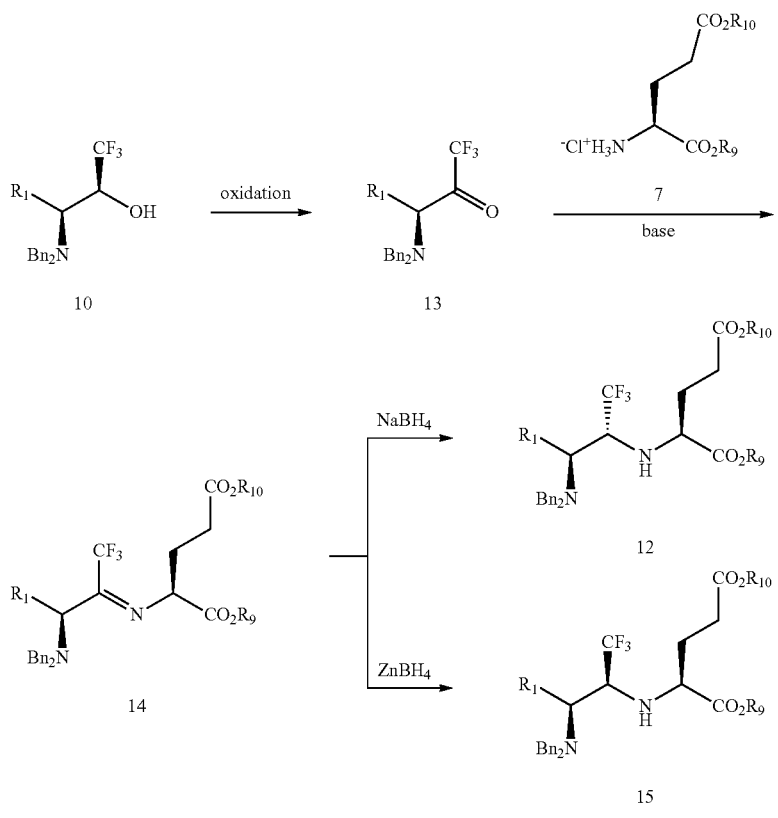

Alternatively, Q such as those of formula IIIb is also prepared by another synthetic route wherein X is trifuloromethyl; Z is nitrogen; $R_2$ is alkyl; Y, $R_1$ and $R_3$ are hydrogen is illustrated in Scheme 6. The condensation of the known starting material diamine 16 (M. Mandal et al., *J. Am Chem. Soc.* 2002, 6538) with aldehyde 17 is yielded imine 18. The following diastereoselective Strecker-type reaction of imine 18 with TMSCN is completed in the existence of catalytic amount of Lewis acid. The final step involves the hydrolysis of the cyano intermediate to give expecting diasteric isomer 12 of A (F. Huguentt et al., *J. Org. Chem.* 2006, 71, 7075).

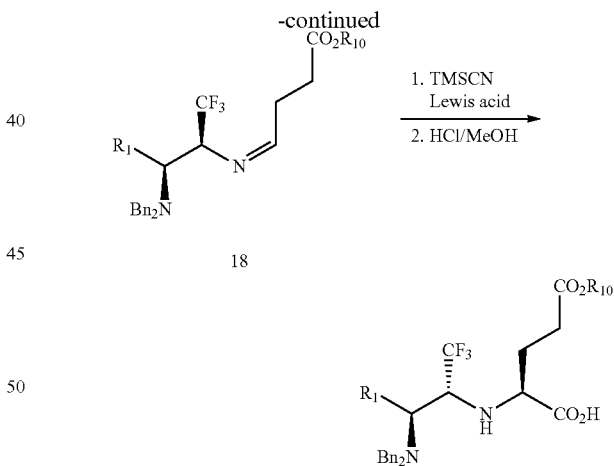

Scheme 6

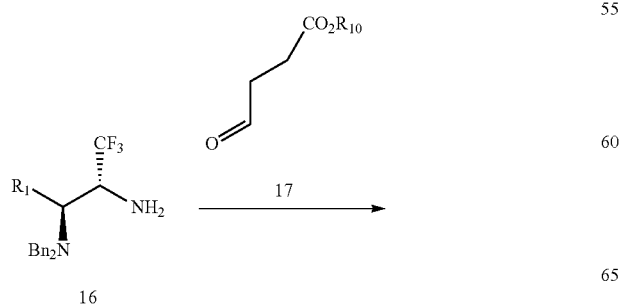

Q such as those of formula IV are commercial available, known in the literature or may be conveniently prepared by a variety methods familiar to those skilled in the art. One common route for the synthesis of compounds of formula IV wherein X is oxygen; Z is carbon; $R_2$ is alkyl; W, Y, $R_1$ and $R_3$ are hydrogen is illustrated in Scheme 7. The starting material β-ketoester 19 is commercial available, known in literature (R. Hoffman et al., *J. Org. Chem.* 1999, 64, 1558). Alkylation of β-ketoester 19 with triflate 20, followed decarboxylation and deprotection of $R_9$ to provide ketomethylen isoester 21 (R. Hoffman et al., *J. Org. Chem.* 1999, 64, 1558; P. S. Dragovich et al., *J. Med. Chem.* 1999, 42, 1203).

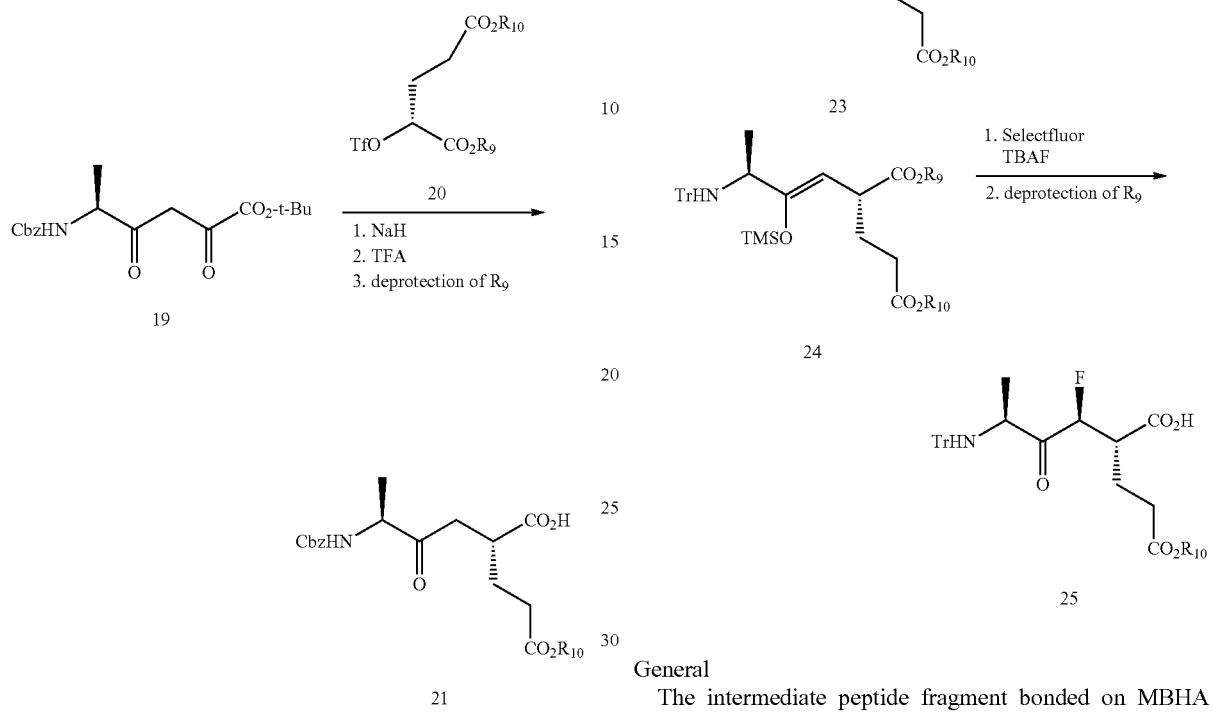

Q such as those of formula IV wherein X is oxygen; Z is carbon; $R_2$ is alkyl; W is fluorine; Y, $R_1$ and $R_3$ are hydrogen are commercial available, known in the literature or may be conveniently prepared by a variety methods familiar to those skilled in the art. One common route for the synthesis of those of formula IV is illustrated in Scheme 8. The starting material tritylated β-ketoester 22 is commercial available, or prepared according to the literature (R. Hoffman et al., *J. Org. Chem.* 1999, 64, 1558). Alkylation of β-ketoester 22 with triflate 20, followed decarboxylation to provide ketomethylen isoester 23, then 23 is converted to the corresponding Z-TMS enolether and fluorinated with Selectfluor and final deprotection to give monofluoro ketomethylene isoester 25 (R. Hoffman et al., *J. Org. Chem.* 1999, 64, 1558; P. S. Dragovich et al., *J. Med. Chem.* 1999, 42, 1203).

General

The intermediate peptide fragment bonded on MBHA resin can be produced by solid phase peptide chemistry on an Applied Biosystems (ABI) 460A peptide synthesizer using a MBHA resin (Applied Biosystems Inc., lot #A1A023, 0.77 mmol/g). All amino acids have their a-amino groups protected by the tert-butyloxycarbonyl (t-Boc) group. Those with reactive side chains have them protected as follows: Arg (Tos); Lys (Cl-Z); Trp (CHO); Glu (CHex); Tyr (Br-Z); Ser (Bzl); Asp (OBzl); Thr (Bzl).

The protected amino acids are activated in dichloromethane (DCM) with one half an equivalent of dicyclohexylcarbodiimide (DCC) per equivalent of amino acid to give the symmetric anhydride of the amino acid. However, arginine, glutamine, and glycine residues are activated by forming the 1-hydroxybenzotriazole (HOBt) esters of these amino acids (1:1:1 equivalents of amino acid, HOBt, and DCC in dimethylformamide (DMF)).

Residues are sequentially connected from the C-terminal towards the N-terminal end with a series of coupling and deprotection cycles. A coupling cycle consists of the activated amino acid undergoing nucleophilic substitution by the free primary amine of the previously coupled amino acid. Deprotection is the removal of the N-terminal blocking group Boc with anhydrous trifluoroacetic acid (TFA). This generates a free amine group after neutralization with diisopropylethylamine (DIEA).

The synthesis scale is 0.5 mmol .The concentration of functional sites on the MBHA-resin was 0.77 mmol/g, 649 mg of resin was used. A two fold molar excess of the symmetric anhydride is for all of the amino acids .The C-terminal Arginine is coupled to the MBHA-resin via standard protocols All residues are double-coupled. That is each residue is coupled to the resin twice to ensure the complete reaction of the NH2 group on the resin. The second coupling is performed without a Boc deprotection step prior to re-addition of the amino acid. This helps to completely react all of the tree amine groups of the resin. The tryptophan residue is quadruple coupled. After the second coupling step of each double-coupling cycle the terminal Boc groups are removed with anhydrous TFA and neutralized with DIEA.

The formyl side chain-blocking group on the tryptophan residue is removed with piperidine in DMF prior to cleaving the peptide from the resin. After the peptidyl-resin is transferred to a 50 ml sintered glass funnel, it is washed several times with DCM and DMF. Then 3-5 ml of a 50/50 piperidine/DMF solution is added to the peptide resin so that it is just covered. After 5 minutes the piperidine /DMF is removed by vacuum and 3-5 ml of piperidine/DMF was added. After 10 minutes, the piperidine/DMF again is removed by vacuum filtration and 15-20 ml of piperidine/ DMF is added. After 15 minutes the piperidine/DMF is removed and the peptidyl-resin is washed with DMF several times followed by DCM. The peptide-resin is then placed into a vacuum oven (no heat) to complete solvent removal.

Alternatively, the required polymer-bonded peptide fragment can also be prepared by using Fmoc protected. Rink Amide MBHA resin, Fmoc protected amino acids, O-benzotriazol-1-yl-N, N, N', N'-tetramethyl-uronium hexafluorophosphate (HBTU) in N,N-dimethylformamide (DMF) solution and activation with N-methyl morpholine (NMM), and piperidine deprotection of Fmoc groups (Step 1). When required, the selective deprotection of the Lys (Aloc) group was performed manually and accomplished by treating the resin with a solution of 3 eq. of Pd (PPh$_3$)$_4$ dissolved in 5 mL of CHCl$_3$: NMM: HOAc (18:1:0.5) for 2 h (Step 2). The resin was then washed with CHCl$_3$ (6×5 mL), 20% HOAc in DCM (6×5 mL), DCM (6×5 mL), and DMF (6×5 mL). In some instances, the synthesis was then re-automated for the addition of one AEEA (aminoethoxyethoxyacetic acid) group, the addition of acetic acid or the addition of a 3-maleimidopropionic acid (MPA) (Step 3). Resin cleavage and product isolation was performed using 85% TFA/5% TIS/5% thioanisole and 5% phenol, followed by precipitation by dry-ice cold Et$_2$O (Step 4). The products were purified by preparative reversed phased HPLC using a Varian (Rainin) preparative binary HPLC system: gradient elution of 30-55% B (0.045% TFA in H$_2$O (A) and 0.045% TFA in CH$_3$CN (B)) over 180 min at 9.5 mL/min using a Phenomenex Luna 10 µ phenyl-hexyl, 21 mm×25 cm column and UV detector (Varian Dynamax UVD II) at 214 and 254 nm. Purity was determined 95% by RP-HPLC mass spectrometry using a Hewlett Packard LCMS-1100 series spectrometer equipped with a diode array detector and using electro-spray ionization.

Protective groups are chemical moieties utilized to protect peptide derivatives from reacting with themselves. Such protective groups include acetyl, fluorenylmethyloxycarbonyl (FMOC), t-butyloxycarbonyl (Boc), benzyloxycarbonyl (CBZ), and the like. The specific protected amino acids are depicted in Table 1.

TABLE 1

NATURAL AMINO ACIDS AND THEIR ABBREVIATIONS

| NAME | 3-Letter abbreviation | 1-letter Abbreviation | protected Amino Acids |
|---|---|---|---|
| Alanine | Ala | A | Fmoc-Ala-OH |
| Arginine | Arg | R | Fmoc-Arg (pbf)-OH |
| Asparagine | Asn | N | Fmoc-Asn (Trt)-OH |
| Aspartic acid | Asp | D | Fmoc-Asp (tBu)-OH |
| Cysteine | Cys | C | Fmoc-Cys (Trt)-OH |
| Glutamic acid | Glu | E | Fmoc-Glu (tBu)-OH |
| Glutamine | Gln | Q | Fmoc-Gln(Trt)-OH |
| Glycine | Gly | G | Fmoc-Gly-OH |
| Histidine | His | H | Fmoc-His(Trt)-OH |
| Isoleucine | Ile | I | Fmoc-Ile-OH |
| Leucine | Leu | L | Fmoc-Leu-OH |
| Lysine | Lys | K | Fmoc-Lys (Mtt)-OH |
| Methionine | Met | M | Fmoc-Met-OH |
| Phenylalanine | Phe | F | Fmoc-Phe-OH |
| Proline | Pro | P | Fmoc-Pro-OH |
| Serine | Ser | S | Fmoc-Ser (tBu)-OH |
| Threonine | Thr | T | Fmoc-Thr (tBu)-OH |
| Tryptophan | Trp | W | Fmoc-Trp(Boc)-OH |
| Tyrosine | Tyr | Y | Boc-Tyr(tBu)-OH |
| Valine | Val | V | Fmoc-Val-OH |

Q-linker-a: Preparation of 2S, 5R-2-(3-tert-Butoxycarbonylamino-but-1-enyl)-pentanedioic acid 5-tert-butyl ester

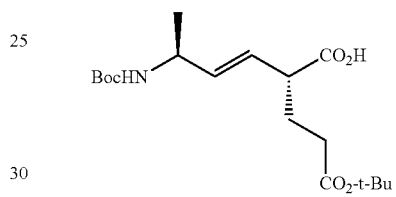

2S, 5R-2-(3-tert-Butoxycarbonylamino-but-1-enyl)-pentanedioic acid 5-tert-butyl ester 1-methyl ester (*J. Chem. Soc., Perkin Trans.* 1, 2001, 2445) (370 mg, 1 mmol) in methanol (2 mL) is treated with LiOH (1M, 2 mL) at room temperature for 1 hr. Most of the solvent is evaporated by vacumm, diluted with water (10 mL) and pH is adjusted to 5, and the aqueous layer is extracted with ethyl acetate (3×30 mL) to yield the title product as foam (320 mg, 90%). $^1$H NMR δ 5.43 (m, 1H), 5.33 (dd, J=15.5, 5.2 Hz, 1H), 4.59 (d, J=7.6 Hz, 1H), 3.88 (m, 1H), 2.91 (m, 1H), 2.25 (m, 2H), 1.91-2.04 (m, 1H), 1.67-1.80 (m, 1H), 1.57 (s, 9H), 1.47 (s, 9H), 1.14 (d, J=6.7 Hz, 3H). LCMS 358 (M$^+$+1).

Q-linker-b: Preparation of 2S, 5R-2-(3-tert-Butoxycarbonylamino-2-fluoro-but-1-enyl)-pentanedioic acid 5-tert-butyl ester

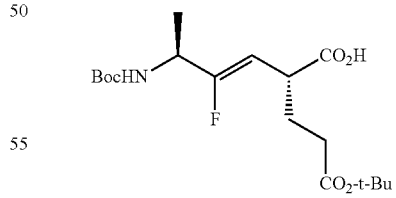

Step A: Preparation of 2S, 5R-2-(3-tert-Butoxycarbonylamino-2-fluoro-but-1-enyl)-pentanedioic acid 1-(S) sultam 5-tert-Butoxycarbonylamino-4-fluoro-2-(3-hydroxy-propyl)-hex-3-enoic acid (S) sultam (*Tetrahedron*, 2008, 64, 4332) (502 mg, 1 mmol) in DMF (5 mL) is added PDC (pyridinium dichromate, 2.5 mmol) and the resulting solution is stirred at rt for 64 hr. The reaction mixture is diluted with brine (20 mL) and extracted with ethyl acetate (3×20 mL). The combined organic extracts are dried over MgSO$_4$ and the solvent is evaporated under reduced pressure. The residue is purified by flash column to yield the acid as foam (425 mg, 79%), which used without further purification.

Step B: Preparation of 2S, 5R-2-(3-tert-Butoxycarbonylamino-2-fluoro-but-1-enyl)-pentanedioic acid 5-tert-butyl ester 1-(S) sultam 2S, 5R-2-(3-tert-Butoxycarbonylamino-2-fluoro-but-1-enyl)-pentanedioic acid 2-(S) sultam from Step A (400 mg, 0.75 mmol) in dichloromethane (10 mL) is treated with tert-butanol (0.5 mL, 10 quive), DCC (1.5 mmol) and DMAP (1.5 mmol). The reaction mixture is stirred 24 hr before diluted with brine (20 mL), extracted with ethyl acetate (3×20 mL). The combined organic extracts are dried over MgSO$_4$ and the solvent is evaporated under reduced pressure. The residue is purified by flash column to yield the tert-butyl ester as foam (425 mg, 79%). $^1$H NMR δ 5.33 (m, 1H), 4.54 (m, 1H), 3.88 (m, 1H), 3.37 (s, 2H), 3.23 (m, 1H), 2.25 (m, 2H), 1.91-2.14 (m, 4H), 1.67-1.80 (m, 5H), 1.57 (s, 9H), 1.47 (d, J=7.6 Hz, 3H), 1.18 (s, 3H), 1.14 (s, 3H). LCMS 574 (M++1).

Step C: Preparation of 2S, 5R-2-(3-tert-Butoxycarbonylamino-2-fluoro-but-1-enyl)-pentanedioic acid 5-tert-butyl ester To a solution of the tert-butyl ester from Step B (410 mg, 0.72 mmol) and aqueous 50% H$_2$O$_2$ (260 mL, 3.6 mmol) in THF-H$_2$O (5:1, 12 mL) at 0° C. is added LiOH (1N, 1.44 mL), and the mixture is stirred at room temperature for 2 h. After pH is adjusted to 5, the mixture is extracted by ethyl acetate (3×15 mL). The combined organic extracts are washed by brine and dried over MgSO$_4$. The solvent is evaporated under reduced pressure to give the corresponding acid as foam (262 mg, 95%). $^1$H NMR δ 5.23 (m, 1H), 4.45 (m, 1H), 3.11 (m, 1H), 2.45 (m, 2H), 2.24 (m, 2H), 1.52 (s, 9H), 1.47 (s, 9H). LCMS 376 (M$^+$+1).

Q-linker-c: Preparation of 2R, 5R 2-[1-(tert-Butoxycarbonylamino-methyl)-2,2,2-trifluoro-ethylaminol-pentanedioic acid 5-tert-butyl ester

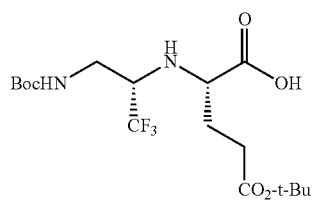

StepA: Preparation of 2R, 5R 2-[1-(tert-Butoxycarbonylamino-methyl)-2,2,2-trifluoro-ethylamino]-pentanedioic acid 5-tert-butyl ester 1-methyl ester To a solution of 2-(1-Aminomethyl-2,2,2-trifluoro-ethylamino)-pentanedioic acid 5-tert-butyl ester 1-methyl ester hydrochloride salt (Org. Lett., 2003, 5, 3887) (364 mg, 1 mol) and Boc$_2$O (260 mg, 1.2 mmol) in dichloromethane (15 mL) at 0° C. is added a solution of DIPEA (0.2 mL, 1.5 mmol) in dichloromethane (1 mL), and the mixture is stirred at room temperature for 6 h. The mixture is diluted with ethyl acetate (30 mL). The mixture is washed by 0.1N HCl, brine and dried over MgSO$_4$. The solvent is evaporated under reduced pressure and followed by FC to give the corresponding di-ester as foam (420 mg, 85%). $^1$H NMR δ 4.54 (m, 1H), 4.12 (m, 1H), 3.68 (s, 3H), 3.45 (m, 1H), 3.11 (m, 2H), 2.45 (m, 2H), 2.24 (m, 2H), 1.52 (s, 9H), 1.47 (s, 9H). LCMS 430 (M$^+$+1), 330 (M$^+$1-tert-Bu).

StepB: Preparation of 2R, 5R 2-[1-(tert-Butoxycarbonylamino-methyl)-2,2,2-trifluoro-ethylaminol-pentanedioic acid 5-tert-butyl ester To a solution of the tert-butyl ester from Step A (420 mg, 0.92 mmol) in THF-H$_2$O (5:1, 12 mL) at 0° C. is added LiOH (1N, 1.44 mL), and the mixture is stirred at room temperature for 2 h. After pH is adjusted to 5, the mixture is extracted by ethyl acetate (3×15 mL). The combined organic extracts are washed by brine and dried over MgSO$_4$. The solvent is evaporated under reduced pressure to give the corresponding acid as foam (362 mg, 92%). $^1$H NMR δ 4.50 (m, 1H), 4.08 (m, 1H), 3.45 (m, 1H), 3.11 (m, 2H), 2.45 (m, 2H), 2.24 (m, 2H), 1.52 (s, 9H), 1.47 (s, 9H). LCMS 430 (M$^+$+1), 330 (M$^+$1-tert-Bu).

Q-linker-d: Preparation of 2R-2-(1S, 2S-2-tert-Butoxycarbonylamino-1-trifluoro-methyl-propylamino)-pentanedioic acid 5-tert-butyl ester

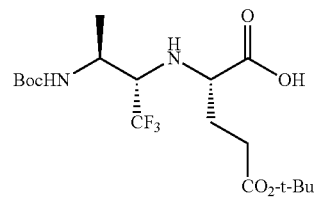

Step A: 2S, 3S-3-Dibenzylamino-1, 1, 1-trifluorobutane-2-trifluoromethanesulfonate To a solution 2S, 3S-3-dibenzylamino-1,1,1-trifluoro-butan-2-ol (Eur. J. Org. Chem. 2004, 1558) (3.23 g, 10 mmol) and 2,6-lutidine (1.7 g, 16 mmol) in c-hexane (25 mL) at −10° C. is added triflic anhydride (4.2 g, 15 mmol) at a rate to maintain the temperature <10° C. and reaction is continued for 1.5 h. The reaction mixture is diluted with water (25 mL) and c-hexane (50 mL). The organic layer is washed by 1N HCl (2×15mL) and brine (15 mL). After dried over MgSO$_4$, the solvent is evaporated under reduced pressure to give the corresponding trifluoromethaneslfonate (4.34 g, 96%).

Step B: 2S-2-(1S, 2S-2-Dibenzylamino-1-trifluoromethyl-propylamino)-pentanedioic acid 1-benzyl ester 5- tert-butyl ester Potassium carbonate (2.08 g, 15 mmol) is added to a solution of triflate from Step A (4.55 g, 10 mmol), c-hexane (25 mL). The mixture is heated to 65-70° C. for 24 h. The mixture is cooled to room temperature and diluted with water (25 mL) and c-hexane (50 mL), then the mixture stirred for 10 min. The layers are separated, the organic layer is washed by 1N HCl (2×15mL) and brine (15 mL). After dried over MgSO$_4$, the solvent is evaporated under reduced pressure to give the corresponding ester (5.88 g, 95%).

Step C: 2R-2-(1S, 2S-2-tert-Butoxycarbonylamino-1-trifluoromethylpropylamino)-pentanedioic acid 5-tert-butyl ester Hydrogenation of a solution of 2S-2-(1S, 2S-2-Dibenzylamino-1-trifluoromethyl-propylamino)-pentanedioic acid 1-benzyl ester 5-tert-butyl ester from Step B (5.4 g, 9 mmol) is completed in methanol (50 mL) and Pd/C (0.9 g) at 50 Psi for 24 h. After filtration to remove catalyst, the filtrate is concentrated under vacuum. The residue is dissolved in dichloromethane (50 mL) and treated with Boc$_2$O (2.60 g, 12 mmol) in dichloromethane (25 mL) at 0° C., and followed by the addition of a solution of DIPEA (2 mL, 15 mmol) in dichloromethane (10 mL), and the mixture is stirred at room temperature for 6 h. The mixture is diluted with ethyl acetate (60 mL). The mixture is washed by 0.1N HCl, brine and dried over MgSO₄. The solvent is evaporated under reduced pressure and followed by FC to give the corresponding title compound as foam Q-linker-e: 2S-2-(3S-3-tert-Butoxycarbonylamino-2-oxo-butyl)-pentanedioic acid 5- tert-butyl ester

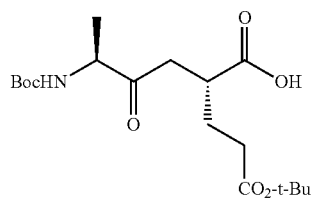

To a solution of 2S-2-(3S-3-tert-Butoxycarbonylamino-2-oxo-butyl)-pentanedioic acid 5- tert-butyl ester 1-methyl ester (*J. Med. Chem.* 1999, 42, 1203; *Bioorg. Med. Chem.* 2005, 13, 5240) (387 mg, 1 mmol) in THF-H₂O (5:1, 12 mL) at 0° C. is added LiOH (1N, 1.44 mL), and the mixture is stirred at room temperature for 2 h. After pH is adjusted to 5, the mixture is extracted by ethyl acetate (3×15mL). The combined organic extracts are washed by brine and dried over MgSO₄. The solvent is evaporated under reduced pressure to give the corresponding acid as foam (362 mg, 92%). ¹H NMR δ 4.63 (m, 1H), 4.38 (br, 1H), 2.68 (d, J=7.6 Hz, 2H), 2.58 (m, 1H), 2.25 (dd, J=12.3, 7.6 Hz, 2H), 1.92 (m, 2H), 1.49 (s, 9H), 1.47 (s, 9H), 1.41 (d, J=7.6 Hz, 3H). LCMS 374 (M⁺+1), 274 (M⁺1-tert-Bu).

Q-linker-f: 2R-2-(1S, 3S-3-tert-Butoxycarbonylamino-1-fluoro-2-oxo-butyl)-pentanedioic acid 5-tert-butyl ester

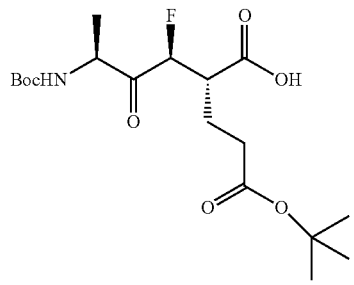 [SMILES: C[C@H](NC(=O)OC(C)(C)C)C(=O)[C@@H](F)[C@@H](CCC(=O)OC(C)(C)C)C(=O)O]

Step A: 2S-2-(1S, 3S-3-tert-Butoxycarbonylamino-1-fluoro-2-oxo-butyl)-pentanedioic acid 5- tert-butyl ester 1-methyl ester 2S-2-[1S, 3S-Fluoro-2-oxo-3-(trityl-amino)-butyl]-pentanedioic acid 5-benzyl ester 1-methyl ester (581 mg, 1 mmol) and 10% Pd/C (100 mg) in methanol (25 mL) is hydrogenated in parr shaker 50 Psi for 6 h. The catalyst is removed by filtration through Celite. The filtrate is concentrated. The residue is dissolved in dioxane (25 mL) and treated with 1N NaOH solution (1.2 mL). Boc₂O (238 mg, 1.1 mmol) in dioxane (2 mL) is added the above solution at 0° C. and the mixture is stirred at room temperature for 6 h. The mixture is diluted with ethyl acetate (30 mL). The mixture is washed by 0.1N HCl, brine and dried over MgSO₄. The solvent is evaporated under reduced pressure. The residue is dissolved in dichloromethane (10 mL) is treated with tert-butanol (0.5 mL, 10 quive), DCC (1.5 mmol) and DMAP (1.5 mmol). The reaction mixture is stirred 24 hr before diluted with brine (20 mL), extracted with ethyl acetate (3×20 mL). The combined organic extracts are dried over MgSO₄ and the solvent is evaporated under reduced pressure. The residue is purified by flash column to yield the tert-butyl ester as foam (315 mg, 66%). ¹H NMR δ 4.81 (m, 1H), 4.63 (m, 1H), 4.38 (br, 1H), 3.67 (s, 3H), 2.78 (m, 1H), 2.35 (dd, J=12.3, 7.6 Hz, 2H), 2.06 (m, 2H), 1.49 (s, 9H), 1.47 (s, 9H), 1.41 (d, J=7.6 Hz, 3H). LCMS 406 (M⁺+1), 306 (M⁺1-tert-Bu).

Step B: 2S-2-(1S, 3S-3-tert-Butoxycarbonylamino-1-fluoro-2-oxo-butyl)-pentanedioic acid 5- tert-butyl ester 2S-2-(1S, 3S-3-tert-Butoxycarbonylamino-1-fluoro-2-oxo-butyl)-pentanedioic acid 5- tert-butyl ester 1-methyl ester from Step A (260 mg, 0.65 mmol) in THF-H₂O (5:1, 12 mL) at 0° C. is added LiOH (1N, 1.0 mL), and the mixture is stirred at room temperature for 2 h. After pH is adjusted to 5, the mixture is extracted by ethyl acetate (3×15 mL). The combined organic extracts are washed by brine and dried over MgSO₄. The solvent is evaporated under reduced pressure to give the corresponding acid as foam (238 mg, 95%). ¹H NMR δ 4.81 (m, 1H), 4.63 (m, 1H), 4.38 (br, 1H), 2.78 (m, 1H), 2.35 (dd, J=12.3, 7.6 Hz, 2H), 2.06 (m, 2H), 1.49 (s, 9H), 1.47 (s, 9H), 1.41 (d, J=7.6 Hz, 3H). LCMS 392 (M⁺+1), 292 (M⁺1-tert-Bu).

Example 1

Synthesis of

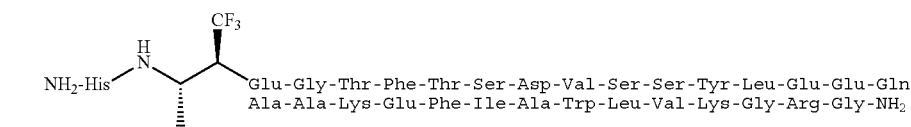

(Namely, the compound of example 1 is

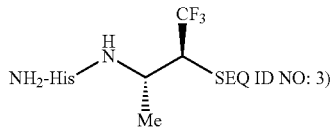

SEQ ID NO: 3)

[Q-linker-d8, Glu22]GLP-1-(7-37)-peptide

Step 1

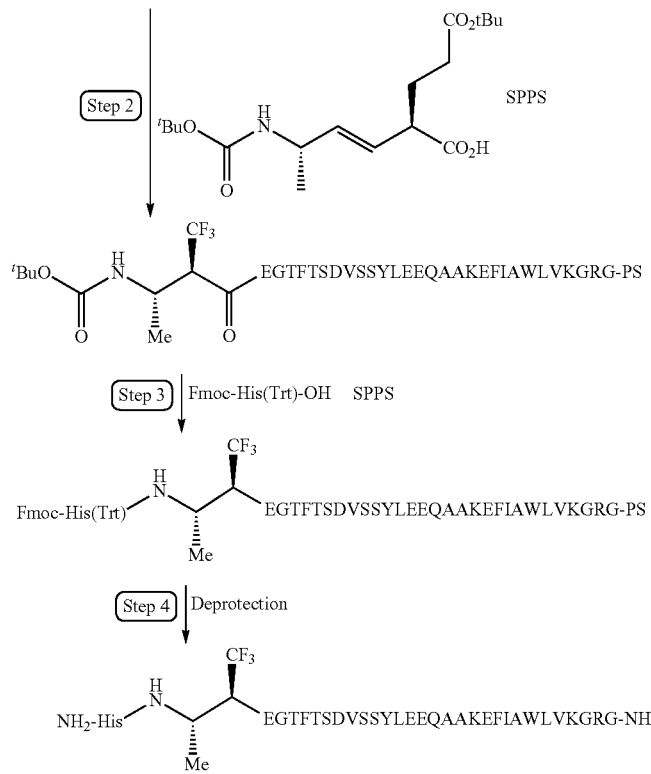

Solid phase peptide synthesis of the analog on a 100 μmole scale is performed using manual solid-phase synthesis and a Symphony Peptide Synthesizer using Fmoc protected Rink Amide MBHA resin, Fmoc protected amino acids, O-benzotriazol-1-yl-N,N,N',N'-tetramethyl-uronium hexafluorophosphate (HBTU) in N,N-dimethylformamide (DMF) solution and activation with N-methyl morpholine (NMM), and piperidine deprotection of Fmoc groups (Step 1). The Boc group in the product of Step2 is cleaved prior to the coupling with Fmoc-His(Trt)-OH. Resin cleavage and product isolation is performed using 85% TFA/5% TIS/5% thioanisole and 5% phenol, followed by precipitation by dry-ice cold Et$_2$O (Step 2). The product is purified by preparative reversed phased HPLC using a Varian (Rainin) preparative binary HPLC system: gradient elution of 30-55% B (0.045% TFA in H$_2$O (A) and 0.045% TFA in CH$_3$CN (B) over 180 min at 9.5 mL/min using a Phenomenex Luna 10 μL phenyl-hexyl, 21 mm×25 cm column and UV detector (Varian Dynamax UVD II) at λ 214 and 254 nm to afford the desired peptide in >95% purity, as determined by RP-HPLC.

The Maldi-Tof MS: 3412. Calculated MS: 3412.

Example 2

Synthesis of

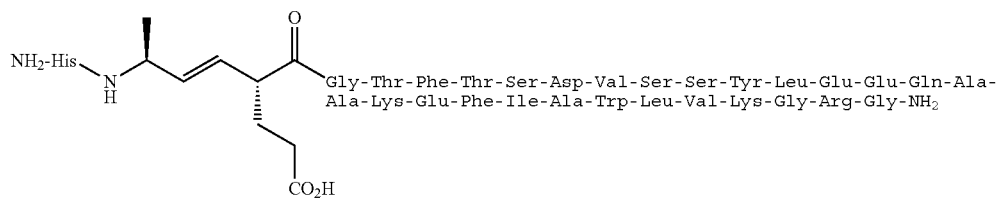

(Namely, the compound of example 2 is [Q-linker-a8-9, Glu22]GLP-1-(7-37)-peptide
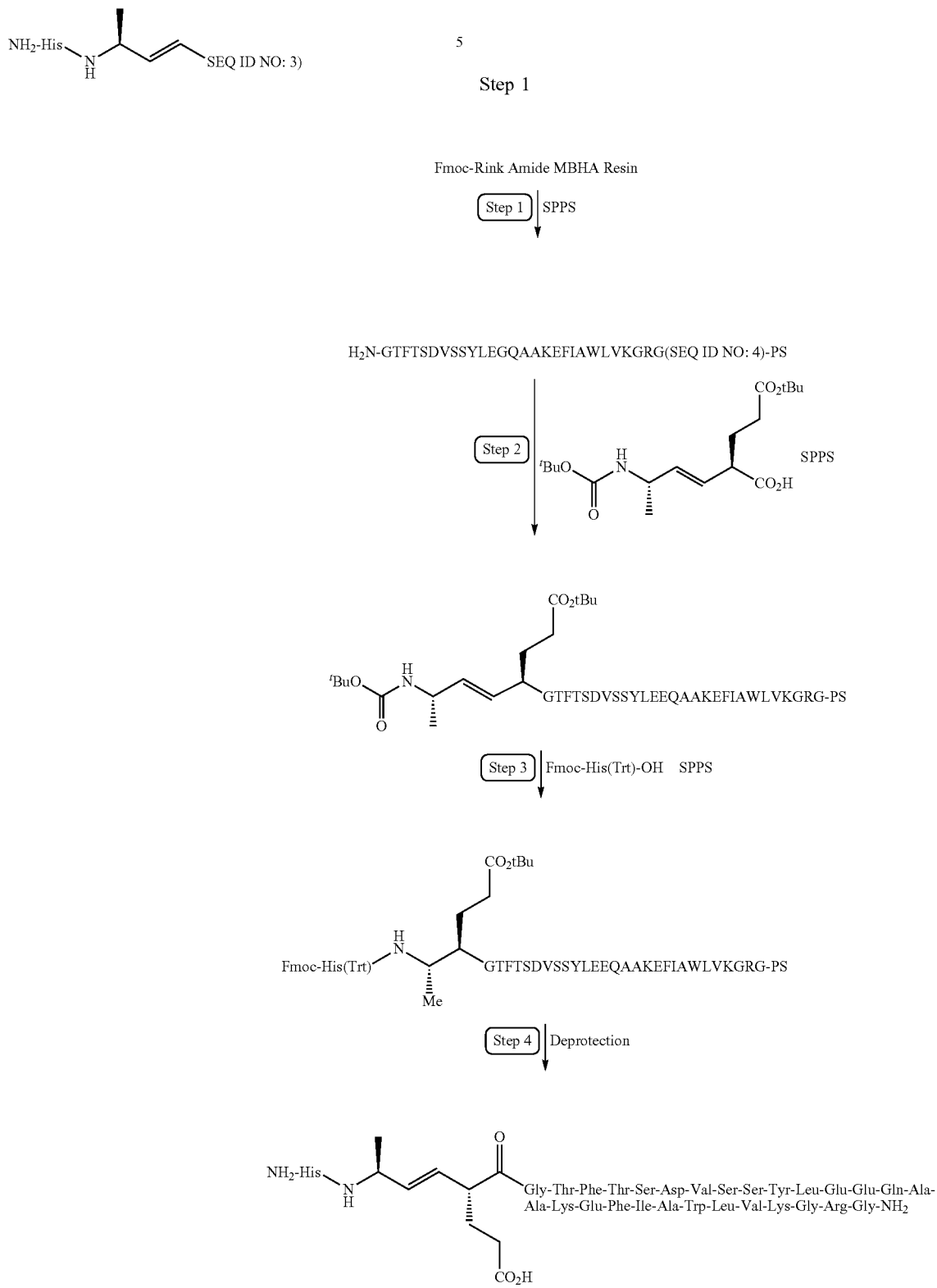
The desired GLP-1 analog is synthesized by using the same sequence and conditions as described for Example 1.
LCMS: 1113 $(M+3H)^{3+}$. Calculated MS: 1113 $(M+3H)^{3+}$.

Example 3
Synthesis of
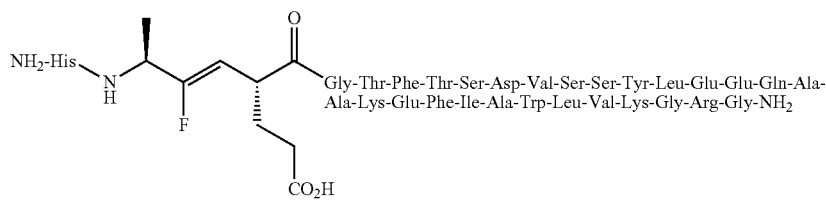
(Namely, the compound of example 3 is
SEQ ID NO: 3.)
[Q-linker-b8-9, Glu22]GLP-1-(7-37)-peptide
Step 1
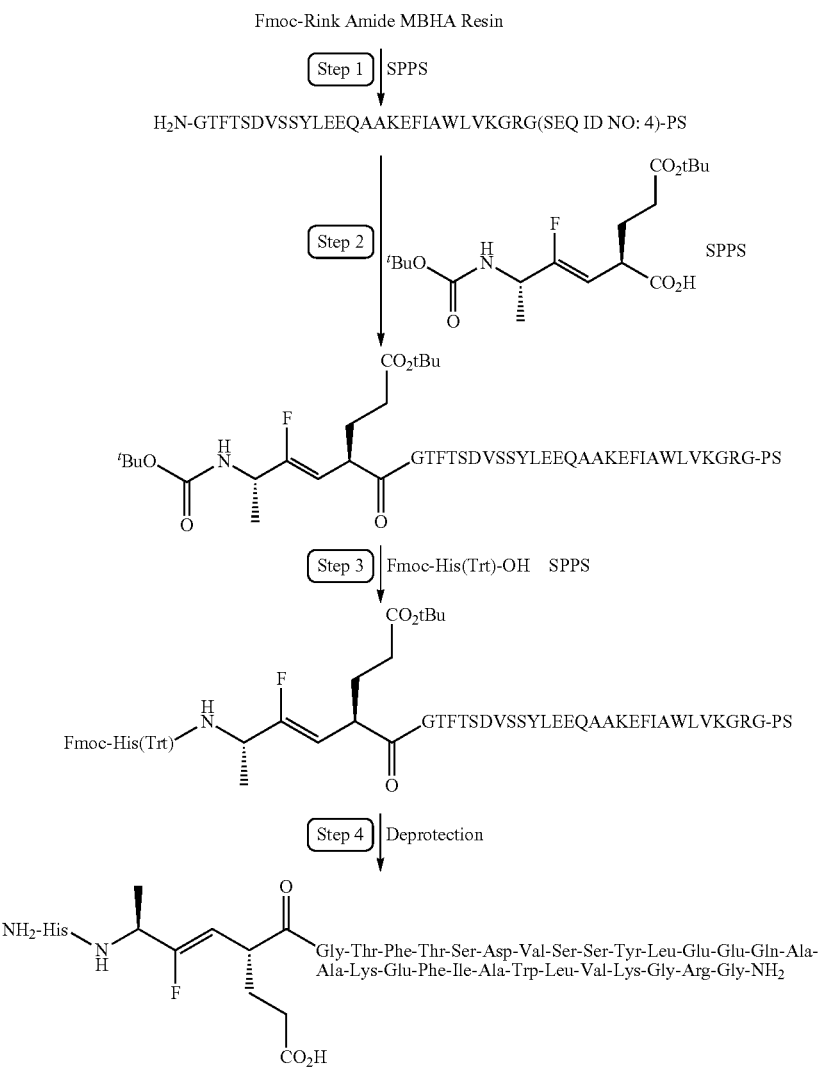

The desired GLP-1 analog is synthesized by using the same sequence and conditions as described for Example 1.
LCMS: 1119 (M+3H)³⁺. Calculated MS: 1119 (M+3H)³⁺.

Example 4

Synthesis of

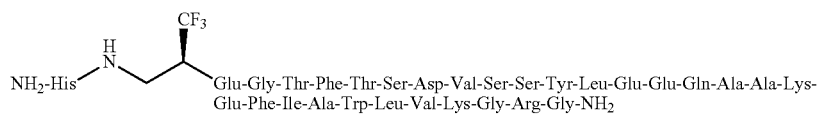

(Namely, the compound of example 4 is

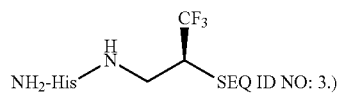 SEQ ID NO: 3.)

[Q-linker-c8, Glu22]GLP-1-(7-37)-peptide

Step 1

Fmoc-Rink Amide MBHA Resin

| Step 1 | SPPS

H₂N-GTFTSDVSSYLEEQAAKEFIAWLVKGRG(SEQ NO: 4)-PS

| Step 2 |

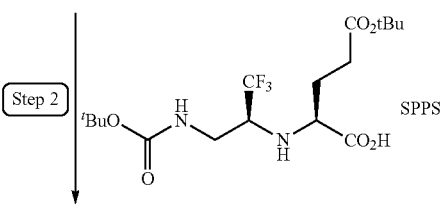

$^t$BuO-...-EGTFTSDVSSYLEEQAAKEFIAWLVKGRG-PS

| Step 3 | Fmoc-His(Trt)-OH  SPPS

Fmoc-His(Trt)-...-EGTFTSDVSSYLEEQAAKEFIAWLVKGRG-PS

| Step 4 | Deprotection

NH₂-His-...-EGTFTSDVSSYLEEQAAKEFIAWLVKGRG-NH₂

The desired GLP-1 analog is synthesized by using the same sequence and conditions as described for Example 1.
The Maldi-Tof MS: 3398. Calculated MS: 3398.

Example 5
Synthesis of
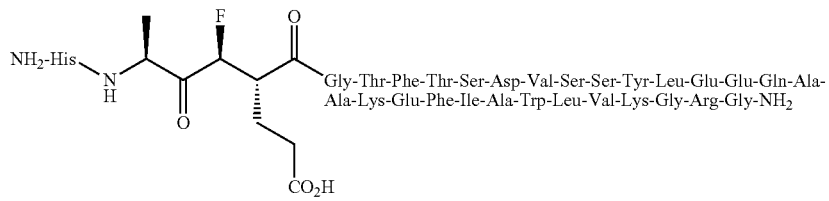
(Namely, the compound of example 5 is
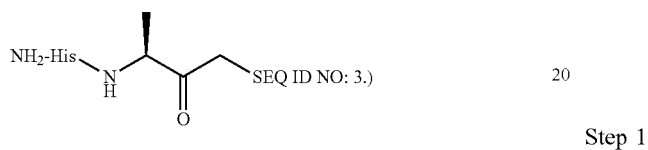
SEQ ID NO: 3.)
[Q-linker-e8-9, Glu22]GLP-1-(7-37)-peptide
Step 1
Fmoc-Rink Amide MBHA Resin
Step 1 | SPPS
↓
H₂N-GTFTSDVSSYLEEQAAKEFIAWLVKGRG(SEQ ID NO: 4)-PS
Step 2 | SPPS
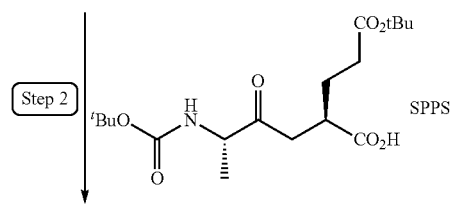
↓
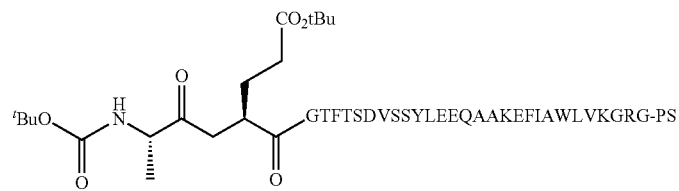
Step 3 | Fmoc-His(Trt)-OH   SPPS
↓
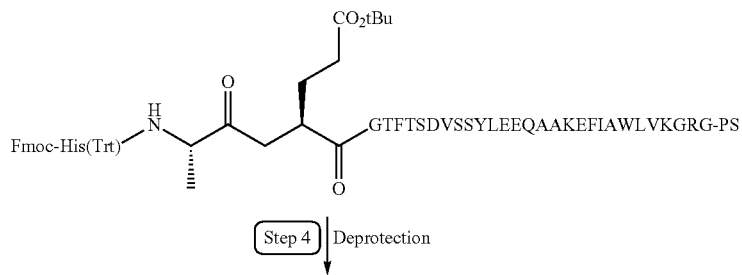
Step 4 | Deprotection
↓

-continued

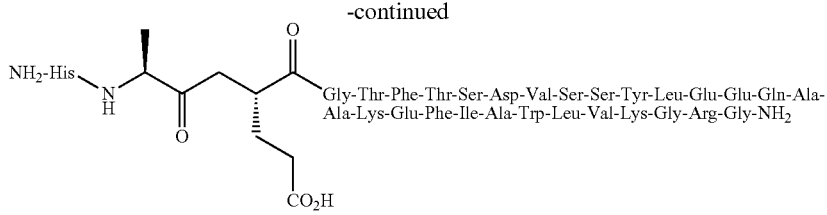

The desired GLP-1 analog is synthesized by using the same sequence and conditions as described for Example 1.
LCMS: 1118 (M+3H)$^{3+}$. Calculated MS: 1118 (M+3H)$^{3+}$.

Example 6

Synthesis of

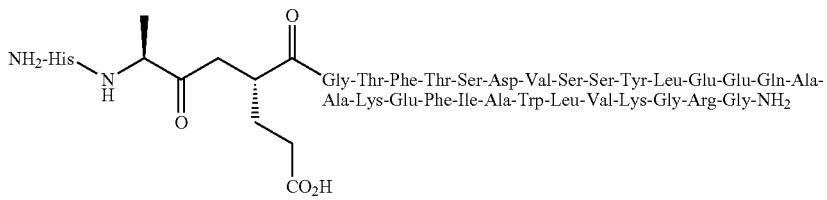

(Namely, the compound of example 6 is [Q-linker-f8-9,Glu22,Arg34]GLP-1-(7-37)-peptide

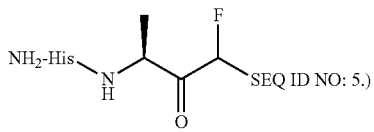

SEQ ID NO: 5.)

Step 1

Fmoc-Rink Amide MBHA Resin

Step 1 | SPPS

H$_2$N-GTFTSDVSSYLEEQAAKEFIAWLVRGRG(SEQ ID NO: 6)-PS

Step 2

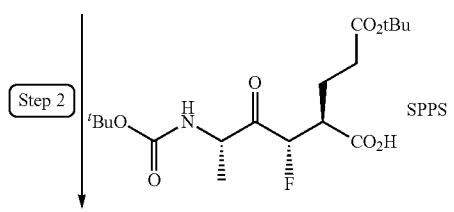

SPPS

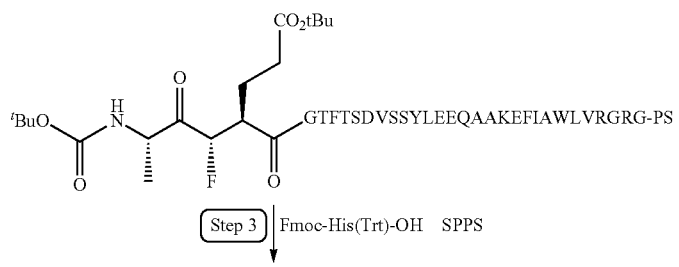

Step 3 | Fmoc-His(Trt)-OH  SPPS

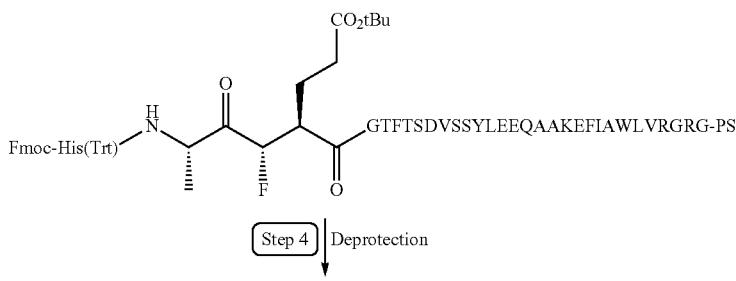

Step 4 | Deprotection

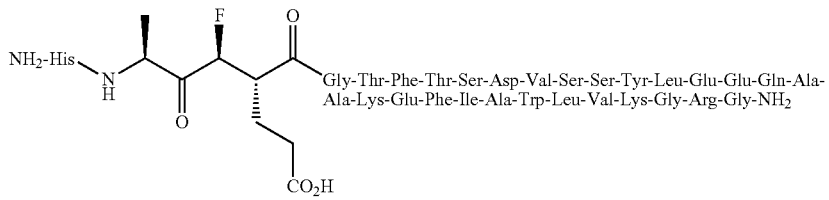

The desired GLP-1 analog is synthesized by using the same sequence and conditions as described for Example 1. LCMS: 1127 (M+3H)$^{3+}$. Calculated MS: 1127 (M+3H)$^{3+}$.

Example 7

Synthesis of

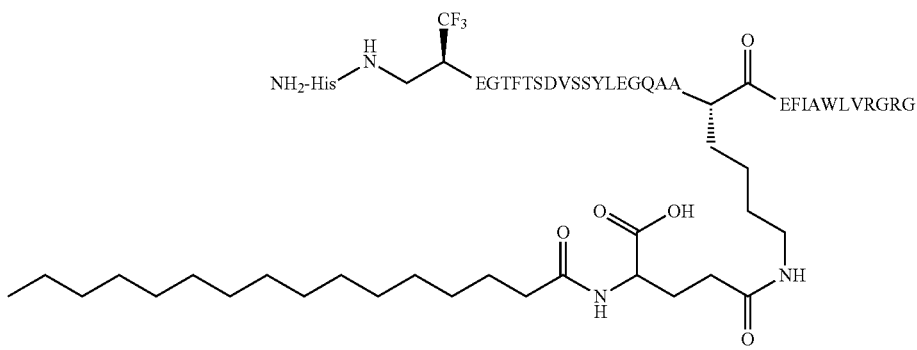

N-$\epsilon^{26}$-[γ-L-glutamyl(N-α-hexadecanoyl)]-[Q-linker-c8,Arg34]GLP-1-(7-37)-peptide (Namely the compound of example 7 is N-e$^{26}$-[$_7$-L-glutamyl (N-α-hexadecanoyl)]-

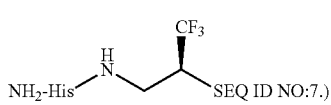

(SEQ ID NO:7.)

A mixture of [A-linker-c8,Arg34]GLP-1-OH (3 6 mg, 1 1 μmol), EDPA (4.0 mg, 30.8 μmol), acetonitrile (260 μl) and water (260 μl) was gently shaken for 5 min. at room temperature. To the resulting mixture was added a solution of N$^α$-hexadecanoyl-Glu(ONSu)-OBut, (1.8 mg, 3.3 μmol) in acetonitrile (44.2 μl), and the reaction mixture was gently shaken for 1 h and 20 mm. at room temperature The reaction was quenched by the addition of a solution of glycine (1.8 mg, 24 2 μmol) in 50% aqueous ethanol (181 μl). A 0.5% aqueous solution of ammonium-acetate (12 ml) and NMP (300 μl) were added, and the resulting mixture eluted onto a Varian 1 g C8 Mega Bond Elut cartridge, the immobilised compound washed with 5% aqueous acetonitrile (10 ml), and finally liberated from the cartridge by elution with TFA (6 ml) The eluate was allowed to stand for 2 h at room temperature and then concentrated in vacuo The residue was purified by column chromatography and a standard acetonitrile/TFA system The title compound (12 mg, 46%) was isolated, and the product was analyzed by PDMS. The m/z value for the protonated molecular ion was found to be 3790±3. The resulting molecular weight is thus 3790±3 amu (theoretical value 3751 amu).

Example 8

Synthesis of

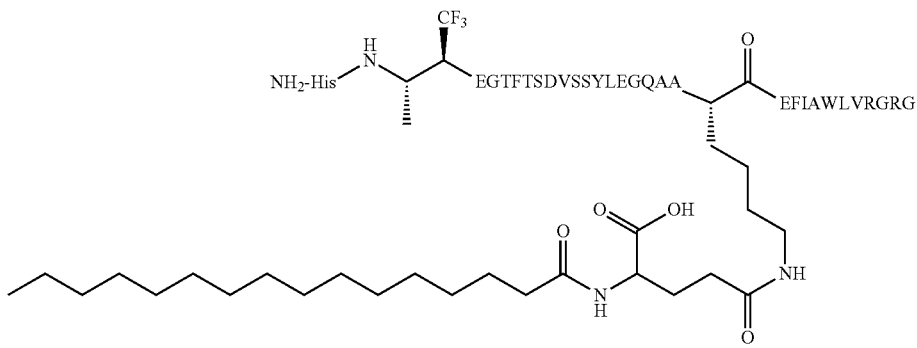

N-ε26-[γ-L-glutamyl(N-α-hexadecanoyl)]-[Q-linker-d8,Arg34]GLP-1-(7-37)-peptide (Namely, the compound of example 8 is N-ε26-[γ-L-glutamyl(N-α-hexadecanoyl)]-

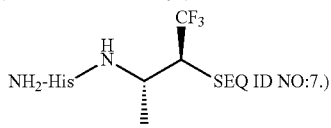

SEQ ID NO:7.)

The desired GLP-1 analog is synthesized by using the same sequence and conditions as described for Example 7.

LCMS: 1268 (M+3H)$^{3+}$. Calculated MS: 1268 (M+3H) 3+.

Example 9

Synthesis of

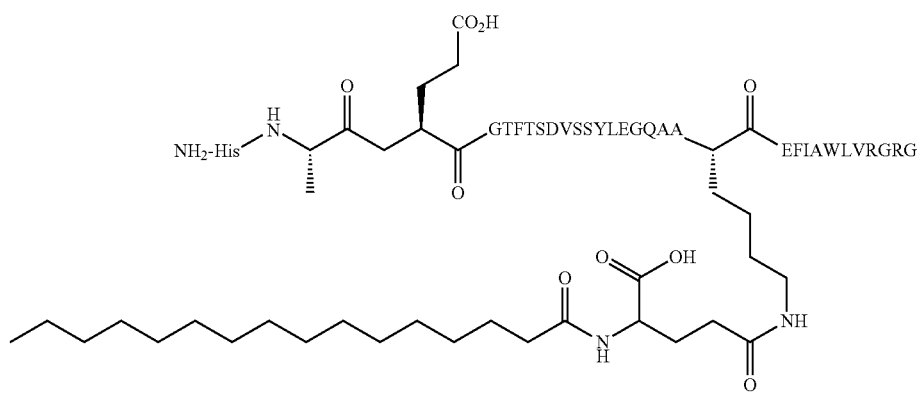

N-ε26-[γ-L-glutamyl(N-α-hexadecanoyl)]-[Q-linker-e8-9,Arg34]GLP-1-(7-37)-peptide (Namely, the compound of example 9 is N-ε26-[γ-L-glutamyl(N-α-hexadecanoyl)]-

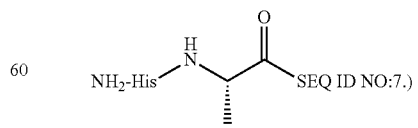

SEQ ID NO:7.)

The desired GLP-1 analog is synthesized by using the same sequence and conditions as described for Example 7.

LCMS: 1250 (M+3H)$^{3+}$. Calculated MS: 1250 (M+3H)$^{3+}$.

Example 10

Synthesis of

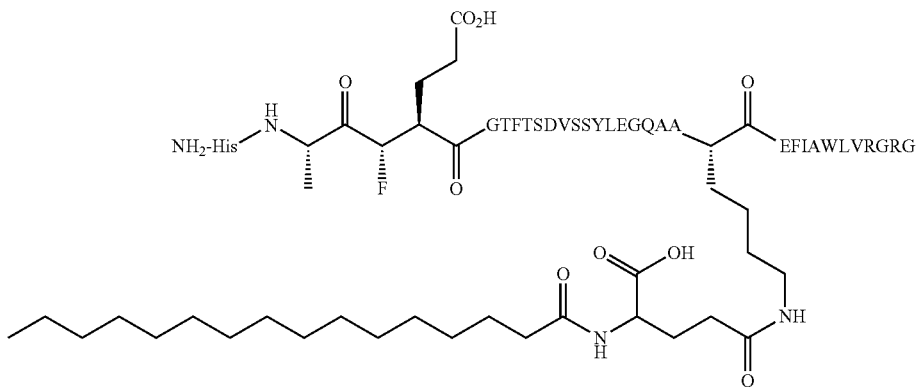

N-ε²⁶-[γ-L-glutamyl(N-α-hexadecanoyl)]-[Q-linker-f8-9,Arg34[GLP-1-(7-37)-peptide (Namely, the compound of example 10 is N-ε²⁶-[γ-L-glutamyl(N-α-hexadecanoyl)]-

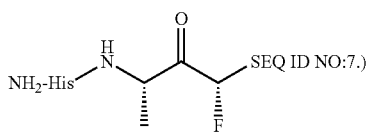

SEQ ID NO:7.)

The desired GLP-1 analog is synthesized by using the same sequence and conditions as described for Example 7.

LCMS: 1256 (M+3H)³⁺. Calculated MS: 1256 (M+3H) 3+.

Example 11

Synthesis of

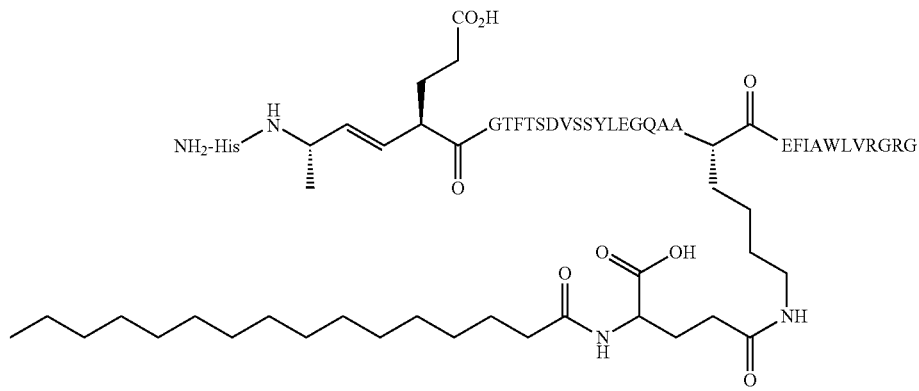

N-ε²⁶-[γ-L-glutamyl(N-α-hexadecanoyl)]-[Q-linker-a8-9,Arg34]GLP-1-(7-37)-peptide (Namely the compound of example 11 is N-ε²⁶-[γ-L-glutamyl(N-α-hexadecanoyl)]-

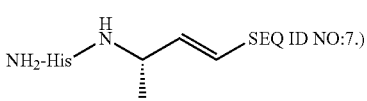

SEQ ID NO:7.)

The desired GLP-1 analog is synthesized by using the same sequence and conditions as described for Example 7.

LCMS: 1244 (M+3H)³⁺. Calculated MS: 1244 (M+3H)³⁺.

Example 12

Synthesis of

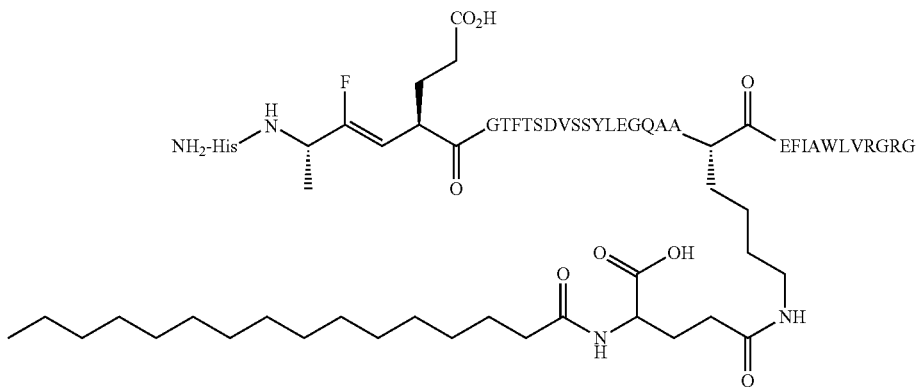

N-ε²⁶-[γ-L-glutamyl(N-α-hexadecanoyl)]-[Q-linker-b8-9,Arg34]GLP-1-(7-37)-peptide (Namely, the compound of example 12 is N-ε²⁶-[γ-L-glutamyl(N-α-hexadecanoyl)]-

SEQ ID NO:7.)

The desired GLP-1 analog is synthesized by using the same sequence and conditions as described for Example 7.
LCMS: 1250 (M+3H)³⁺. Calculated MS: 1250 (M+3H)³⁺.

Example 13

Synthesis of

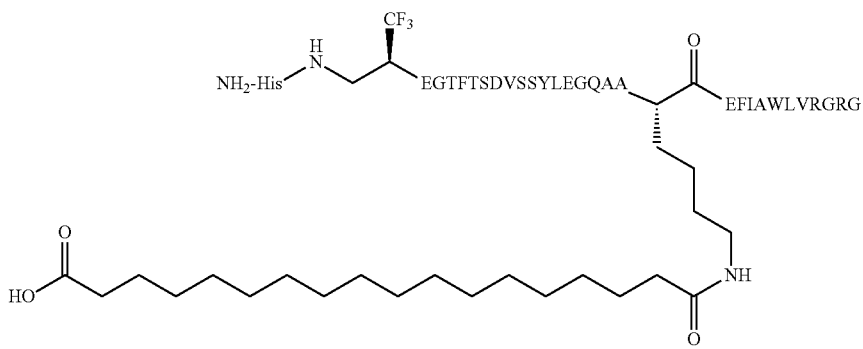

N-ε²⁶-[γ-L-glutamyl(N-α-hexadecanoyl)]-[Q-linker-c8,Arg34]GLP-1-(7-37)-peptide (Namely, the compound of example 13 is N-ε²⁶-[γ-L-glutamyl(N-α-hexadecanoyl)]-

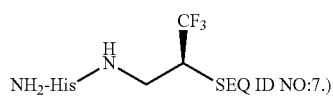

SEQ ID NO:7.)

The desired GLP-1 analog is synthesized by using the same sequence and conditions as described for Example 7 and ω-carboxyheptadecanoic acid 2,5-dioxopyrrolidin-1-yl ester used as starting material instead of Nα-hexadecanoyl-Glu(ONSu)-OBuᵗ.

LCMS: 1239 (M+3H)³⁺. Calculated MS: 1239 (M+3H) 3+.

Example 14

Synthesis of

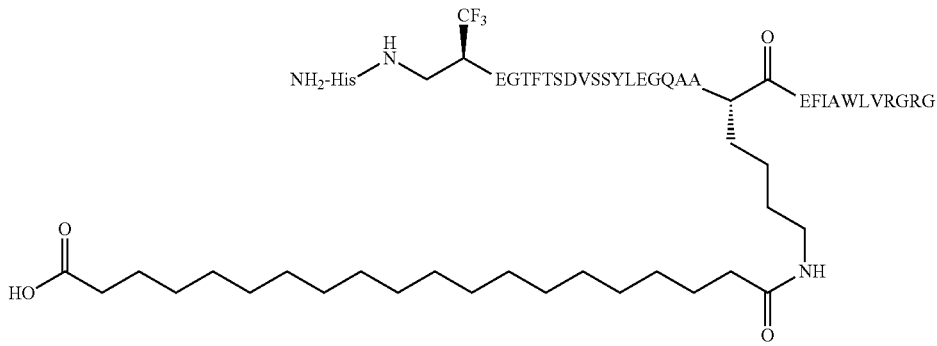

N-ε²⁶-[γ-L-glutamyl(N-α-hexadecanoyl)]-[Q-linker-c8,Arg34]GLP-1-(7-37)-peptide (Namely, the compound of example 14 is N-ε²⁶-[γ-L-glutamyl(N-α-hexadecanoyl)]-

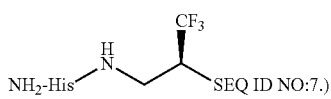

SEQ ID NO:7.)

The desired GLP-1 analog is synthesized by using the same sequence and conditions as described for Example 7 and ω-carboxynonadecanoic acid 2,5-dioxopyrrolidin-1-yl ester used as starting material instead of N^α-hexadecanoyl-Glu(ONSu)-OBuᵗ

LCMS: 1249 (M+3H)³⁺. Calculated MS: 1249 (M+3H)³⁺.

Example 15

Synthesis of

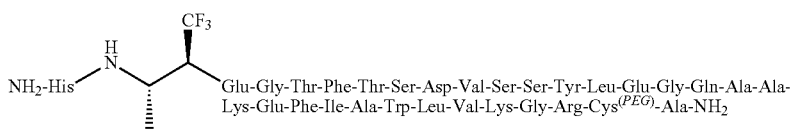

(Namely, the compound of example 15 is

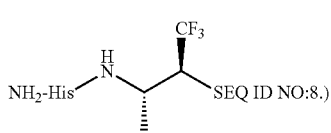

SEQ ID NO:8.)

[Q-linker-d8]GLP-1-(7-37)-Cys$^{(PEG)}$-Ala-NH₂

A mixture of [A-linker-d8] GLP-1-(7-37)-Cys-Ala-NH₂ (3 6 mg, 1 1 μmol) in 50 mmol/L buffer solutions (36 mL) was reacted with 2 mole excess of 20 KDa mPEG-SPA (pH adjusted from 7.5 to 9.0 with 50 mmol/L Tris-HCl buffer) at room temperature for 3 h. The mono-PEGylated GLP-1 conjugates were monitored and purified by reversed-phase high-pressure liquid chromatography (RP-HPLC) on X-tera C18 (4.6×250 mm, 5 m, Waters, Milford, Mass.) at room temperature. The mobile phase consisted of 0.1% TFA in distilled water (eluent A) and ACN containing 0.1% TFA (eluent B). The mobile phase was run with a linear gradient from 30 to 60% eluent B for 20 min at alow rate of 1 mL/min and the UV absorbance of the eluent was monitored at 215 nm. The HPLC fractions corresponding to respective peaks were collected separately, purged with nitrogen, and lyophilized.

Example 16

Synthesis of

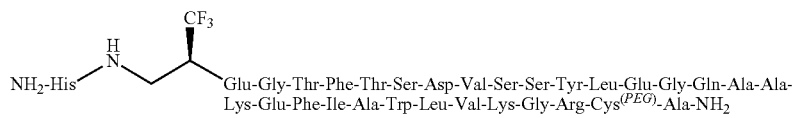

(Namely, the compound of example 16 is

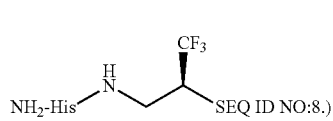

[Q-linker-c8]GLP-1-(7-37)-Cys$^{(PEG)}$-Ala-NH$_2$

The desired GLP-1 analog is synthesized by using the same sequence and conditions as described for Example 13 and 20 KDa mPEG-SPA used.

Example 17

Synthesis of

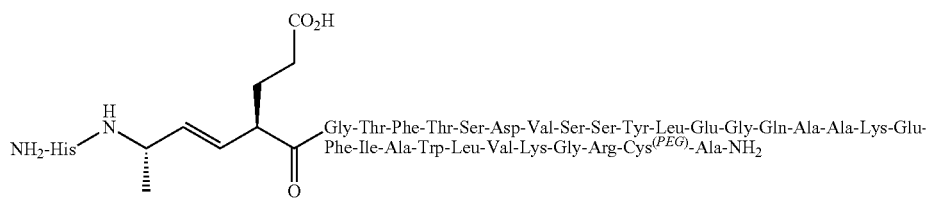

(Namely, the compound of example 17 is

[Q-linker-a8-9]GLP-1-(7-37)-Cys$^{(PEG)}$-Ala-NH$_2$

The desired GLP-1 analog is synthesized by using the same sequence and conditions as described for Example 13 and 20 KDa mPEG-SPA used.

Example 18

Synthesis of

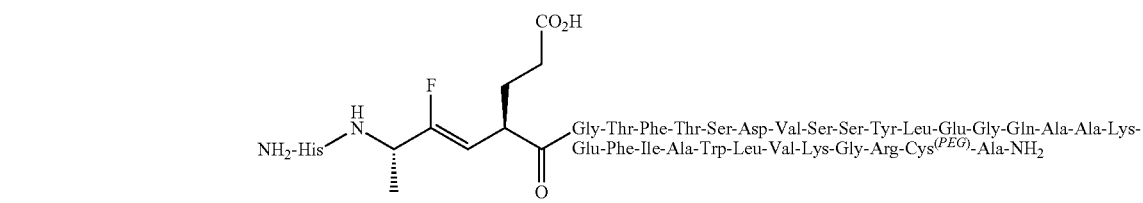

(Namely, the compound of example 18 is

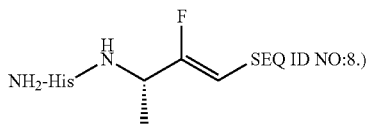

SEQ ID NO:8.)

[Q-linker-b8-9]GLP-1-(7-37)-Cys$^{(PEG)}$-Ala-NH$_2$

The desired GLP-1 analog is synthesized by using the same sequence and conditions as described for Example 13 and 20 KDa mPEG-SPA used.

Example 19

Synthesis of

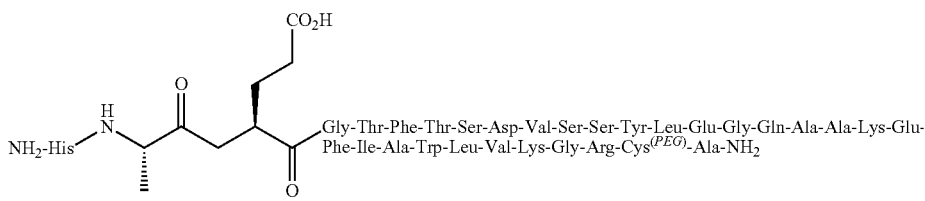

(Namely, the compound of example 19 is

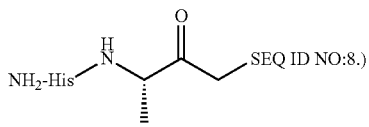

SEQ ID NO:8.)

[Q-linker-e8-9]GLP-1-(7-37)-Cys$^{(PEG)}$-Ala-NH$_2$

The desired GLP-1 analog is synthesized by using the same sequence and conditions as described for Example 13 and 20KDa mPEG-SPA used.

Example 20

Synthesis of

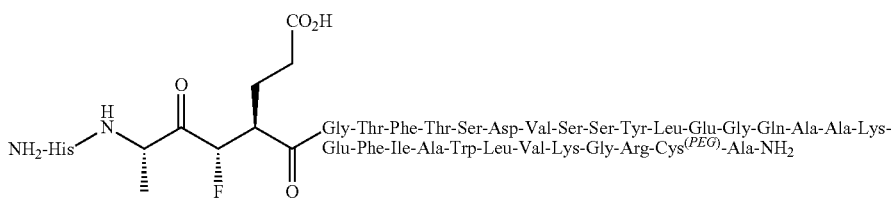

(Namely, the compound of example 20 is

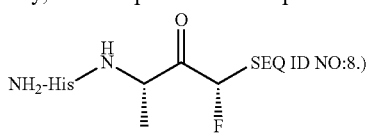

SEQ ID NO:8.)

[Q-linker-f8-9]GLP-1-(7-37)-Cys$^{(PEG)}$-Ala-NH$_2$

The desired GLP-1 analog is synthesized by using the same sequence and conditions as described for Example 13 and 20 KDa mPEG-SPA used.

Example 21

Stability to DPP-IV in Vitro

GLP-1 (100 μL, 5 nmol/L), an equivalent amount of purified in house synthesized GLP-1 analogues were prepared in triethylamine☐HCl buffer (10 mmol/L; pH 7.4). DPP-IV (5 mU, 900 μL) was added, and the solutions were incubated at 37 ° C. At the indicated time points, 100 μL was removed from the reaction mixture, and reactions were terminated by the addition of 5 μL of 10% (v/v) TFA. Each sample was analyzed by MALDI-TOF MS and RP-HPLC as described.

| GLP-1 or GLP-1 analogues plus DPP-IV | remaining peptide (1 h) (%) | remaining peptide (24 h) (%) |
|---|---|---|
| GLP-1 | 20 | 0 |
| [Q-linker-c8, Glu22]GLP-1-(7-37)-peptide | 98 | 90 |
| [Q-linker-b8-9, Glu22]GLP-1-(7-37)-peptide | 98 | 92 |
| [Q-linker-e8-9, Glu22]GLP-1-(7-37)-peptide | 98 | 91 |
| N-ε$^{26}$-[γ-L-glutamyl(N-α-hexadecanoyl)]-[Q-linker-d8,Arg34]GLP-1-(7-37)-peptide | 98 | 98 |
| N-ε$^{26}$-[γ-L-glutamyl(N-α-hexadecanoyl)]-[Q-linker-c8,Arg34]GLP-1-(7-37)-peptide | 98 | 98 |
| N-ε$^{26}$-[γ-L-glutamyl(N-α-hexadecanoyl)]-[Q-linker-a8-9,Arg34]GLP-1-(7-37)-peptide | 98 | 98 |
| [Q-linker-c8]GLP-1-(7-37)-Cys$^{(PEG)}$-Ala-NH$_2$ | 98 | 98 |

-continued

| GLP-1 or GLP-1 analogues plus DPP-IV | remaining peptide (1 h) (%) | remaining peptide (24 h) (%) |
|---|---|---|
| [Q-linker-b8]GLP-1-(7-37)-Cys$^{(PEG)}$-Ala-NH$_2$ | 98 | 98 |

| GLP-1 or GLP-1 analogues plus DPP-IV | remaining peptide (1 h) (%) | remaining peptide (24 h) (%) |
|---|---|---|
| [Q-linker-e8]GLP-1-(7-37)-Cys$^{(PEG)}$-Ala-NH$_2$ | 98 | 98 |

Example 22 cAMP Formation in a Cell Line Expressing the Cloned Human GLP-1 Receptor

In order to demonstrate efficacy of the GLP-1 derivatives, their ability to stimulate formation of cAMP in a cell line expressing the cloned human GLP-1 receptor was tested. An EC$_{50}$ was calculated from the dose-response curve.

In this radioimmuniassay, NIT-1, a pancreatic beta-cell line established from a transgenic NOD/Lt mouse is used. The assay was carried out in 96-weil microtiter plates in a total volume of 140 µl. The buffer used was 50 mmol/l Tris-HCl, pH 7.4 with the addition of 1 mmol/l EGTA, 1.5 mmol/1MgSO$_4$,1.7 mmol/l ATP, 20 mM GTP, 2 mmol/l 3-isobutyl-1-methylxanthine, 0.01% Tween-20 and 0.1% human serum albumin. Compounds to be tested for agonist activity were dissolved and diluted in buffer, added to the membrane preparation and the mixture was incubated for 2 h at 37° C. The reaction was stopped by the addition of 25 µl of 0.05 mol/1HCl. Samples were diluted 10 fold before analysis for cAMP by a scintillation proximity is assay.

| GLP-1 or GLP-1 analogues plus DPP-IV | Cell based cAMP ED$_{50}$ (pM) |
|---|---|
| GLP-1 | 60 |
| [Q-linker-c8, Glu22]GLP-1-(7-37)-peptide | 120 |
| [Q-linker-b8-9, Glu22]GLP-1-(7-37)-peptide | 98 |
| [Q-linker-e8-9, Glu22]GLP-1-(7-37)-peptide | 78 |
| N-ε$^{26}$-[γ-L-glutamyl(N-α-hexadecanoyl)]-[Q-linker-d8,Arg34]GLP-1-(7-37)-peptide | 68 |
| N-ε$^{26}$-[γ-L-glutamyl(N-α-hexadecanoyl)]-[Q-linker-c8,Arg34]GLP-1-(7-37)-peptide | 98 |
| N-ε$^{26}$-[γ-L-glutamyl(N-α-hexadecanoyl)]-[Q-linker-a8-9,Arg34]GLP-1-(7-37)-peptide | 135 |
| [Q-linker-c8]GLP-1-(7-37)-Cys$^{(PEG)}$-Ala-NH$_2$ | 168 |
| [Q-linker-b8]GLP-1-(7-37)-Cys$^{(PEG)}$-Ala-NH$_2$ | 239 |
| [Q-linker-e8]GLP-1-(7-37)-Cys$^{(PEG)}$-Ala-NH$_2$ | 334 |

Example 23

Antihyperglycemic Activity of GLP-1 Analogues

Diabetes-induced db/db mice were divided into 4 groups (n=5) and were fasted for 16 hours. Saline solution, 100 µg/kg of GLP-1 (7-36) amide, 100 µg eq/kg of [Q-linker-c8, Glu22]GLP-1-(7-37)-peptide and 100 µg eq/kg of N-ε$^{26}$-[γ-L-glutamyl(N-α-hexadecanoyl)]-[Q-linker-d8,Arg34]GLP-1-(7-37)-peptide were intraperitoneally injected and 1 g/kg of glucose solution was orally administered after 10 minutes. After −10, 0, 10, 20, 30, 60, 90, 120 and 180 minutes, blood samples were taken and blood glucose levels were measured. The effects of inhibiting blood glucose increase of GLP-I (7-36) amide, [Q-linker-c8, Glu22]GLP-1-(7-37)-peptide and N-ε$^{26}$-[γ-L-glutamyl(N-α-hexadecanoyl)]-[Q-linker-d8,Arg34]GLP-1-(7-37)-peptide were compared by calculating the area under the blood glucose level to time (0-180 minutes) curve. AUC of GLP-1(7-36) amide group was 25165±4463 mg-min/dl, which is a decreased value by 27.8%, as compared to the saline solution group (34864+4774 mg.min/dl). However, [Q-linker-c8, Glu22]GLP-1-(7-37)-peptide and N-ε$^{26}$-[γ-L-glutamyl(N-α-hexadecanoyl)]-[Q-linker-d8,Arg34]GLP-1-(7-37)-peptide are 14470+5700 mg-min/dl and 17520+2484 mg-min/dl, respectively (i.e. 58.5% and 49.7% decreases each). These results show that [Q-linker-c8, Glu22]GLP-1-(7-37)-peptide and N-ε$^{26}$-[γ-L-glutamyl(N-α-hexadecanoyl)]-[Q-linker-d8,Arg34]GLP-1-(7-37)-peptide have much enhanced activity for inhibiting blood glucose level as compared to GLP-I (7-36) amide.

The invention claimed is:

1. A GLP-1 analog which is [Q-Linker-c8, Glue22]GLP-1-(7-37)-peptide wherein Q-linker-c8 has the structure

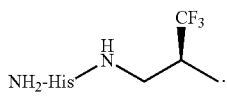

2. A pharmaceutical composition comprising a GLP-1 analog of claim 1 and a pharmaceutically acceptable excipient.

3. The pharmaceutical composition according to claim 2, wherein the pharmaceutical composition is suited for parenteral administration.

4. A method for preventing or treating hyperglycemia, type 2 diabetes, impaired glucose tolerance, type 1 diabetes, obesity, hypertension, syndrome X, dyslipidemia, cognitive disorders, atherosclerosis, myocardial infarction, coronary heart disease, stroke, inflammatory bowel syndrome, dyspepsia, or gastric ulcers in a subject, comprising administering to the subject in need thereof a therapeutically effective amount of a GLP-1 analog of claim 1.

5. A method for preventing or delaying the progression of type 2 diabetes in a subject, comprising administering to the subject in need thereof a therapeutically effective amount of a GLP-1 analog of claim 1.

6. A method for decreasing food intake, decreasing β-cell apoptosis, increasing β-cell function and β-cell mass, or restoring glucose sensitivity to β-cells in a subject, comprising administering to the subject in need thereof a therapeutically effective amount of a GLP-1 analog of claim 1.

* * * * *

SEQUENCE LISTING

```
<160> NUMBER OF SEQ ID NOS: 8

<210> SEQ ID NO 1
<211> LENGTH: 27
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: X is selected from the group consisting of
      serine and histidine
<220> FEATURE:
<221> NAME/KEY: MISC_FEATURE
<222> LOCATION: (7)..(7)
<223> OTHER INFORMATION: X is selected from the group consisting of
      valine, lysine, and leucine
<220> FEATURE:
<221> NAME/KEY: MISC_FEATURE
<222> LOCATION: (9)..(9)
<223> OTHER INFORMATION: X is selected from the group consisting of
      serine, serine, arginine, and lysine
<220> FEATURE:
```

```
<221> NAME/KEY: MISC_FEATURE
<222> LOCATION: (13)..(14)
<223> OTHER INFORMATION: X is selected from the group consisting of
      glycine, Aib, and glutamic acid
<220> FEATURE:
<221> NAME/KEY: MISC_FEATURE
<222> LOCATION: (17)..(18)
<223> OTHER INFORMATION: X is selected from the group consisting of
      glycine, lysine, arginine, leucine, asparagine, and Aib
<220> FEATURE:
<221> NAME/KEY: MISC_FEATURE
<222> LOCATION: (25)..(27)
<223> OTHER INFORMATION: X is selected from the group consisting of
      glycine, lysine, arginine, leucine, asparagine, and Aib

<400> SEQUENCE: 1

Gly Thr Phe Thr Xaa Asp Xaa Ser Xaa Thr Leu Glu Xaa Xaa Ala Ala
1               5                   10                  15

Xaa Xaa Phe Ile Ala Trp Leu Val Xaa Xaa Xaa
            20                  25

<210> SEQ ID NO 2
<211> LENGTH: 28
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: X is selected from the group consisting of
      serine and histidine, wherein one or more of the carbon atoms of
      said amino acid is optionally substituted with one or more alkyl
      groups
<220> FEATURE:
<221> NAME/KEY: MISC_FEATURE
<222> LOCATION: (7)..(7)
<223> OTHER INFORMATION: X is selected from the group consisting of
      valine, lysine and leucine, wherein one or more of the carbon
      atoms of said amino acid is optionally substituted with one or
      more alkyl groups
<220> FEATURE:
<221> NAME/KEY: MISC_FEATURE
<222> LOCATION: (9)..(9)
<223> OTHER INFORMATION: X is selected from the group consisting of
      serine, arginine and lysine, wherein one or more of the carbon
      atoms of said amino acid is optionally substituted with one or
      more alkyl groups
<220> FEATURE:
<221> NAME/KEY: MISC_FEATURE
<222> LOCATION: (13)..(13)
<223> OTHER INFORMATION: X is selected from the group consisting of
      glycine, Aib and glutamic acid, wherein one or more of the carbon
      atoms of said amino acid is optionally substituted with one or
      more alkyl groups
<220> FEATURE:
<221> NAME/KEY: MISC_FEATURE
<222> LOCATION: (14)..(14)
<223> OTHER INFORMATION: X is selected from the group consisting of
      glutamine, glycine, Aib and glutamic acid, wherein one or more of
      the carbon atoms of said amino acid is optionally substituted with
      one or more alkyl groups
<220> FEATURE:
<221> NAME/KEY: MISC_FEATURE
<222> LOCATION: (17)..(17)
<223> OTHER INFORMATION: X is selected from the group consisting of
      glycine, lysine, arginine, leucine and asparagine, or Aib
      (aminoisobutyric acid), wherein one or more of the carbon atoms of
      said amino acid is optionally substituted with one or more alkyl
      groups
<220> FEATURE:
<221> NAME/KEY: MISC_FEATURE
<222> LOCATION: (18)..(18)
<223> OTHER INFORMATION: X is selected from the group consisting of
      glutamic acid, glycine, lysine, arginine, leucine, asparagine, and
      Aib (aminoisobutyric acid), wherein one or more of the carbon
```

-continued atoms of said amino acid is optionally substituted with one or
more
<220> FEATURE:
<221> NAME/KEY: MISC_FEATURE
<222> LOCATION: (25)..(27)
<223> OTHER INFORMATION: X is selected from the group consisting of
glycine, lysine, arginine, leucine, asparagine, and Aib
(aminoisobutyric acid), wherein one or more of the carbon atoms of
said amino acid is optionally substituted with one or more alkyl
groups

<400> SEQUENCE: 2

Gly Thr Phe Thr Xaa Asp Xaa Ser Xaa Tyr Leu Glu Xaa Xaa Ala Ala
1               5                   10                  15

Xaa Xaa Phe Ile Ala Trp Leu Val Xaa Xaa Xaa Gly
            20                  25

<210> SEQ ID NO 3
<211> LENGTH: 29
<212> TYPE: PRT
<213> ORGANISM: Artificial sequence
<220> FEATURE:
<223> OTHER INFORMATION: Synthetic

<400> SEQUENCE: 3

Glu Gly Thr Phe Thr Ser Asp Val Ser Ser Tyr Leu Glu Glu Gln Ala
1               5                   10                  15

Ala Lys Glu Phe Ile Ala Trp Leu Val Lys Gly Arg Gly
            20                  25

<210> SEQ ID NO 4
<211> LENGTH: 28
<212> TYPE: PRT
<213> ORGANISM: Artificial sequence
<220> FEATURE:
<223> OTHER INFORMATION: Synthetic

<400> SEQUENCE: 4

Gly Thr Phe Thr Ser Asp Val Ser Ser Tyr Leu Glu Glu Gln Ala Ala
1               5                   10                  15

Lys Glu Phe Ile Ala Trp Leu Val Lys Gly Arg Gly
            20                  25

<210> SEQ ID NO 5
<211> LENGTH: 29
<212> TYPE: PRT
<213> ORGANISM: Artificial sequence
<220> FEATURE:
<223> OTHER INFORMATION: Synthetic

<400> SEQUENCE: 5

Glu Gly Thr Phe Thr Ser Asp Val Ser Ser Tyr Leu Glu Glu Gln Ala
1               5                   10                  15

Ala Lys Glu Phe Ile Ala Trp Leu Val Arg Gly Arg Gly
            20                  25

<210> SEQ ID NO 6
<211> LENGTH: 28
<212> TYPE: PRT
<213> ORGANISM: Artificial sequence
<220> FEATURE:
<223> OTHER INFORMATION: Synthetic

<400> SEQUENCE: 6

Gly Thr Phe Thr Ser Asp Val Ser Ser Tyr Leu Glu Glu Gln Ala Ala
1               5                   10                  15

```
Lys Glu Phe Ile Ala Trp Leu Val Arg Gly Arg Gly
            20                  25

<210> SEQ ID NO 7
<211> LENGTH: 29
<212> TYPE: PRT
<213> ORGANISM: Artificial sequence
<220> FEATURE:
<223> OTHER INFORMATION: Synthetic

<400> SEQUENCE: 7

Glu Gly Thr Phe Thr Ser Asp Val Ser Ser Tyr Leu Glu Gly Gln Ala
1               5                   10                  15

Ala Lys Glu Phe Ile Ala Trp Leu Val Arg Gly Arg Gly
            20                  25

<210> SEQ ID NO 8
<211> LENGTH: 30
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (29)..(29)
<223> OTHER INFORMATION: X is cysteine linked to monomethoxypolyethylene
      glycol maleimide

<400> SEQUENCE: 8

Glu Gly Thr Phe Thr Ser Asp Val Ser Ser Tyr Leu Glu Gly Gln Ala
1               5                   10                  15

Ala Lys Glu Phe Ile Ala Trp Leu Val Lys Gly Arg Xaa Ala
            20                  25              30
```